United States Patent
Sinibaldi et al.

(10) Patent No.: US 12,410,254 B2
(45) Date of Patent: Sep. 9, 2025

(54) TREATMENT OF CARDIOMETABOLIC DISEASE WITH INHIBITORS OF TYPE I INTERFERON SIGNALLING

(71) Applicant: ASTRAZENECA AB, Södertälje (SE)

(72) Inventors: Dominic Sinibaldi, Gaithersburg, MD (US); Wendy White, Gaithersburg, MD (US); Michael Smith, Gaithersburg, MD (US); Kerry Casey, Gaithersburg, MD (US); Gabor Illei, Gaithersburg, MD (US)

(73) Assignee: ASTRAZENECA AB, Sodertalje (SE)

( * ) Notice: Subject to any disclaimer, the term of this patent is extended or adjusted under 35 U.S.C. 154(b) by 0 days.

(21) Appl. No.: 18/394,365

(22) Filed: Dec. 22, 2023

(65) Prior Publication Data
US 2024/0158519 A1    May 16, 2024

Related U.S. Application Data

(63) Continuation of application No. 18/336,368, filed on Jun. 16, 2023, now abandoned, which is a continuation of application No. 17/999,257, filed as application No. PCT/EP2021/064312 on May 28, 2021, now abandoned.

(60) Provisional application No. 63/031,854, filed on May 29, 2020.

(51) Int. Cl.
| | |
|---|---|
| A61K 39/395 | (2006.01) |
| A61K 39/00 | (2006.01) |
| A61P 9/10 | (2006.01) |
| C07K 16/28 | (2006.01) |

(52) U.S. Cl.
CPC ............ *C07K 16/2866* (2013.01); *A61P 9/10* (2018.01); *A61K 2039/545* (2013.01); *C07K 2317/565* (2013.01); *C07K 2317/76* (2013.01)

(58) Field of Classification Search
None
See application file for complete search history.

(56) References Cited

FOREIGN PATENT DOCUMENTS

WO    2020/102043    5/2020

OTHER PUBLICATIONS

White et al. Alteration of mediators of vascular inflammation by anifrolumab in the phase iib muse study in SLE. Annals of the Rheumatic Diseases, (Jun. 2018) vol. 77, Supp. 2, pp. 136-137. Abstract No. OP0174. (Year: 2018).*
Casey K, et al. Alteration of Vascular Inflammatory Markers in SLE By Anifrolumab in the Phase IIb Muse Study [abstract]. Arthritis Rheumatol. Oct. 2018; 70 (suppl 9), Abstract # 975. (Year: 2018).*
King et al. IRF3 and Type I Interferons Fuel a Fatal Response to Myocardial Infarction. Nat Med. Dec. 2017 ; 23(12): 1481-1487. (Year: 2017).*
Knight and Kaplan. Cardiovascular disease in lupus: insights and updates. Curr Opin Rheumatol. Sep. 2013; 25(5): 597-605. (Year: 2013).*
Merrill J, Furie R, Werth V, et al. THU0295 Anifrolumab Reduces Disease Activity in Multiple Organ Domains in Moderate to Severe Systemic Lupus Erythematosus (SLE). Annals of the Rheumatic Diseases 2016;75:293. (Year: 2016).*
Thacker et al. Type I Interferons Modulate Vascular Function, Repair, Thrombosis, and Plaque Progression in Murine Models of Lupus and Atherosclerosis. Arthritis Rheum . Sep. 2012;64(9):2975-85. (Year: 2012).*
Boshuizen et al. Systemic blocking of the interferon-alpha/beta receptor subunit 1 stimulates arteriogenesis without exacerbating atherosclerosis. Atherosclerosis, (Aug. 2014) vol. 235, No. 2, pp. e27-e28. Abstract No. EAS-0302. (Year: 2014).*
Thacker et al. Type I Interferons Modulate Vascular Function, Repair, Thrombosis and Plaque Progression in Murine Models of Lupus and Atherosclerosis. Arthritis Rheum. Sep. 2012 ; 64(9): 2975-2985. (Year: 2012).*
Teunissen et al. A monoclonal antibody against the interferon-alpha/beta receptor subunit 1 stimulates arteriogenesis in a murine hindlimb-ischemia model without affecting atherosclerosis. European Heart Journal, (Sep. 1, 2014) vol. 35, SUPPL. 1, p. 199. Abstract#: P1100. (Year: 2014).*
Teunissen et al. MAb therapy against the IFN-α/β receptor subunit 1 stimulates arteriogenesis in amurine hindlimb ischaemia model without enhancing atherosclerotic burden. Cardiovascular Research (2015), 107(2), 255-266. (Year: 2015).*
Connelly et al. GlycA, a novel biomarker of systemic inflammation and cardiovascular disease risk. J Transl Med (2017) 15:219. (Year: 2017).*
Murphy et al. From BILAG to BILAG-based combined lupus assessment-30 years on. Rheumatology, 55(8): 1357-1363, 2016. ( Year: 2016).*
Furie et al. Anifrolumab, an Anti-Interferon-α Receptor Monoclonal Antibody, in Moderate-to-Severe Systemic Lupus Erythematosus Arthritis Rheumatol, 69(2):376-386, 2017. (Year: 2017).*
Liu et al. Cardiovascular disease in systemic lupus erythematosus: an update. Curr Opin Rheumatol . Sep. 2018;30(5):441-448. ( Year: 2018).*
Merrill et al. Anifrolumab Reduces Disease Activity in Multiple Organ Domains in Patients With Moderate to Severe Systemic Lupus Erythematosus. Lupus Science and Medicine, 3, Supp. 1, pp. A39, 2016. Abstract: CT-03. (Year: 2016).*
Tibuakuu et al. GlycA, a novel inflammatory marker, is associated with subclinical coronary disease. AIDS, Mar. 2019, 33:547-557. (Year: 2019).*
White et al.OP0174 Alteration of mediators of vascular inflammation by anifrolumab in the phase iib muse study in SLE. Annals of the Rheumatic Diseases 2018;77:136-137. (Year: 2018).*

(Continued)

*Primary Examiner* — Maher M Haddad
(74) *Attorney, Agent, or Firm* — McDonnell Boehnen Hulbert & Berghoff LLP

(57) ABSTRACT

The disclosure relates to methods for the treatment of, or for reducing the risk for development of, a cardiometabolic in a patient using an inhibitor of type I IFN signalling.

Figure 3:
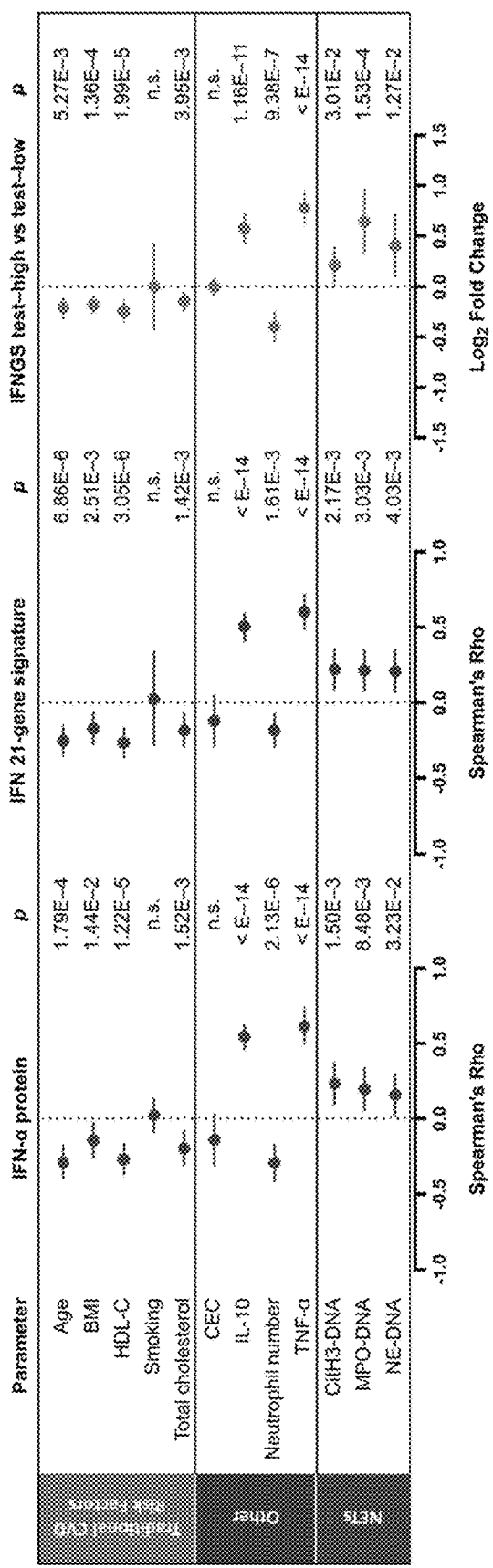

11 Claims, 20 Drawing Sheets
Specification includes a Sequence Listing.

(56) References Cited

OTHER PUBLICATIONS

Casey et al. Alteration of Vascular Inflammatory Markers in SLE by Anifrolumab in the Phase IIb Muse Study. Arthritis Rheumatol. 2018; 70 (suppl 9). (Year: 2018).*

Lee et al. The cytokine network type I IFN-IL-27-IL-10 is augmented in murine and human lupus. J Leukoc Biol. 2019;106;967-975. (Year: 2019).*

Weckerle et al. Large Scale Analysis of Tumor Necrosis Factor Alpha Levels in Systemic Lupus Erythematosus. Arthritis Rheum. Sep. 2012 ; 64(9): 2947-2952. doi:10.1002/art.34483. (Year: 2012).*

Goldwater et al. Interleukin-10 as a predictor of major adverse cardiovascular events in a racially and ethnically diverse population: Multi-Ethnic Study of Atherosclerosis. Ann Epidemiol. Feb. 2019 ; 30; 9-14.e1. doi:10.1016/j.annepidem.2018.08.013. (Year: 2018).*

Morand Eric F. et al., "Trial of Anifrolumab in Active Systemic Lupus Erythematosus", The New England Journal of Medicine Jan. 16, 2020 (Jan. 1, 2020), vol. 382, No. 3, p. 211-221.

Onuora Sarah, "Positive results for anifrolumab in phase III SLE trial", Nature Review Rheumatology, Nature Publishing Group Feb. 4, 2020 (Feb. 4, 2020), vol. 16, No. 3, p. 125.

White W. et al. "Alteration of Mediators of Vascular Inflammation by Anifrolumab in the Phase IIb Muse Study in SLE", Annals of Rheumatic Diseases Jun. 14, 2018 (Jun. 14, 2018), vol. 77, pp. 136-137.

* cited by examiner

FIG. 1

BILAG-2004 INDEX    Centre:    Date:    Initials/Hosp No:

♦ Only record manifestations/items <u>due to SLE Disease Activity</u>
♦ Assessment refers to <u>manifestations occurring in the last 4 weeks (compared with the previous 4 weeks)</u>
♦ TO BE USED WITH THE GLOSSARY Record: ND   Not Done
    0   Not present
    1   Improving
    2   Same
    3   Worse
    4   New
    Yes/No OR Value  (where indicated)
    *Y/N   Confirm this is <u>due to SLE activity</u> (Yes/No)

CONSTITUTIONAL
1. Pyrexia - documented > 37.5°C    ( )
2. Weight loss - unintentional > 5%    ( )
3. Lymphadenopathy/splenomegaly    ( )
4. Anorexia    ( )

MUCOCUTANEOUS
5. Skin eruption - severe    ( )
6. Skin eruption - mild    ( )
7. Angio-oedema - severe    ( )
8. Angio-oedema - mild    ( )
9. Mucosal ulceration - severe    ( )
10. Mucosal ulceration - mild    ( )
11. Panniculitis/Bullous lupus - severe    ( )
12. Panniculitis/Bullous lupus - mild    ( )
13. Major cutaneous vasculitis/thrombosis    ( )
14. Digital infarcts or nodular vasculitis    ( )
15. Alopecia - severe    ( )
16. Alopecia - mild    ( )
17. Peri-ungual erythema/chilblains    ( )
18. Splinter haemorrhages    ( )

NEUROPSYCHIATRIC
19. Aseptic meningitis    ( )
20. Cerebral vasculitis    ( )
21. Demyelinating syndrome    ( )
22. Myelopathy    ( )
23. Acute confusional state    ( )
24. Psychosis    ( )
25. Acute inflammatory demyelinating polyradiculoneuropathy    ( )
26. Mononeuropathy (single/multiplex)    ( )
27. Cranial neuropathy    ( )
28. Plexopathy    ( )
29. Polyneuropathy    ( )
30. Seizure disorder    ( )
31. Status epilepticus    ( )
32. Cerebrovascular disease (not due to vasculitis)    ( )
33. Cognitive dysfunction    ( )
34. Movement disorder    ( )
35. Autonomic disorder    ( )
36. Cerebellar ataxia (isolated)    ( )
37. Lupus headache - severe unremitting    ( )
38. Headache from IC hypertension    ( )

MUSCULOSKELETAL
39. Myositis - severe    ( )
40. Myositis - mild    ( )
41. Arthritis ( severe)    ( )
42. Arthritis (moderate)/Tendonitis/Tenosynovitis    ( )
43. Arthritis (mild)/Arthralgia/Myalgia    ( )

Weight (kg):    Serum urea (mmol/l):
African ancestry: Yes/No    Serum albumin (g/l):

CARDIORESPIRATORY
44. Myocarditis - mild    ( )
45. Myocarditis/Endocarditis + Cardiac failure    ( )
46. Arrhythmia    ( )
47. New valvular dysfunction    ( )
48. Pleurisy/Pericarditis    ( )
49. Cardiac tamponade    ( )
50. Pleural effusion with dyspnoea    ( )
51. Pulmonary haemorrhage/vasculitis    ( )
52. Interstitial alveolitis/pneumonitis    ( )
53. Shrinking lung syndrome    ( )
54. Aortitis    ( )
55. Coronary vasculitis    ( )

GASTROINTESTINAL
56. Lupus peritonitis    ( )
57. Abdominal serositis or ascites    ( )
58. Lupus enteritis/colitis    ( )
59. Malabsorption    ( )
60. Protein losing enteropathy    ( )
61. Intestinal pseudo-obstruction    ( )
62. Lupus hepatitis    ( )
63. Acute lupus cholecystitis    ( )
64. Acute lupus pancreatitis    ( )

OPHTHALMIC
65. Orbital inflammation/myositis/proptosis    ( )
66. Keratitis - severe    ( )
67. Keratitis - mild    ( )
68. Anterior uveitis    ( )
69. Posterior uveitis/retinal vasculitis - severe    ( )
70. Posterior uveitis/retinal vasculitis - mild    ( )
71. Episcleritis    ( )
72. Scleritis - severe    ( )
73. Scleritis - mild    ( )
74. Retinal/choroidal vaso-occlusive disease    ( )
75. Isolated cotton-wool spots (cytoid bodies)    ( )
76. Optic neuritis    ( )
77. Anterior ischaemic optic neuropathy    ( )

RENAL
78. Systolic blood pressure (mm Hg)    value ( )  Y/N*
79. Diastolic blood pressure (mm Hg)    value ( )  Y/N*
80. Accelerated hypertension    Yes/No ( )
81. Urine dipstick protein    (+=1, ++=2, +++=3) ( )  Y/N*
82. Urine albumin-creatinine ratio    mg/mmol ( )  Y/N*
83. Urine protein-creatinine ratio    mg/mmol ( )  Y/N*
84. 24 hour urine protein (g)    value ( )  Y/N*
85. Nephrotic syndrome    Yes/No ( )
86. Creatinine (plasma/serum)    μmol/l ( )  Y/N*
87. GFR (calculated)    ml/min/1.73 m$^2$ ( )  Y/N*
88. Active urinary sediment    Yes/No ( )
89. Active nephritis    Yes/No ( )

HAEMATOLOGICAL
90. Haemoglobin (g/dl)    value ( )  Y/N*
91. Total white cell count (x 10$^9$/l)    value ( )  Y/N*
92. Neutrophils (x 10$^9$/l)    value ( )  Y/N*
93. Lymphocytes (x 10$^9$/l)    value ( )  Y/N*
94. Platelets (x 10$^9$/l)    value ( )  Y/N*
95. TTP    ( )
96. Evidence of active haemolysis    Yes/No ( )
97. Coombs' test positive (isolated)    Yes/No ( )

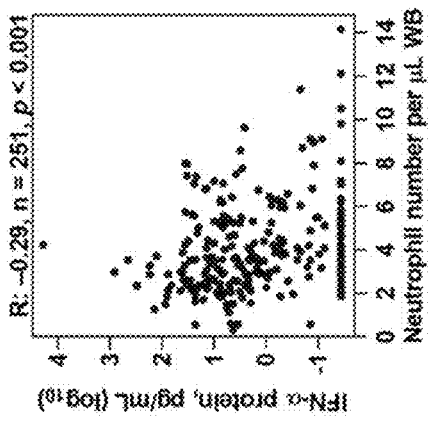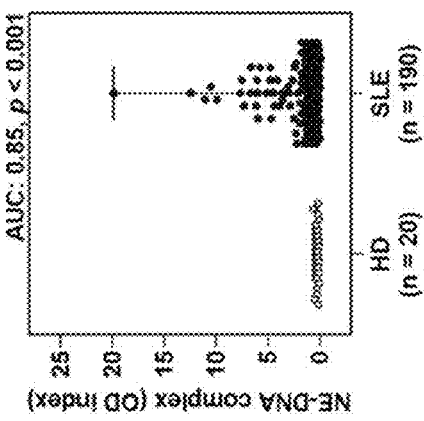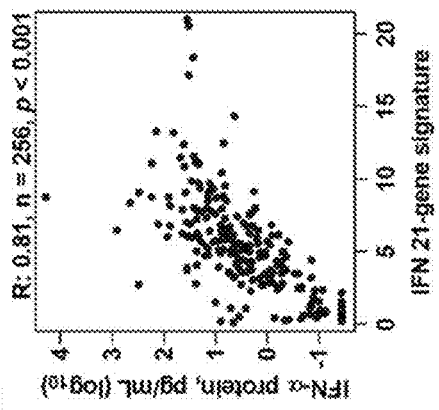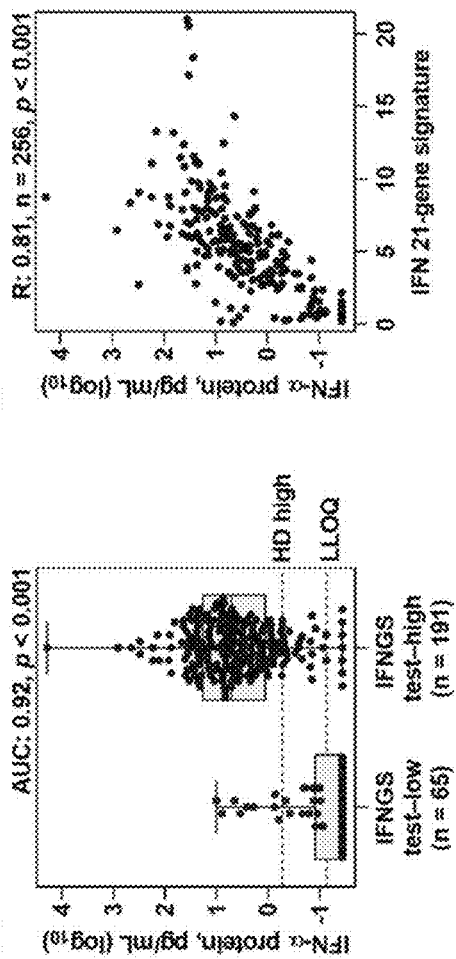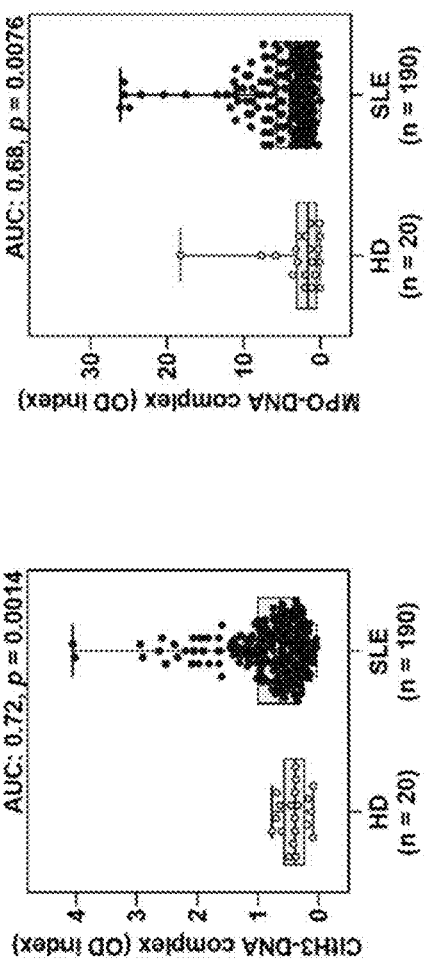
FIG. 2A  FIG. 2B  FIG. 2C  FIG. 2D

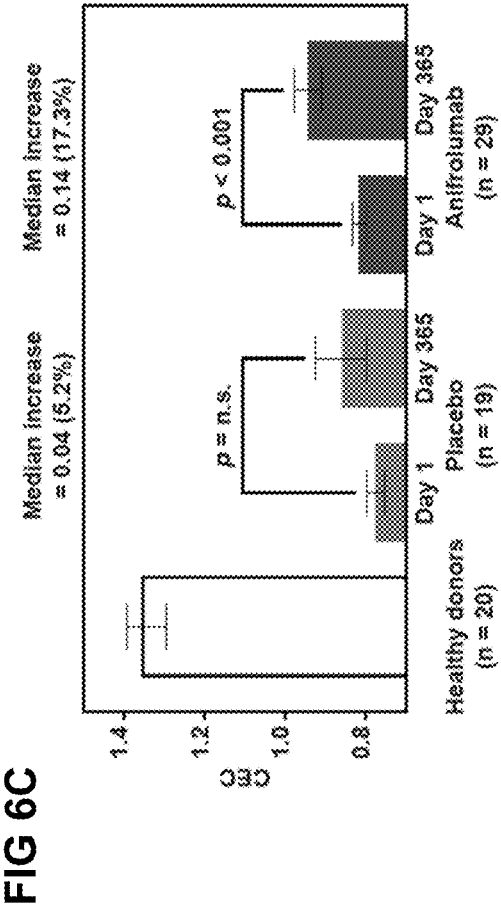
FIG 6C
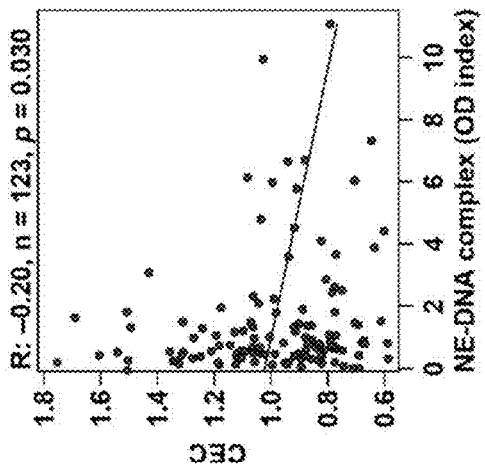
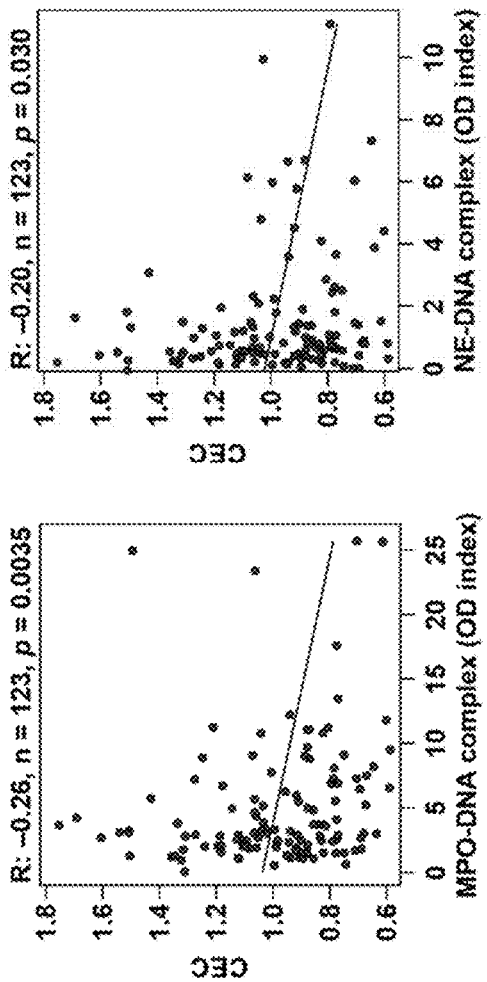
FIG 6A
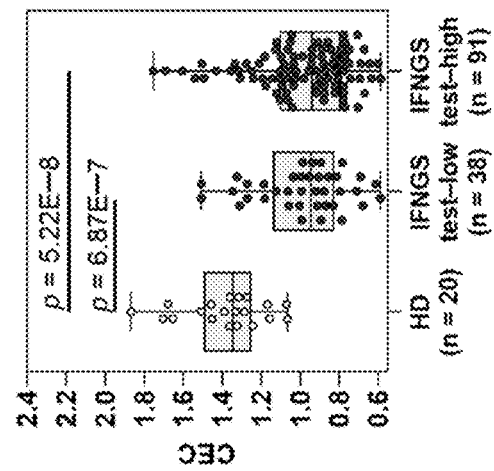
FIG 6B
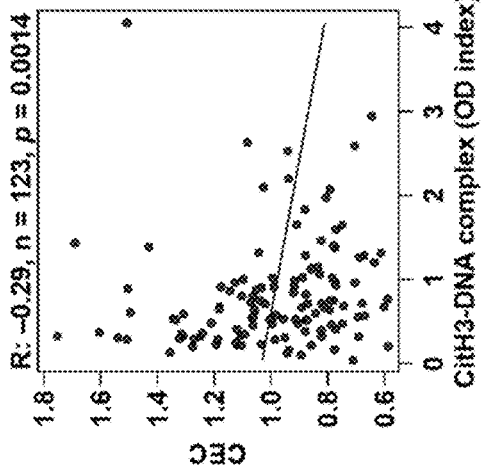

FIG. 9A
FIG. 9B
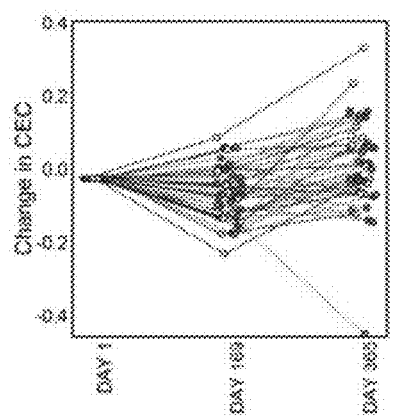
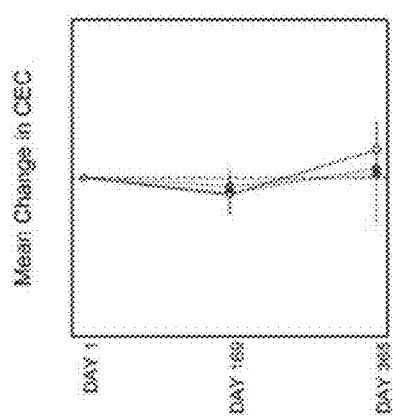
○ Oral corticosteroid dosage < 10 mg/day (n = 12)
● No oral corticosteroid dosage taper (n = 24)
● Oral corticosteroid dosage taper (n = 8)

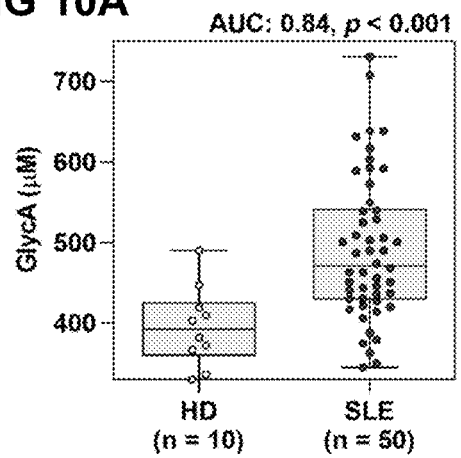
FIG 10A
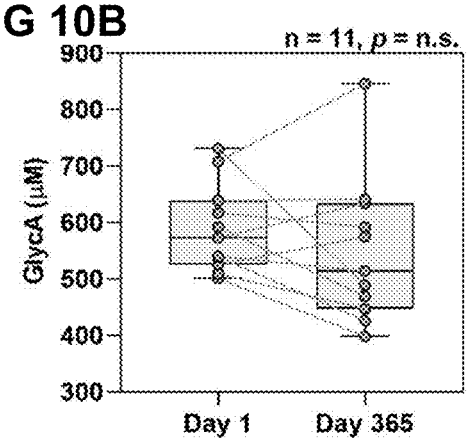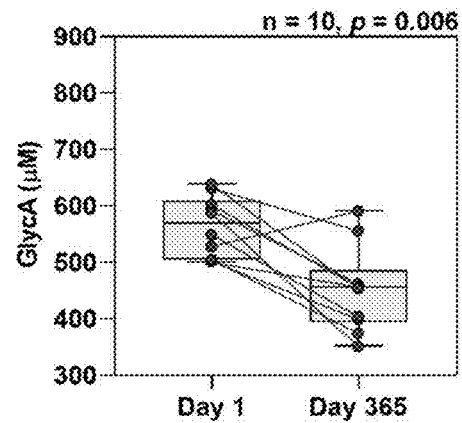
FIG 10B

TREATMENT OF CARDIOMETABOLIC DISEASE WITH INHIBITORS OF TYPE I INTERFERON SIGNALLING

This application is a Track One Continuation of U.S. application Ser. No. 18/336,368, filed on Jun. 16, 2023, which is a Continuation of U.S. application Ser. No. 17/999,257, filed on May 28, 2021, said application Ser. No. 17/999,257 is a 371 application of International Application No. PCT/EP2021/064312 filed May 28, 2021, said International Application No. PCT/EP2021/064312 claims benefit under 35 U.S.C. § 119 (e) of U.S. Provisional Application No. 63/031,854 filed May 29, 2020. Each of the above listed applications is incorporated by reference herein in its entirety for all purposes.

REFERENCE TO THE SEQUENCE LISTING

This application incorporates by reference a Sequence Listing submitted with this application as xml file entitled IFNAR-750_Sequence_Listing.xml created on May 30, 2023, and having a size of 17,147 kilobytes.

1 BACKGROUND

Cardiovascular risk factors, cardiovascular events and subclinical atherosclerosis all occur at a younger age in patients with type I IFN mediated diseases compared with the general population[1]. Cardiovascular disease (CVD) resulting from premature atherosclerosis is one of the predominant causes of morbidity and mortality in systemic lupus erythematosus (SLE)[2,3]. SLE substantially increases the risk of coronary artery disease and myocardial infarction in premenopausal women[4].

Traditional cardiometabolic and cardiorespiratory disease risk factors (e.g. smoking, dyslipidemia, diabetes mellitus (DM), hypertension, central obesity and hyperhomocysteinemia) cannot fully account for this enhanced CVD in SLE patients. Immune dysregulation likely contributes to vascular damage in SLE. However, the exact cellular and molecular mechanisms underlying accelerated atherosclerosis and vasculitis in SLE remain unclear.

Systemic lupus erythematosus (SLE) is a chronic, multisystemic, disabling autoimmune rheumatic disease of unknown aetiology. There is substantial unmet medical need in the treatment of SLE, particularly in subjects with moderate or severe disease. Long-term prognosis remains poor for many subjects.

A significant problem associated with the treatment of SLE, is the heterogeneous clinical manifestations of SLE[5]. Any organ may be affected in SLE, with the skin, joints, and kidneys being the most commonly involved[6-8]. Incomplete disease control leads to progressive organ damage, poor quality of life, and increased mortality, with approximately half of all patients with SLE developing organ damage within 10 years of diagnosis[9,10]. There remains the need for a medical intervention that improves SLE disease activity across multiple systems.

Clinical manifestations of SLE include, but are not limited to, constitutional symptoms, alopecia, rashes, serositis, arthritis, nephritis, vasculitis, lymphadenopathy, splenomegaly, haemolytic anaemia, cognitive dysfunction and other nervous system involvement. Increased hospitalisations and side effects of medications including chronic oral corticosteroids (OCS) and other immunosuppressive treatments add to disease burden in SLE[11-13].

All of the therapies currently used for the treatment of SLE have well known adverse effect profiles and there is a medical need to identify new targeted therapies, particularly agents that may reduce the requirement for corticosteroids and cytotoxic agents. There has been only 1 new treatment (belimumab) for SLE approved by the US Food and Drug Administration (FDA) and European Medicines Agency (EMA) in the approximately 50 years since hydroxychloroquine was approved for use in discoid lupus and SLE. However, belimumab is not approved everywhere, and the uptake has been modest. Many agents currently used to treat SLE, such as azathioprine, cyclophosphamide, and mycophenolate mofetil/mycophenolic acid, have not been approved for the disease. Furthermore, these drugs all have well-documented safety issues and are not effective in all patients for all manifestations of lupus. Antimalarial agents (e.g. hydroxychloroquine) and corticosteroids may be used to control arthralgia, arthritis, and rashes. Other treatments include nonsteroidal anti-inflammatory drugs (NSAIDs); analgesics for fever, arthralgia, and arthritis; and topical sunscreens to minimise photosensitivity. It is often difficult to taper subjects with moderate or severe disease completely off corticosteroids, which cause long-term morbidity and may contribute to early cardiovascular mortality[12,14]. Even small daily doses of 5 to 10 mg prednisone used long-term carry increased risks of side effects such as cataracts, osteoporosis, and coronary artery disease[12].

Direct measurements of aortic vascular inflammation in patients with CVD can be obtained with positron emission tomography/computed tomography and used as risk markers for CVD progression[15]. Short-term changes in arterial inflammation associate with long-term atherosclerosis disease progression, providing validation of measuring subclinical, early stage biomarkers to assess CVD risk. However, these advanced imaging modalities are not accessible to all patients. Furthermore, studying CVD risk in SLE using traditional approaches has low feasibility given disease incidence/prevalence and relatively young age at lupus diagnosis.

The present invention solves one or more of the above-mentioned problems.

2 SUMMARY

The invention relates to a method of treating, or reducing the risk for development of, a cardiometabolic disease in a patient in need thereof, the method comprising administering to the patient a therapeutically effective amount of an inhibitor of type I IFN signalling, wherein the patient has a type I IFN mediated disease.

The invention is supported inter alia by data from two phase Ill, multicenter, multinational, randomized, double-blind, placebo-controlled clinical trials in SLE patients (NCT02446899 and NCT02962960; TULIP I and TULIP II) and a phase II, multinational, multicenter, randomized, double-blind, placebo controlled, parallel-group clinical trial in SLE patients (NCT02962960; MUSE), data analyses of which are presented herein for the first time. These data show that treatment of patients suffering from a type I IFN mediated disease with an inhibitor of type I IFN signalling returns biomarkers of cardiometabolic disease to normal levels. These biomarkers of cardiometabolic disease include GlycA, neutrophil extracellular trap (NET), cholesterol efflux capacity (CEC), TNF-α and/or IL-10.

The data further show that treatment of patients suffering from a type I IFN mediated disease (e.g. SLE) with an inhibitor of type I IFN signalling (e.g. anifrolumab) treats cardiovascular disease in these patients.

3 BRIEF DESCRIPTION OF THE DRAWINGS

FIG. 1: BILAG-2004 Index

FIG. 2: Type I IFN pathway and NET complexes elevated in patients with SLE

FIG. 2A shows IFN-α protein levels measured using the quantitative Simoa™ immunoassay in IFNGS test-low (n=65) and IFNGS test-high (n=191) patients with moderate to severe SLE. Dashed lines represent the maximum IFN-α level in healthy donors. HD high: 0.53 pg/mL; LLOQ: 0.073 pg/mL. FIG. 2B shows IFN-α Simoa™ protein level plotted versus 21-IFNGS (n=256). FIG. 2C shows number of neutrophils plotted versus IFN-α protein Simoa™ levels (n=251). FIG. 2D shows levels of the NET complexes CitH3-DNA, MPO-DNA, and NE-DNA measured using capture ELISA in healthy donors (n=20) and patients with moderate to severe SLE (n=190). Box and whisker plots represent quartiles of each group. P-values were calculated for FIG. 2A and FIG. 2D using a 2-tailed Mann-Whitney U test and for FIG. 2B and FIG. 2C using a 2-tailed Spearman's rank correlation. AUC or Spearman's rank correlation and p-values are above each plot. Abbreviations include: AUC, area under the curve; CitH3, citrullinated histone H3; HD, healthy donors; IFN, interferon; IFNGS, IFN gene signature; LLOQ, lower limit of quantification; MPO, myeloperoxidase; NE, neutrophil elastase; NET, neutrophil extracellular trap; OD, optical density; SLE, systemic lupus erythematosus; WB, whole blood.

FIG. 3: The association of traditional CVD risk factors, IL-10, neutrophil number, TNF-α, and NET complexes with the type I IFN axis in patients with SLE Age, BMI, HDL-C, smoking, total cholesterol, CEC, IL-10 protein, neutrophil number per μL whole blood, TNF-α protein, and circulating NET complexes (CitH3-DNA, MPO-DNA, and NE-DNA) were compared with three measures of the type I IFN pathway: IFN-α protein, 21-IFNGS, and IFNGS test status (IFNGS test-high vs IFNGS test-low). Spearman's rank correlation was used to analyze correlation of parameters with 21-IFNGS and IFN-α protein. Welch's t-test was used to analyze associations of parameters with IFNGS test status, expressed as a Log 2 fold change. Log 2 fold change and Spearman's rank correlation are depicted in forest plots with 95% confidence intervals. Abbreviations include: BMI, body mass index; CitH3, citrullinated histone H3; CEC, cholesterol efflux capacity; CVD, cardiovascular disease; HDL, high-density lipoprotein; IFN, interferon; IFNGS, IFN gene signature; IL, interleukin; MPO, myeloperoxidase; NE, neutrophil elastase; NET, neutrophil extracellular trap; n.s., not significant; SLE, systemic lupus erythematosus; TNF, tumour necrosis factor.

Figure 4:
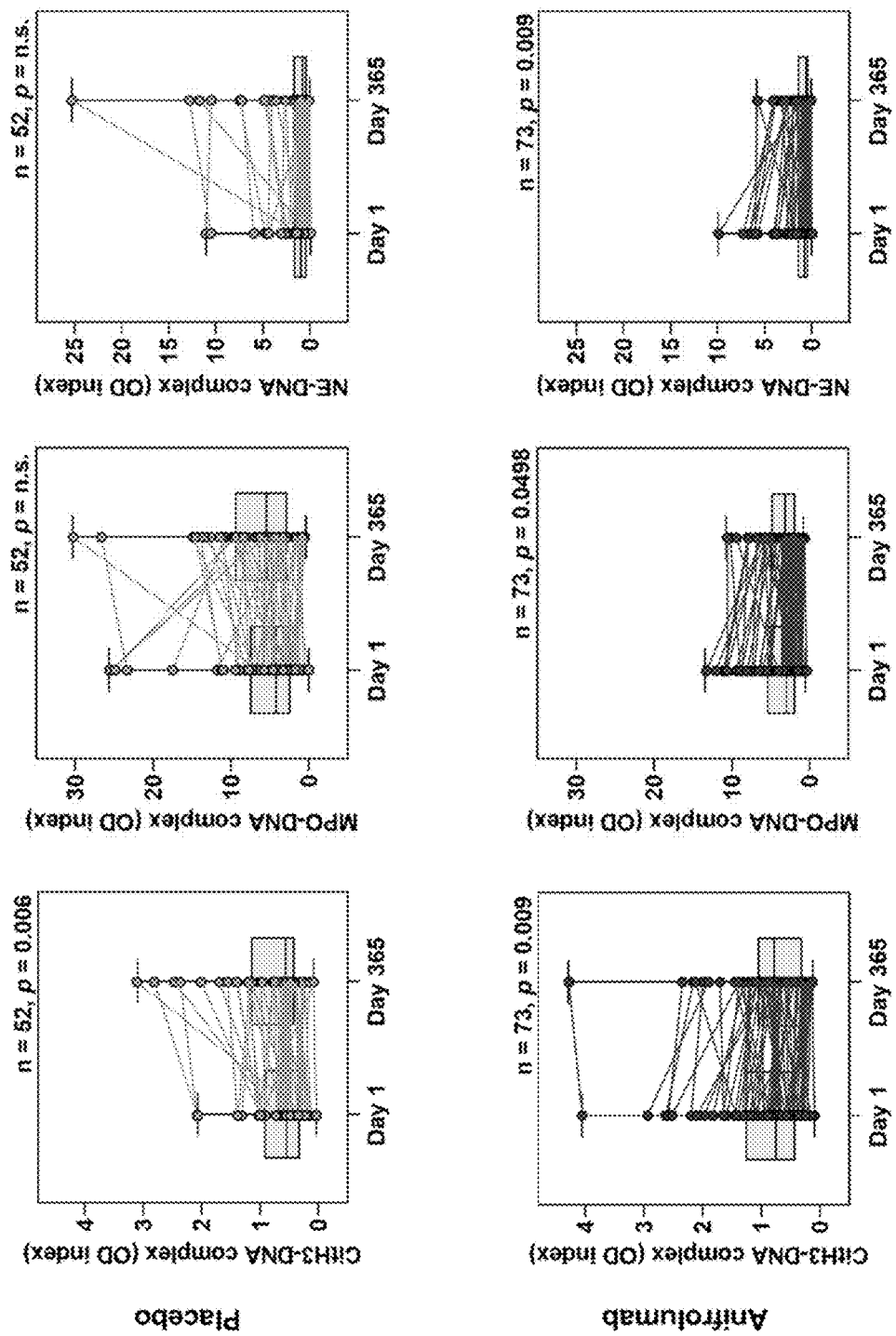

FIG. 4: Type I IFN pathway inhibition significantly decreased circulating NET complexes after 1 year of treatment Levels of the NET complexes CitH3-DNA, MPO-DNA, and NE-DNA were measured using capture ELISA at days 1 and 365 in patients with moderate to severe SLE who received anti-IFNAR1 antibody anifrolumab dosed at 300 mg or placebo. Box and whisker plots represent quartiles of each group. P-values were calculated using a Wilcoxon signed-rank test. *p<0.05, **p 0.01. Abbreviations include: CitH3, citrullinated histone H3; ELISA, enzyme-linked immunosorbent assay; IFN, interferon; IFNAR1, IFN alpha and beta receptor subunit 1; MPO, myeloperoxidase; NE, neutrophil elastase; NET, neutrophil extracellular trap; OD, optical density; SLE, systemic lupus erythematosus.

FIG. 5: Serum TNF-α and IL-10 proteins were elevated in patients with SLE at baseline and were reduced after type I IFN pathway inhibition FIG. 5A shows TNF-α measured using a Simoa™ quantitative immunoassay in IFNGS test-low patients and IFNGS test-high patients with SLE. The healthy donor range is indicated using dashed lines (HD high: 2.9 pg/mL; HD low: 0.68 pg/mL). FIG. 5B shows IL-10 protein levels measured using a Simoa™ quantitative immunoassay in healthy donors, IFNGS test-low patients, and IFNGS test-high patients. For FIG. 5A and FIG. 5B, box and whisker plots represent quartiles of each group. FIG. 5C shows TNF-α protein levels and FIG. 5D shows IL-10 protein levels measured at days 1, 85, 169, and 365 in patients who received placebo or anifrolumab 300 mg. TNF-α protein level was measured in 47-58 patients who received placebo and 62-66 patients who received anifrolumab. IL-10 protein was measured in 47-58 patients who received placebo and 61-66 patients who received anifrolumab. For FIG. 5C and FIG. 5D, percentage change from baseline is plotted with SEM. All p-values were calculated using a 2-tailed Mann-Whitney U test. *p<0.05, p≤0.01, *p≤0.001. Abbreviations include: HD, healthy donor; IFN, interferon; IFNGS, IFN gene signature; IL-10, interleukin-10; SD, standard deviation; SEM, standard error of the mean; SLE, systemic lupus erythematosus; TNF, tumor necrosis factor.

FIG. 6: Impaired CEC at baseline in patients with SLE correlated with NET complex levels and was normalized following type I IFN-signalling inhibition FIG. 6A shows the CEC of Apo-B depleted plasma samples from healthy donors (n=20), IFNGS test-low patients with SLE (n=38), and IFNGS test-high patients with SLE (n=91). FIG. 6B shows the association between CEC and the NET complexes CitH3-DNA, MPO-DNA, and NE-DNA assessed using Spearman's rank correlation in patients with SLE (n=123). FIG. 6C shows CEC plotted with SEM in Apo-B-depleted plasma samples from IFNGS test-high patients with moderate to severe SLE with defects in CEC (2SD below HD mean, 0.96) who received placebo (n=19) or anifrolumab dosed at 300 mg (n=29). The CEC at baseline for healthy donors (n=20) is also shown for reference. P-values were calculated using a Wilcoxon signed-rank test. Abbreviations include: CEC, cholesterol efflux capacity; CitH3, citrullinated histone H3; HD, healthy donor; IFN, interferon; IFNGS, IFN gene signature; MPO, myeloperoxidase; NE, neutrophil elastase; NET, neutrophil extracellular trap; OD, optical density; SD, standard deviation; SEM, standard error of the mean; SLE, systemic lupus erythematosus.

Figure 7:
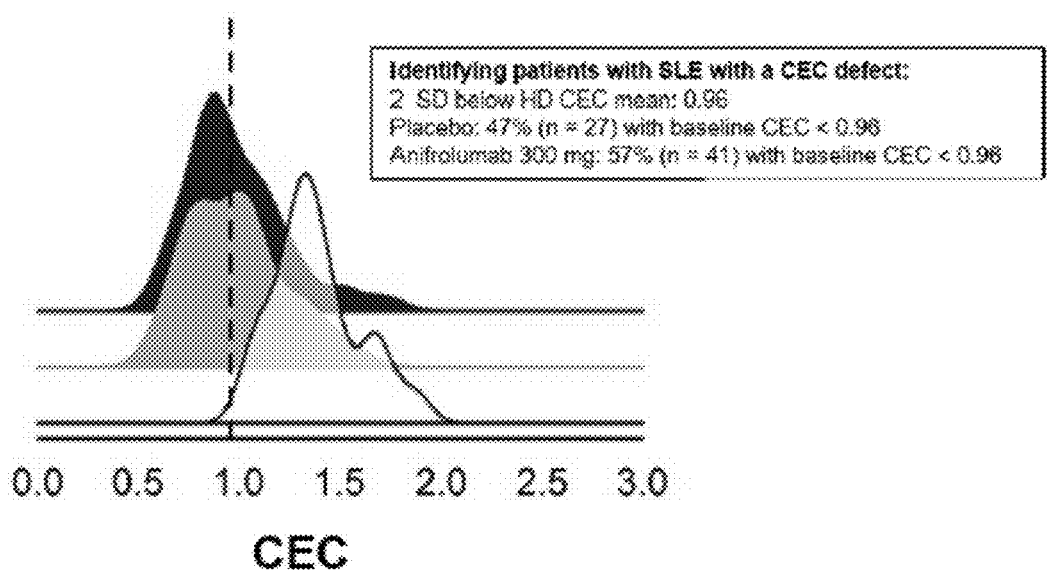

FIG. 7: Identification of a CEC defect in patients with SLE

CEC was measured by liquid scintillation counting to determine radioactive 3H-cholesterol uptake into cellular lipids. CEC percentage distribution is shown for patients who received anifrolumab 300 mg (n=72; purple fill) or placebo (n=57; gray fill) or healthy donors (n=20; black line). The dashed line represents two standard deviations below the healthy donor mean. Abbreviations included: CEC, cholesterol efflux capacity; HD, healthy donor; SD, standard deviation; SLE, systemic lupus erythematosus.

Figure 8A:
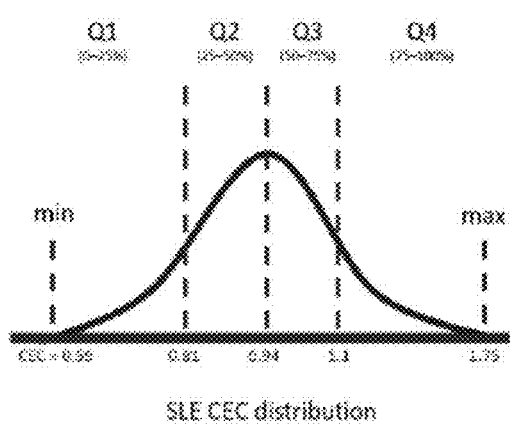
Figure 8B:
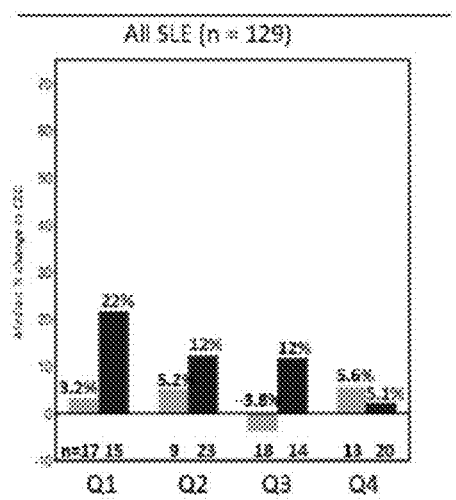

FIG. 8: The greatest CEC increases observed in patients in the lowest quartile of CEC at baseline The greatest CEC increases observed in patients in the lowest quartile of CEC at baseline. CEC was measured by liquid scintillation counting to determine the amount of radioactive 3H-cholesterol uptake into cellular lipids. FIG. 8A shows CEC distribution in patients with moderate to severe SLE. FIG. 8B shows median CEC percentage change on day 365 compared with day 1 in patients with moderate to severe SLE who received anifrolumab. Abbreviations included: CEC, cholesterol efflux capacity; Q, quartile; SLE, systemic lupus erythematosus.

FIG. 9: No effect on CEC of steroid tapering in the placebo group

CEC was measured by liquid scintillation counting in patients with moderate to severe SLE who received oral corticosteroids dosed at <10 mg/day (n=12), no oral corticosteroid dosage tapering (n=24), or oral corticosteroid dosage tapering (n=8). FIG. 9A shows CEC on day 365 compared with day 1 for each patient with SLE. FIG. 9B shows CEC for patients with SLE who received oral corticosteroid dosed at <10 mg/day (n=12), no oral corticosteroid dosage tapering (n=24), or oral corticosteroid dosage tapering (n=8), plotted with 95% confidence intervals. The dashed line represents no change in CEC. Abbreviations included: CEC, cholesterol efflux capacity; SLE, systemic lupus erythematosus.

FIG. 10: GlycA was elevated at baseline in patients with SLE and was reduced following type I IFN pathway inhibition FIG. 10A shows the measurement of baseline GlycA by NMR spectroscopy in healthy donors (n=10) or IFNGS test-high patients with SLE (n=50), with AUC indicated. P-value was calculated using a Mann-Whitney U test. FIG. 10B shows the measurement of GlycA levels at day 1 and day 365 in IFNGS test-high GlycA-high patients (2SD above HD mean, 500 μM) who received anifrolumab dosed at 300 mg (right, n=10), or placebo (left, n=11). P-values were calculated using a Wilcoxon signed-rank test. Box and whisker plots represent quartiles within each group. Abbreviations include: AUC, area under the curve; CEC, cholesterol efflux capacity; HD, healthy donor; IFN, interferon; IFNGS, IFN gene signature; NMR, nuclear magnetic resonance; n.s., not significant; SD, standard deviation; SLE, systemic lupus erythematosus.

Figure 11:
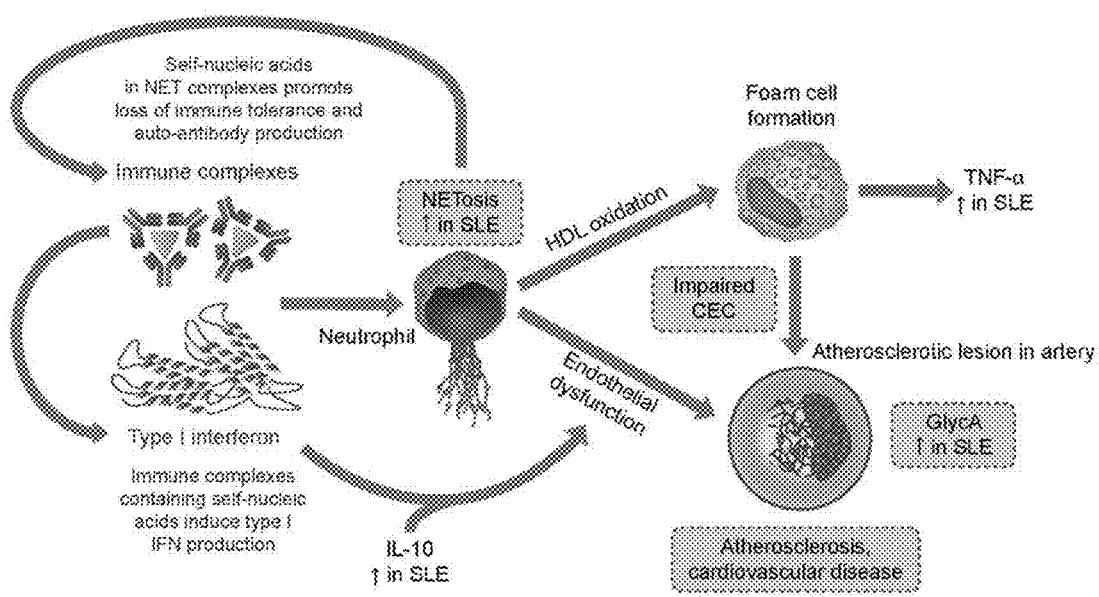

FIG. 11: Type I IFN signalling, neutrophil NET formation, and atherosclerosis pathogenesis in SLE.

Autoantibody-containing immune complex exposure after type I IFN priming activates neutrophils and induces NET formation; consequently, increased NET formation has been observed in patients with SLE. LDGs, a subset of neutrophils with an enhanced capacity to form NETs, are also elevated in patients with SLE. pDCs and other immune cells are activated by NETs and immune complexes to synthesize increased levels of type I IFNs. The self-nucleic acids released in NET complexes promote loss of immune tolerance, autoantibody production, and immune complex formation in a complex regulatory loop. Components within NET complexes oxidize HDL and impair the process of reverse cholesterol transport. Impaired CEC, a cardiometabolic disease marker, leads to the accumulation of lipid-laden macrophages known as foam cells. Foam cells are hallmarks of early atherosclerotic lesions and secrete the pro-inflammatory cytokine, TNF-α, which is elevated in patients with SLE. Type I IFN also induces endothelial dysfunction to contribute to atherosclerosis. IL-10, which is elevated in a subset of patients with SLE, interferes with endothelial differentiation and enhances the effects of type I IFN on vascular repair in patients with SLE. GlycA, which is a marker of cardiometabolic disease and CVD risk, is elevated in patients with SLE. CVD due to premature atherosclerosis is one of the predominant causes of mortality in patients with SLE. Abbreviations include: CEC, cholesterol efflux capacity; CVD, cardiovascular disease; HDL, high-density lipoprotein; IFN, interferon; IL-10, interleukin 10; LDG, low-density granulocyte; NET, neutrophil extracellular trap; pDC, plasmacytoid dendritic cell; SLE, systemic lupus erythematosus; TNF, tumour necrosis factor.

Figure 12:
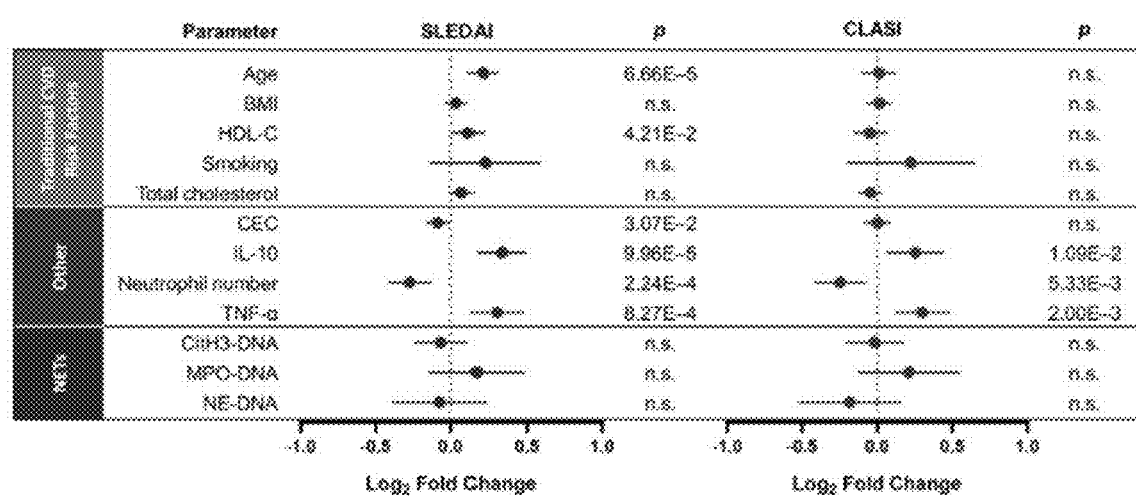

FIG. 12: CEC, number of neutrophils, and TNF-α levels associated with SLE disease activity Log 2 fold changes are indicated for age, BMI, HDL-C, smoking, total cholesterol, CEC, IL-10 protein, neutrophil number per μL whole blood, TNF-α protein, and circulating NET complexes (CitH3-DNA, MPO-DNA, and NE-DNA) compared with two measures of disease activity: SLEDAI and CLASI. Statistical significance was assessed using the Welch's t-test for group comparisons. Abbreviations included: BMI, body mass index; CEC, cholesterol efflux capacity; CitH3, citrullinated histone H3; CLASI, Cutaneous Lupus Erythematosus Disease Area and Severity Index; CVD, cardiovascular disease; HDL-C, high-density lipoprotein count; IL, interleukin; MPO, myeloperoxidase; NE, neutrophil elastase; NET, neutrophil extracellular trap; n.s., not significant; SLE, systemic lupus erythematosus; SLEDAI, SLE Disease Activity Index; TNF, tumor necrosis factor.

Figure 13:
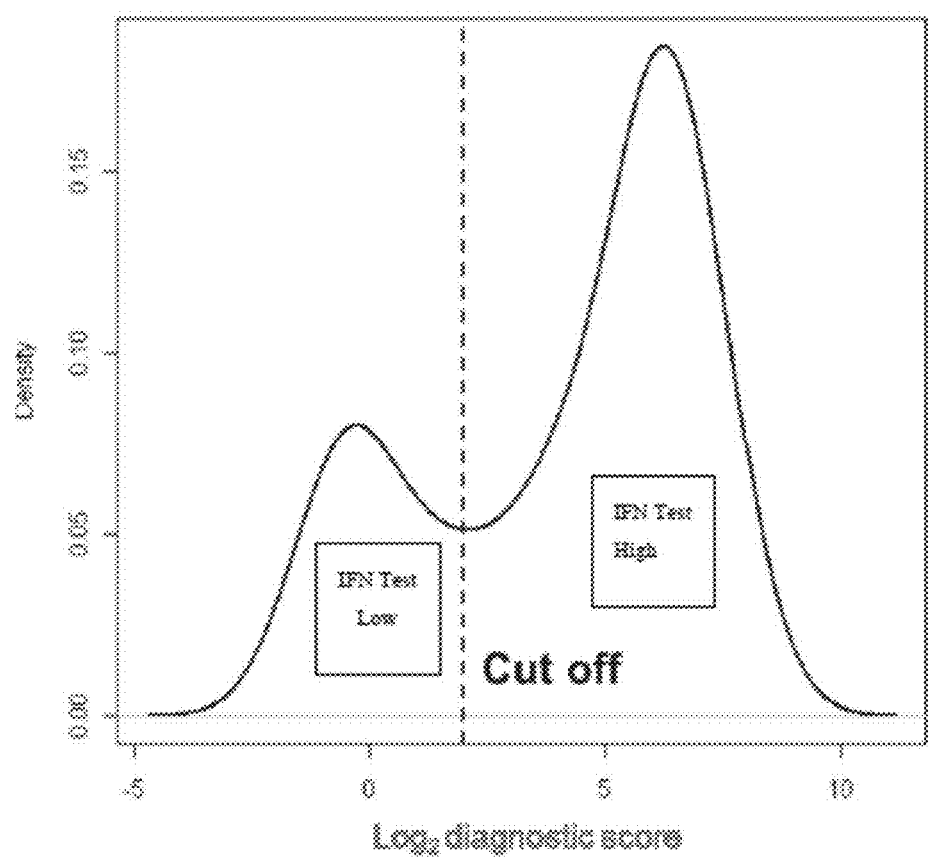

FIG. 13: A density plot of interferon signature scores for SLE subjects

Two distributional modes are illustrated, indicating a clear partitioning between the IFN test high and low subpopulations.

FIG. 14: Baseline organ domain involvement assessed using BILAG-2004 and SLEDAI-2K Baseline organ domain involvement assessed using BILAG-2004 (FIG. 8A) and SLEDAI-2K (FIG. 8B) was similar between treatment groups. BILAG-2004, British Isles Lupus Assessment Group-2004; SLEDAI-2K, Systemic Lupus Erythematosus Disease Activity Index 2000. BILAG-2004 scores range from level A (severe/active disease) to E (no current or previous disease). BILAG-2004 organ domain involvement was defined as an A or B score. SLEDAI-2K organ domain involvement was defined as any SLEDAI-2K organ system score.

Figure 15:
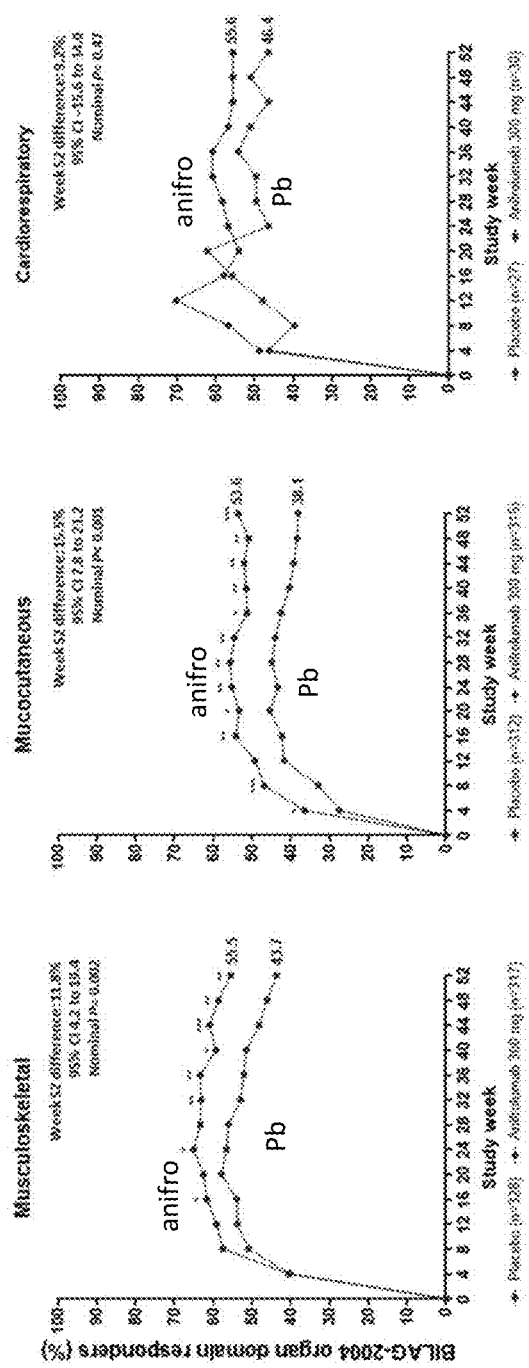

FIG. 15: BILAG-2004 organ domain responders over time

Improvements favouring anifrolumab for the mucocutaneous, musculoskeletal and cardiorespiratory BILAG-2004 domains were observed from Week 4, Week 32 and Week 28, respectively. BILAG-2004, British Isles Lupus Assessment Group-2004. BILAG-2004 organ domain responder is defined as a reduction in baseline A or B score at Week 52. Points are estimates. Estimates are calculated using a stratified Cochran-Mantel-Haenszel approach, with stratification factors as listed in the Methods section. *P<0.05; P<0.01; *P<0.001 (based on Cochran-Mantel-Haenszel approach for the comparison of anifrolumab vs placebo).

Figure 16:
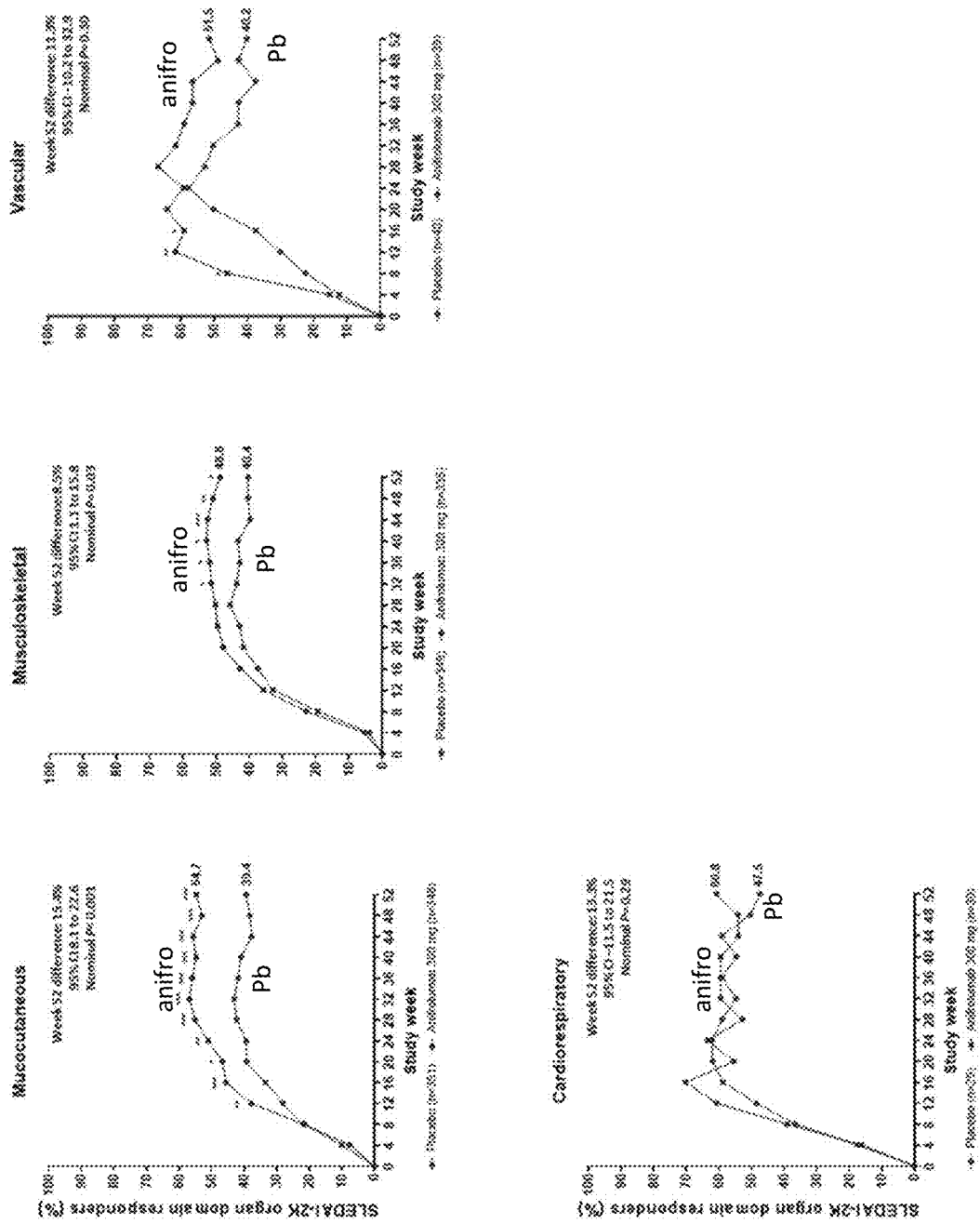

FIG. 16: SLEDAI-2K organ domain responders over time

SLEDAI-2K organ domain responder is defined as a reduction in baseline SLEDAI-2K organ domain score. SLEDAI-2K central nervous system domain is not plotted because there were too few patients in each treatment group. Points are estimates. Estimates are calculated using a stratified Cochran-Mantel-Haenszel approach, with stratification factors as listed in the Methods section. *P<0.05; P<0.01; *P<0.001 (based on Cochran-Mantel-Haenszel approach for the comparison of anifrolumab vs placebo).

Figure 17A:
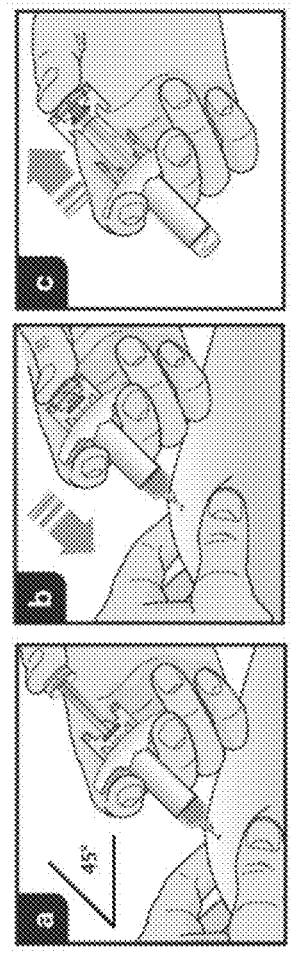

FIG. 17. Delivery device

Figure 17B:
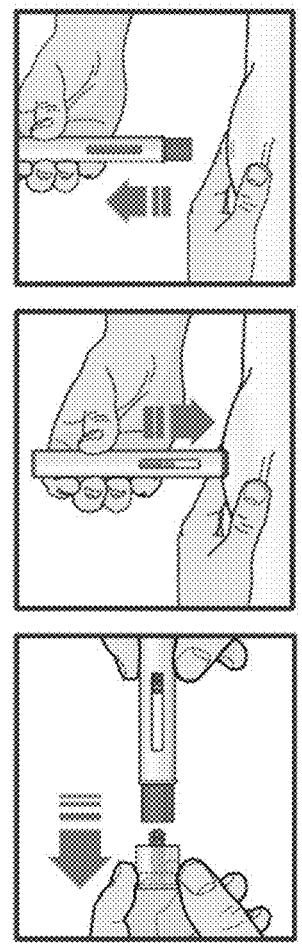

Anifrolumab is administered by an injection device [1] [9] such as a prefilled syringe (PFS) (FIG. 17A) or an autoinjector (AI) (FIG. 17B).

Figure 18A:
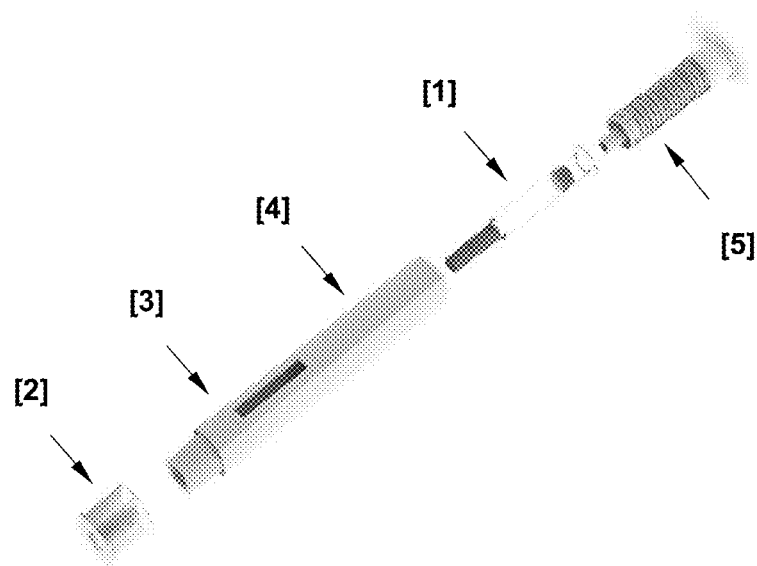

FIG. 18. Autoinjector

Figure 18B:
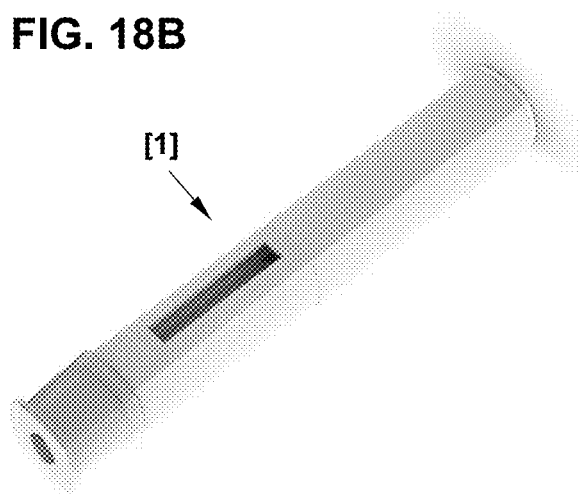
Figure 18C:
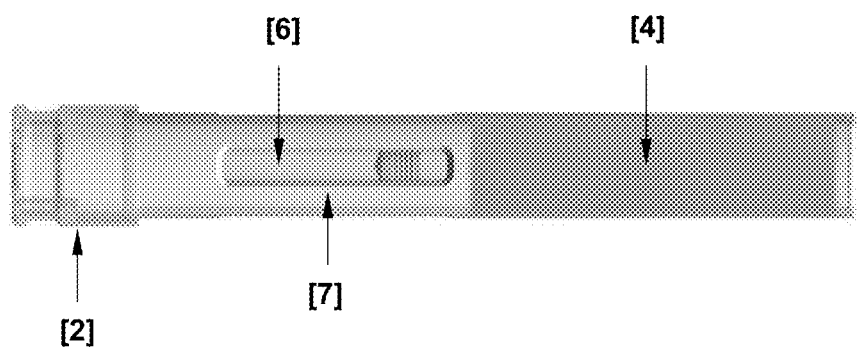

The autoinjector for administering anifrolumab of the functional variant thereof in exploded view (FIG. 18A), assembled (FIG. 18B) and filled with drug substance (FIG. 18C).

FIG. 19. Accessorized pre-filled syringe

Figure 19A:
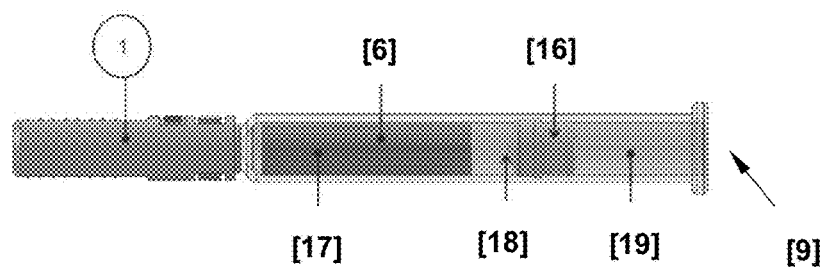
Figure 19B:
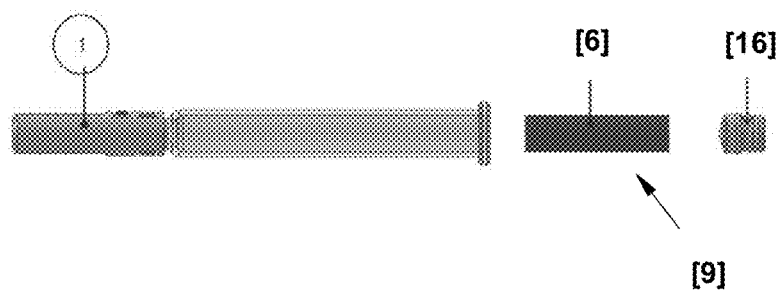

The accessorized pre-filled syringe (APFS) for anifrolumab of the functional variant thereof. The primary tube is shown in assembled form (FIG. 19A) and in exploded view (FIG. 19B). The APFS with its additional components is shown in assembled form (FIG. 19C) and in exploded view FIG. 19D).

Figure 20:
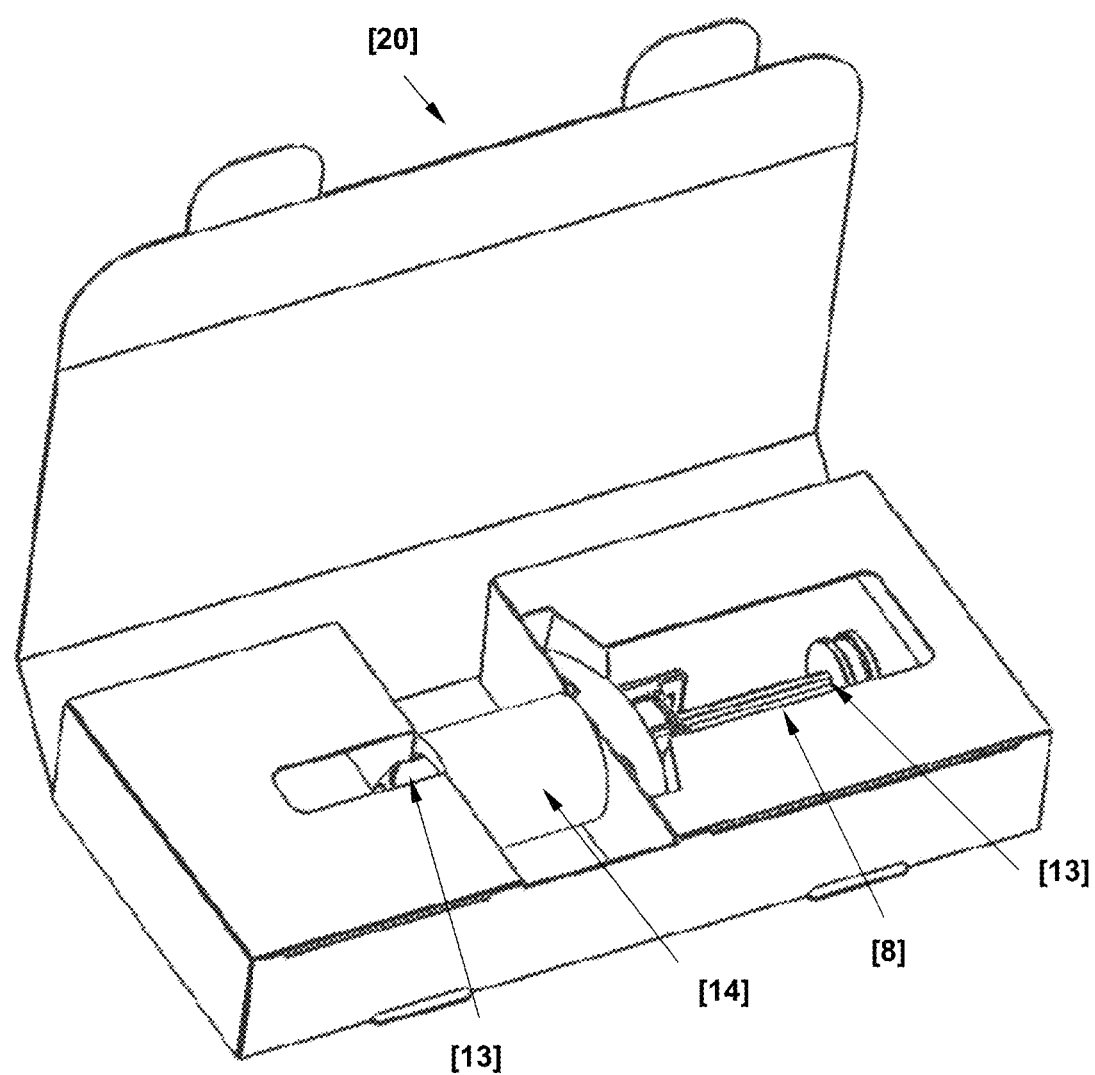

FIG. 20. Packaging for the delivery device

4 DETAILED DESCRIPTION

4.1 Treatment of Cardiometabolic Disease

The invention relates to a method of treating or reducing the risk for development of a cardiometabolic disease in a patient in need thereof, the method comprising administering to the patient a therapeutically effective amount of an inhibitor of type I IFN signalling, wherein the patient has a type I IFN mediated disease.

Pre-treatment with the inhibitor of type I IFN signalling, the patient may have high levels of expression of the one or more cardiometabolic disease markers compared to a healthy subject. Treatment may reduce expression of the one or more cardiometabolic disease markers in the patient from baseline.

The one or more cardiometabolic disease markers may comprise GlycA. The one or more cardiometabolic disease markers may comprise neutrophil extracellular trap (NET). The one or more cardiometabolic disease markers may comprise TNF-α. The one or more cardiometabolic disease markers may comprise IL-10. The one or more cardiometabolic disease markers may comprise GlycA and NET. The one or more cardiometabolic disease markers may comprise GlycA and TNF-α. The one or more cardiometabolic disease markers may comprise GlycA and IL-10. The one or more cardiometabolic disease markers may comprise GlycA, NET and IL-10. The one or more cardiometabolic disease markers may comprise GlycA, NET and TNF-α. The one or more cardiometabolic disease markers may comprise GlycA, NET, TNF-α and IL-10.

Pre-treatment with the inhibitor of type I IFN signalling, the patient may have low levels of expression of the one or more cardiometabolic disease markers compared to a healthy subject. Treatment may increase expression of the one or more cardiometabolic disease markers in the patient from baseline. The one or more cardiometabolic disease markers may comprise cholesterol efflux capacity (CEC).

Pre-treatment the patient may be identified as having a risk of development of a cardiometabolic disease. The method may comprise determining in a sample from the patient the amount of one or more markers, and identifying the patient as having a risk for development of a cardiometabolic disease when the amount of marker is elevated in the patient compared to the amount of the marker in a sample from a healthy subject, wherein the marker is selected from the group consisting of GlycA, TNF-α, IL-10 and combinations thereof. The sample from the patient may comprise blood, plasma, serum, or tissue. GlycA in the sample from the patient may be measured by nuclear magnetic resonance (NMR).

Pre-treatment with the inhibitor of type I IFN signalling the patient may have elevated serum protein levels of IFN-α compared to a healthy subject, wherein the inhibitor of type I IFN signalling decreases the serum protein levels of IFN-α in the patient from baseline.

The method of any preceding claim, wherein the cardiometabolic disease is a cardiovascular disease, optionally wherein the cardiovascular disease is myocarditis, arrhythmia, valvular dysfunction, vasculitis, aortitis, atherosclerosis and/or coronary vasculitis. The cardiometabolic disease may be premature atherosclerosis. the premature atherosclerosis may be sub-clinical. The type I IFN mediated disease may be systemic lupus erythematosus (SLE). The patient may have moderate to severe SLE.

The invention also relates to a pharmaceutical composition for use in any of the methods of the invention, wherein the pharmaceutical composition comprises the inhibitor of type I IFN signalling.

As utilized in accordance with the present disclosure, unless otherwise indicated, all technical and scientific terms shall be understood to have the same meaning as commonly understood by one of ordinary skill in the art. Unless otherwise required by context, singular terms shall include pluralities and plural terms shall include the singular.

In some embodiments, the disclosure provides a method for reducing the risk for development of a cardiometabolic disease in a patient having a risk for development of a cardiometabolic disease, comprising administering a type I interferon receptor inhibitor to the patient, wherein the patient is identified as having a risk for development of a cardiometabolic disease by: determining in a sample from the patient the amount of a marker, wherein the marker is glycoprotein acetylation; and identifying the patient as having a risk for development of a cardiometabolic disease when the amount of glycoprotein acetylation is increased compared to the patient's baseline level.

In some embodiments, treatment administered to the patient results in a change in expression of a cardiometabolic disease marker from the patient's baseline level. In some embodiments, the treatment results in reduced expression of glycoprotein acetylation from the patient's baseline level.

In some embodiments, treatment administered to the patient results in a reduction in immune mediators of endothelial dysfunction from the patient's baseline level. In certain embodiments, the immune mediator is one or more of TNF-α and IL-10.

4.2 Inhibitor of Type I IFN Signalling

The inhibitor of type I IFN signalling may be a type I IFN receptor inhibitor (IFNAR1). An inhibitor of type I IFN signalling may reduce the IFN-α protein levels in the plasma of a patient having an elevated serum protein levels of IFN-α.

A "type I interferon receptor inhibitor" refers to a molecule that is antagonistic for the receptor of type I interferon ligands such as interferon-α and interferon-β. Such inhibitors, subsequent to administration to a patient, preferably provide a reduction in the expression of at least 1 (preferably at least 4) pharmacodynamic (PD) marker genes selected from the group consisting of IFI6, RSAD2, IFI44, IFI44L, IFI27, MX1, IFIT1, HERC5, ISG15, LAMP3, OAS3, OAS1, EPST1, IFIT3, LY6E, OAS2, PLSCR1, SIGLECI, USP18, RTP4, and DNAPTP6. The at least 4 genes may suitably be IFI27, IFI44, IFI44L, and RSAD2. The "type I interferon receptor" is optionally interferon-α/β receptor (IFNAR).

In one embodiment, the type I interferon receptor inhibitor is a type I interferon receptor-blocking antibody. In one such embodiment, the type I interferon receptor-blocking antibody is anifrolumab. Anifrolumab is a monoclonal antibody that inhibits binding of type I IFN to IFNAR and inhibits the biologic activity of all type I IFNs. Disclosure related to anifrolumab can be found in U.S. Pat. No. 7,662,381, which is incorporated herein by reference. The clone 11E2 referenced in U.S. Pat. No. 7,662,381 is anifrolumab.

For example, the type I interferon receptor inhibitor may be an antibody or antigen-binding fragment thereof that inhibits type I IFN activity (by inhibiting the receptor). An example of a suitable antibody or antigen-binding fragment thereof (that inhibits type I IFN activity) is an interferon-α/β receptor (IFNAR) antagonist.

Additionally or alternatively, the type I interferon receptor inhibitor may be a small molecule inhibitor of a type I interferon receptor (e.g. for pharmacological inhibition of type I interferon receptor activity).

The type I interferon receptor inhibitor may be an antibody or antigen-binding fragment thereof that inhibits type I IFN activity. A particularly preferred type I interferon receptor inhibitor is the antibody anifrolumab or a functional variant thereof. Anifrolumab is a monoclonal antibody targeting IFNAR1 (the receptor for α, β, and ω interferons). Disclosure related to anifrolumab can be found in U.S. Pat. Nos. 7,662,381 and 9,988,459, which are incorporated herein by reference.

Thus, in one embodiment the type I interferon receptor inhibitor is anifrolumab or a functional variant thereof.

4.3 Delivery Device

The type I IFN inhibitor may be administered subcutaneously using an accessorized pre-filled syringe (APFS), an autoinjector (AI), or a combination thereof. Such devices have been found to be well-tolerated and reliable for administering subcutaneous doses of an antibody and provide further options for optimizing patient care. Indeed, such devices may reduce the burden of frequent clinic visits for patients. An example of a suitable APFS device is described in Ferguson et. al.[16], which is incorporated herein by reference in its entirety. The delivery device may be single use, disposable system that is designed to enable manual, SC administration of the dose.

The invention also relates to an injection device comprising the pharmaceutical composition of the invention. The injection device may be a pre-filled syringe (PFS). The injection device may be an accessorized pre-filed syringe (AFPS). The injection device may be an auto-injector.

4.4 Kit

The invention also relates to a kit comprising the injection device of the invention and instructions for use. The instructions for use may specify that the injection device and/or pharmaceutical composition are for use in the treatment of SLE. The instructions for use may specify that the injection device and/or pharmaceutical composition are for treating a cardiometabolic disease in a patient. The instructions for use may specific any features of the method of the invention or the pharmaceutical composition of the invention. The kit may comprise packaging, wherein the packaging is adapted to hold the injection device and the instructions for use. The instructions for use may be attached to the injection device.

4.5 Type I IFN Gene Signature (IFNGS)

The patient may have high interferon gene signature expression compared to a healthy subject, or a subject that is not suffering from a type I IFN mediated disease. The type I interferon gene signature may comprise elevated expression of the genes Interferon Alpha Inducible Protein 27 (IFI27), Interferon Induced Protein 44 (IFI44) interferon induced protein 44 like (IFI44L), and Radical S-Adenosyl Methionine Domain Containing 2 (RSAD2), compared to expression levels in a healthy subject, or a subject that is not suffering from a type I IFN mediated disease. The high interferon gene signature expression may be determined by an increased expression of IFI27, IFI44, IFI44L, and RSAD2 relative to expression of one or more control genes.

In some embodiments, the disclosure provides a method of treating a cardiometabolic disease in a patient comprising administering to the patient a therapeutically effective amount of a type I interferon receptor inhibitor, wherein the patient has high interferon gene signature expression.

Direct measurement of type I interferon (IFN) remains a challenge. As such, an IFN gene signature (IFNGS) is used to identify patients with low or high levels of IFN inducible gene expression. In some embodiments, the IFNGS comprises Interferon Alpha Inducible Protein 27 (IFI27), Interferon Induced Protein 44 (IFI44) interferon induced protein 44 like (IFI44L), and Radical S-Adenosyl Methionine Domain Containing 2 (RSAD2). Up regulation or overexpression of the genes comprising the IFNGS can be calculated by well-known methods in the art. For example, the overexpression of the signature is calculated as the difference between the mean Ct (cycle threshold) for IFI27, IFI44, IFI44L, and RSAD2 and the mean Ct of three control genes, 18S, ACTB and GAPDH. The degree of increased expression of the IFNGS permits the identification of a fold change cutoff for identifying IFN-high and IFN-low patients. In one embodiment, the cutoff is at least about 2. In another embodiment, the cutoff is at least about 2.5. In another embodiment, the cutoff is at least about 3. In another embodiment, the cutoff is at least about 3.5. In another embodiment, the cutoff is at least about 4. In another embodiment, the cutoff is at least about 4.5. In another embodiment, the cutoff is chosen from at least 3.5, 3.6, 3.7, 3.8, 3.9, 4.0, 4.1, 4.2, 4.3, 4.4, and 4.5. In another embodiment the cutoff is between about 2 and about 8. The degree of increased expression of the IFNGS also permits the identification of a delta Ct cutoff for identifying IFN-high and IFN-low subpopulations.

Type I IFN is considered to play a central role SLE disease pathogenesis and inhibition of this pathway is targeted by anifrolumab. To understand the relationship between type I IFN expression and response to anti-IFN therapy, it is necessary to know if a subject's disease is driven by type I IFN activation. However, direct measurement of type I IFN remains a challenge. As such, a transcript-based marker was developed to evaluate the effect of over expression of the target protein on a specific set of mRNA markers. The expression of these markers is easily detected in whole blood and demonstrates a correlation with expression in diseased tissue such as skin in SLE. The bimodal distribution of the transcript scores for SLE subjects supports defining an IFN test high and low subpopulation (FIG. 13). The type I IFN test is described in WO2011028933 A1, which is incorporated herein by reference in its entirety. The type I IFN gene signature may be used to identify a subject has a type I IFN gene signature (IFNGS)-test high patient or an IFNGS-test low patient. The IFNGS test measures expression of the genes IFI27, IFI44, IFI44L, and RSAD2 compared with 3 reference genes; 18S, ACTB and GAPDH in the whole blood of the subject. The result of the test is a score that is compared with a preestablished cut-off that classifies patients into 2 groups with low or high levels of IFN inducible gene expression (FIG. 13).

The expression of the genes may be measured by RT-PCR. Suitable primers and probes for detection of the genes may be found in WO2011028933. A suitable kit for measuring gene expression for the IFNGS test is the QIAGEN Therascreen® IFIGx RGQ RT-PCR kit (IFIGx kit), as described in Brohawn et al.[17], which is incorporated herein by reference in its entirety.

4.6 the Patient

The patient may be a human patient. The patient may be an adult. The patient may be a patient with an elevated type I IFN gene signature. The patient may be a type I interferon stimulated gene signature (IFNGS)-test high patient pre-administration with the dose or unit dose. The patient may have elevated of the genes IFI27, IFI44, IFI44L, and RSAD2 in the whole blood. The method may comprise identifying the patient as IFNGS-test high patient pre-treatment with the dose or unit dose. The method may comprise measuring the expression of the genes IFI27, IFI44, IFI44L, and RSAD2 in the whole blood of the patient. The method may comprise measuring the expression of the genes IFI27, IFI44, IFI44L, and RSAD2 in the whole blood of the subject by RT-PCR.

4.7 Formulations

When used for in vivo administration, the formulations of the disclosure should be sterile. The formulations of the disclosure may be sterilized by various sterilization methods, including, for example, sterile filtration or radiation. In one embodiment, the formulation is filter sterilized with a presterilized 0.22-micron filter. Sterile compositions for injection can be formulated according to conventional pharmaceutical practice as described in "Remington: The Science & Practice of Pharmacy," 21st ed., Lippincott Williams & Wilkins (2005).

In some embodiments, antibodies can be formulated for particular routes of administration, such as oral, nasal, pulmonary, topical (including buccal and sublingual), rectal, vaginal, and/or parenteral administration. As used herein, the terms "parenteral administration" and "administered parenterally" refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, and intrasternal injection, and infusion. Formulations of the disclosure that are suitable for topical or transdermal administration include powders, sprays, ointments, pastes, creams, lotions, gels, solutions, patches, and inhalants. The antibodies and other actives may be mixed under sterile conditions with a pharmaceutically acceptable carrier, and with any preservatives, buffers, or propellants which may be required (see, e.g., U.S. Pat. Nos. 7,378,110; 7,258,873; and 7,135,180; U.S. Patent Application Publication Nos. 2004/0042972 and 2004/0042971).

Stable formulations suitable for administration to subjects and comprising anifrolumab are described in detail in U.S. patent Ser. No. 10/125,195 B1, which is incorporated herein in its in entirety.

The Examples that follow are illustrative of specific embodiments of the disclosure, and various uses thereof. They are set forth for explanatory purposes only and should not be construed as limiting the scope of the disclosure in any way.

4.8 Dosage Regimes and Administration Methods

The method may comprise administering intravenously an intravenous dose of anifrolumab or the functional variant thereof to the subject. The intravenous dose may be ≥300 mg anifrolumab or the functional variant thereof. The intravenous dose may be ≤1000 mg. The intravenous dose may be about 300 mg or about 1000 mg. The intravenous dose may be 300 mg to 1000 mg. The intravenous dose may be administered every four weeks (Q4W).

The formulations can be presented in unit dosage form and can be prepared by any method known in the art of pharmacy. Actual dosage levels of the active ingredients in the formulation of the present disclosure may be varied so as to obtain an amount of the active ingredient which is effective to achieve the desired therapeutic response for a particular patient, composition, and mode of administration, without being toxic to the patient (e.g., "a therapeutically effective amount"). Dosages can also be administered via continuous infusion (such as through a pump). The administered dose may also depend on the route of administration. For example, subcutaneous administration may require a higher dosage than intravenous administration.

The dose of the anifrolumab to be administered to the patient will vary depending, in part, upon the size (body weight, body surface, or organ size) and condition (the age and general health) of the patient.

In some embodiments, the patient is administered one or more fixed doses of anifrolumab, wherein the dose is 150 mg, 200 mg, 250 mg, 300 mg, or 350 mg. In some embodiments, the patient is administered one or more fixed doses of anifrolumab wherein the dose is 300 mg.

In some embodiments, anifrolumab is administered over a two-week treatment period, over a four-week treatment period, over a six-week treatment period, over an eight-week treatment period, over a twelve-week treatment period, over a twenty-four-week treatment period, or over a one-year or more treatment period. In some embodiments, anifrolumab is administered over a three-week treatment period, over a six-week treatment period, over a nine-week treatment period, over a twelve-week treatment period, over a twenty-four-week treatment period, or over a one-year or more treatment period. In certain embodiments, anifrolumab is administered for at least 52 weeks.

In some embodiments, anifrolumab is administered every week, every two weeks, every four weeks, every six weeks, every eight weeks, every ten weeks, or every twelve weeks.

5 DEFINITIONS 5.1 Anifrolumab

Anifrolumab is a monoclonal antibody which binds to IFNAR with high affinity and specificity. The antibody is an IFNAR-blocking (antagonistic) antibody, and blocks the activity of the receptor's ligands, namely type I interferons such as interferon-α and interferon-β. Anifrolumab thus provides for downregulation of IFNAR signalling, and thus suppression of IFN-inducible genes.

TABLE 5-1

Anifrolumab sequences

| | |
|---|---|
| Anifrolumab VH (SEQ ID NO: 1) | EVQLVQSGAEVKKPGESLKISCKGSGYIFTNY WIAWVRQMPGKGLESMGIIYPGDSDIRYSPSF QGQVTISADKSITTAYLQWSSLKASDTAMYYC ARHDIEGFDYWGRGTLVTVSS |
| Anifrolumab VL (SEQ ID NO: 2) | EIVLTQSPGTLSLSPGERATLSCRASQSVSSS FFAWYQQKPGQAPRLLIYGASSRATGIPDRLS |

TABLE 5-1-continued

Anifrolumab sequences

| | |
|---|---|
| | GSGSGTDFTLTITRLEPEDFAVYYCQQYDSSA ITFGQGTRLEIK |
| HCDR1 (SEQ ID NO: 3) | NYWIA |
| HCDR2 (SEQ ID NO: 4) | IIYPGDSDIRYSPSFQG |
| HCDR3 (SEQ ID NO: 5) | HDIEGFDY |
| LCDR1 (SEQ ID NO: 6) | RASQSVSSSFFA |
| LCDR2 (SEQ ID NO: 7) | GASSRAT |
| LCDR3 (SEQ ID NO: 8) | QQYDSSAIT |
| Light chain constant region (SEQ ID NO: 9) | RTVAAPSVFIFPPSDEQLKSGTASVVCLLNNF YPREAKVQWKVDNALQSGNSQESVTEQDSKDS TYSLSSTLTLSKADYEKHKVYACEVTHQGLSS PVTKSFNRGEC |
| Heavy chain constant region (SEQ ID NO: 10) | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK RVEPKSCDKTHTCPPCPAPEFEGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPASIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Heavy chain (SEQ ID NO: 11) | EVQLVQSGAEVKKPGESLKISCKGSGYIFTNY WIAWVRQMPGKGLESMGIIYPGDSDIRYSPSF QGQVTISADKSITTAYLQWSSLKASD TAMYY CARHDIEGFDYWGRGTLVTVSSASTKGPSVFP LAPSSKSTSGGTAALGCLVKDYFPEPVTVSWN SGALTSGVHTFPAVLQSSGLYSLSSVVTVPS SSLGTQTYICNVNHKPSNTKVDKRVEPKSCDK THTCPPCPAPEFEGGPSVFLFPPKPKDTLMIS RTPEVTCVVVDVSHEDPEVKFNWYVDGVEVHN AKTKPREEQYNSTYRVVSVLTVLHQDWLNGKE YK CKVSNKALPASIEKTISKAKGQPREPQVY TLPPSREEMTKNQVSLTCLVKGFYPSDIAVEW ESNGQPENNYKTTPPVLDSDGSFFLYSKLTVD KSRWQQGNVFSCSVMHEALHNHYTQKS LSLSPGK |
| Light chain (SEQ ID NO: 12) | EIVLTQSPGTLSLSPGERATLSCRASQSVS S SFFAWYQQKPGQAPRLLIY GASSRATGIPD RLSGSGSGT DFTLTITRLE PEDFAVYYCQQ YDSSAITFG QGTRLEIKRTVAAPSVFIFPPS DEQLKSGT ASVVCLLNNFYPREAKVQWKVDN ALQSGNSQESVTEQDSKDSTYSLSSTLTLSKA DYEKHKVYACEVTHQGLSSPVTKSFNRGEC |

Thus, "anifrolumab" is an antibody comprising an HCDR1, HCDR2 and HCDR3 of SEQ ID NO: 3, SEQ ID NO: 4, and SEQ ID NO: 5, respectively (or functional variant thereof); and an LCDR1, LCDR2 and LCDR3 of SEQ ID NO: 6, SEQ ID NO: 7, and SEQ ID NO: 8, respectively (or functional variant thereof). In more detail, anifrolumab as referred to herein is an antibody comprising a VH of SEQ ID NO: 1 and a VL of SEQ ID NO: 2 (or functional variant thereof).

The constant region of anifrolumab has been modified such that anifrolumab exhibits reduced affinity for at least one Fc ligand compared to an unmodified antibody. Anifrolumab is a modified IgG class monoclonal antibody specific for IFNAR1 comprising in the Fc region an amino acid substitution of L234F, as numbered by the EU index as set forth in Kabat (1991, NIH Publication 91-3242, National Technical Information Service, Springfield, Va.). Anifrolumab is a modified IgG class monoclonal antibody specific for IFNAR1 comprising in the Fc region an amino acid substitution of L234F, L235E and/or P331S, as numbered by the EU index as set forth in Kabat (1991, NIH Publication 91-3242, National Technical Information Service, Springfield, Va.). Anifrolumab is an antibody comprising a light chain constant region of SEQ ID NO: 9. Anifrolumab is an antibody comprising a heavy chain constant region of SEQ ID NO: 10. Anifrolumab is an antibody comprising a light chain constant region of SEQ ID NO: 9 and a heavy chain constant region of SEQ ID NO: 10. Anifrolumab is an antibody comprising a heavy chain of SEQ ID NO: 11. Anifrolumab is an antibody comprising a light chain of SEQ ID NO: 12. Anifrolumab is an antibody comprising a heavy chain of SEQ ID NO: 11 and a light chain of SEQ ID NO: 12.

The present invention encompasses the antibodies defined herein having the recited CDR sequences or variable heavy and variable light chain sequences (reference (anifrolumab) antibodies), as well as functional variants thereof. A "functional variant" binds to the same target antigen as the reference (anifrolumab) antibody. The functional variants may have a different affinity for the target antigen when compared to the reference antibody, but substantially the same affinity is preferred. Functional variants of anifrolumab are sequence variants that perform the same function as anifrolumab. Functional variants of anifrolumab are variants that bind the same target as anifrolumab and have the same effector function as anifrolumab. Functional anifrolumab variants include antigen-binding fragments of anifrolumab and antibody and immunoglobulin derivatives of anifrolumab. Functional variants include biosimilars and interchangeable products. The terms biosimilar and interchangeable product are defined by the FDA and EMA. The term biosimilar refers to a biological product that is highly similar to an approved (e.g. FDA approved) biological product (reference product, e.g. anifrolumab) in terms of structure and has no clinically meaningful differences in terms of pharmacokinetics, safety and efficacy from the reference product. The presence of clinically meaningful differences of a biosimilar may be assessed in human pharmacokinetic (exposure) and pharmacodynamic (response) studies and an assessment of clinical immunogenicity. An interchangeable product is a biosimilar that is expected to produce the same clinical result as the reference product in any given patient.

Functional variants of a reference (anifrolumab) antibody may show sequence variation at one or more CDRs when compared to corresponding reference CDR sequences. Thus, a functional antibody variant may comprise a functional variant of a CDR. Where the term "functional variant" is used in the context of a CDR sequence, this means that the CDR has at most 2, preferably at most 1 amino acid differences when compared to a corresponding reference CDR sequence, and when combined with the remaining 5 CDRs (or variants thereof) enables the variant antibody to bind to the same target antigen as the reference (anifrolumab) antibody, and preferably to exhibit the same affinity for the target antigen as the reference (anifrolumab) antibody.

Without wishing to be bound by theory, since anifrolumab targets (e.g. blocks or antagonizes) IFNAR, it is believed that anifrolumab treats a disease (such as lupus nephritis) by blocking signalling initiated by type I interferons (IFNs). Type I IFNs are known to be important drivers of inflammation (e.g. by coordinating the type I interferon response), and thus play a pivotal role in the immune system. However, dysregulation of type I IFN-signalling can lead to aberrant (e.g. aberrantly high) levels of inflammation, and autoimmunity. Such dysregulation of type I IFN interferons has been reported in numerous autoimmune diseases.

A variant of the reference (anifrolumab) antibody may comprise: a heavy chain CDR1 having at most 2 amino acid differences when compared to SEQ ID NO: 3; a heavy chain CDR2 having at most 2 amino acid differences when compared to SEQ ID NO: 4; a heavy chain CDR3 having at most 2 amino acid differences when compared to SEQ ID NO: 5; a light chain CDR1 having at most 2 amino acid differences when compared to SEQ ID NO: 6; a light chain CDR2 having at most 2 amino acid differences when compared to SEQ ID NO: 7; and a light chain CDR3 having at most 2 amino acid differences when compared to SEQ ID NO: 8; wherein the variant antibody binds to the target of anifrolumab (e.g. IFNAR) and preferably with the same affinity.

A variant of the reference (anifrolumab) antibody may comprise: a heavy chain CDR1 having at most 1 amino acid difference when compared to SEQ ID NO: 3; a heavy chain CDR2 having at most 1 amino acid difference when compared to SEQ ID NO: 4; a heavy chain CDR3 having at most 1 amino acid difference when compared to SEQ ID NO: 5; a light chain CDR1 having at most 1 amino acid differences when compared to SEQ ID NO: 6; a light chain CDR2 having at most 1 amino acid difference when compared to SEQ ID NO: 7; and a light chain CDR3 having at most 1 amino acid difference when compared to SEQ ID NO: 8; wherein the variant antibody binds to the target of anifrolumab (e.g. IFNAR) optionally with the same affinity.

A variant antibody may have at most 5, 4 or 3 amino acid differences total in the CDRs thereof when compared to a corresponding reference (anifrolumab) antibody, with the proviso that there is at most 2 (optionally at most 1) amino acid differences per CDR. A variant antibody may have at most 2 (optionally at most 1) amino acid differences total in the CDRs thereof when compared to a corresponding reference (anifrolumab) antibody, with the proviso that there is at most 2 amino acid differences per CDR. A variant antibody may have at most 2 (optionally at most 1) amino acid differences total in the CDRs thereof when compared to a corresponding reference (anifrolumab) antibody, with the proviso that there is at most 1 amino acid difference per CDR.

The amino acid difference may be an amino acid substitution, insertion or deletion. The amino acid difference may be a conservative amino acid substitution as described herein.

A variant antibody may have at most 5, 4 or 3 amino acid differences total in the framework regions thereof when compared to a corresponding reference (anifrolumab) antibody, with the proviso that there is at most 2 (optionally at most 1) amino acid differences per framework region. Optionally a variant antibody has at most 2 (optionally at most 1) amino acid differences total in the framework regions thereof when compared to a corresponding reference (anifrolumab) antibody, with the proviso that there is at most 2 amino acid differences per framework region. Optionally a variant antibody has at most 2 (optionally at most 1) amino acid differences total in the framework regions thereof when compared to a corresponding reference (anifrolumab) antibody, with the proviso that there is at most 1 amino acid difference per framework region.

Thus, a variant antibody may comprise a variable heavy chain and a variable light chain as described herein, wherein: the heavy chain has at most 14 amino acid differences (at most 2 amino acid differences in each CDR and at most 2 amino acid differences in each framework region) when compared to a heavy chain sequence herein; and the light chain has at most 14 amino acid differences (at most 2 amino acid differences in each CDR and at most 2 amino acid differences in each framework region) when compared to a light chain sequence herein; wherein the variant antibody binds to the same target antigen as the reference (anifrolumab) antibody (e.g. IFNAR) and preferably with the same affinity.

The variant heavy or light chains may be referred to as "functional equivalents" of the reference heavy or light chains. A variant antibody may comprise a variable heavy chain and a variable light chain as described herein, wherein: the heavy chain has at most 7 amino acid differences (at most 1 amino acid difference in each CDR and at most 1 amino acid difference in each framework region) when compared to a heavy chain sequence herein; and the light chain has at most 7 amino acid differences (at most 1 amino acid difference in each CDR and at most 1 amino acid difference in each framework region) when compared to a light chain sequence herein; wherein the variant antibody binds to the same target antigen as the reference (anifrolumab) antibody (e.g. IFNAR) and preferably with the same affinity.

The term "anifrolumab" preferably encompasses an antigen binding fragment thereof. The term "antigen-binding fragment", refers to one or more fragments of anifrolumab that retain(s) the ability to specifically bind to the antigen for anifrolumab (IFNAR). Examples of antigen-binding fragments include the following: Fab fragment, F(ab')2 fragment, Fd fragment, Fv fragment, dAb fragment, as well as a scFv.

5.2 Cardiometabolic Disease

As used herein, a "cardiometabolic disease" refers to a disease of the cardiac and/or metabolic systems. In some embodiments, the cardiometabolic disease is cardiovascular disease, atherosclerosis. vasculopathy, insulin resistance, impaired glucose tolerance, dyslipidemia, hypertension, or central adiposity.

As used herein, "baseline level" refers to the level in the patient pre-treatment or before treatment.

5.3 Clinical Trials 5.3.1 Phase 2/Phase II/Pivotal Studies

Phase II studies gather preliminary data on effectiveness. In Phase 2 studies, researchers administer the drug to a group of patients with the disease or condition for which the drug is being developed. Typically involving a few hundred patients, these studies aren't large enough to show whether the drug will be beneficial. Instead, Phase 2 studies provide researchers with additional safety data. Researchers use these data to refine research questions, develop research methods, and design new Phase 3 research protocols.

5.3.2 Phase 3/Phase III/Pivotal Studies or Trials

Researchers design Phase 3 studies to demonstrate whether or not a product offers a treatment benefit to a specific population. Sometimes known as pivotal studies, these studies involve 300 to 3,000 participants. Phase 3 studies provide most of the safety data. In previous studies, it is possible that less common side effects might have gone undetected. Because these studies are larger and longer in duration, the results are more likely to show long-term or rare side effects. Regulatory bodies such as the EMA and FDA usually require a phase III clinical trial demonstrating that the product is safe and at least as effective (if not better) than available medications, before approving a new medication. Phase III clinical trials usually fail, even if they follow a successful a phase II clinical trial.

5.4 End Points 5.4.1 BILAG-2004 (British Isles Lupus Assessment Group-2004)

The BILAG-2004 is a translational index with 9 organ systems (General, Mucocutaneous, Neuropsychiatric, Musculoskeletal, Cardiorespiratory, Gastrointestinal, Ophthalmic, Renal and Haematology) that is able to capture changing severity of clinical manifestations (FIG. 1). It has ordinal scales by design and does not have a global score, rather it records disease activity across the different organ systems at a glance by comparing the immediate past 4 weeks to the 4 weeks preceding them. It is based on the principle of physicians' intention to treat and categorises disease activity into 5 different levels from A to E:

Grade A represents very active disease requiring immunosuppressive drugs and/or a prednisone dose of >20 mg/day or equivalent Grade B represents moderate disease activity requiring a lower dose of corticosteroids, topical steroids, topical immunosuppressives, antimalarials, or NSAIDs Grade C indicates mild stable disease Grade D implies no disease activity but the system has previously been affected Grade E indicates no current or previous disease activity Although the BILAG-2004 was developed based on the principle of intention to treat, the treatment has no bearing on the scoring index. Only the presence of active manifestations influences the scoring.

In the Cardio-respiratory domain score, the BILAG-2004 Index records myocarditis—mild myocarditis/endocarditis+ cardiac failure; arrhythmia; new valvular dysfunction, pleurisy/pericarditis, cardiac tamponade, pleural effusion with dyspnoea, pulmonary haemorrhage/vasculitis, interstitial alveolitis/pneumonitis, shrinking lung syndrome, aortitis and coronary vasculitis (FIG. 1), as defined in Table 5-2.

TABLE 5-2

BILAG-2004 Cardiorespiratory organ domain

| | |
|---|---|
| Mild myocarditis | inflammation of myocardium with raised cardiac enzymes &/or ECG changes and without resulting cardiac failure, arrhythmia or valvular dysfunction |
| Cardiac failure | cardiac failure due to myocarditis or non-infective inflammation of endocardium or cardiac valves (endocarditis) cardiac failure due to myocarditis is defined by left ventricular ejection fraction ≤40% & pulmonary oedema or peripheral oedema cardiac failure due to acute valvular regurgitation (from endocarditis) can be associated with normal left ventricular ejection fraction diastolic heart failure is not included |
| Arrhythmia | arrhythmia (except sinus tachycardia) due to myocarditis or non-infective inflammation of endocardium or cardiac valves (endocarditis) confirmation by electrocardiogram required (history of palpitations alone inadequate) |
| New valvular dysfunction | new cardiac valvular dysfunction due to myocarditis or non-infective inflammation of endocardium or cardiac valves (endocarditis) supportive imaging required |
| Pleurisy/Pericarditis | convincing history &/or physical findings that you would consider treating in absence of cardiac tamponade or pleural effusion with dyspnoea do not score if you are unsure whether or not it is pleurisy/pericarditis |
| Cardiac tamponade | supportive imaging required |
| Pleural effusion with dyspnoea | supportive imaging required |
| Pulmonary haemorrhage/vasculitis | inflammation of pulmonary vasculature with haemoptysis &/or dyspnoea &/or pulmonary hypertension |
| Interstitial alveolitis/pneumonitis | radiological features of alveolar infiltration not due to infection or haemorrhage required for diagnosis corrected gas transfer Kco reduced to <70% normal or fall of >20% if previously abnormal on-going activity would be determined by clinical findings and lung function tests, and repeated imaging may be required in those with deterioration (clinically or lung function tests) or failure to respond to therapy |
| Shrinking lung syndrome | acute reduction (>20% if previous measurement available) in lung volumes (to <70% predicted) in the presence of normal corrected gas transfer (Kco) & dysfunctional diaphragmatic movements |
| Aortitis | inflammation of aorta (with or without dissection) with supportive imaging abnormalities accompanied by >10 mm Hg difference in BP between arms &/or claudication of extremities &/or vascular bruits repeated imaging would be required to determine on-going activity in those with clinical deterioration or failure to respond to therapy |
| Coronary vasculitis | inflammation of coronary vessels with radiographic evidence of non-atheromatous narrowing, obstruction or aneurysmal changes |

5.4.2 BICLA (BILAG-Based Composite Lupus Assessment)

BICLA is a composite index that was originally derived by expert consensus of disease activity indices. BICLA response is defined as (1) at least one gradation of improvement in baseline BILAG scores in all body systems with moderate or severe disease activity at entry (e.g., all A (severe disease) scores falling to B (moderate), C (mild), or D (no activity) and all B scores falling to C or D); (2) no new BILAG A or more than one new BILAG B scores; (3) no worsening of total SLEDAI score from baseline; (4) no significant deterioration (≤10%) in physicians global assessment; and (5) no treatment failure (initiation of non-protocol treatment).

Particularly, a subject is a BICLA responder if the following criteria are met:
   a) Reduction of all baseline BILAG-2004 A to B/C/D and baseline BILAG-2004 B to C/D, and no BILAG-2004 worsening in other organ systems, as defined by 1 new BILAG-2004 A or more than 1 new BILAG-2004 B item;
   b) No worsening from baseline in SLEDAI-2K as defined as an increase from baseline of >0 points in SLEDAI-2K;
   c) No worsening from baseline in the subjects' lupus disease activity defined by an increase≥0.30 points on a 3-point PGA VAS;
   d) No discontinuation of investigational product or use of restricted medications beyond the protocol-allowed threshold before assessment

5.4.3 CLASI (Cutaneous Lupus Erythematosus Disease Area and Severity Index)

The CLASI is a validated index used for assessing the cutaneous lesions of SLE and consists of 2 separate scores: the first summarizes the inflammatory activity of the disease; the second is a measure of the damage done by the disease. The activity score takes into account erythema, scale/hypertrophy, mucous membrane lesions, recent hair loss, and nonscarring alopecia. The damage score represents dyspigmentation, scarring/atrophy/panniculitis, and scarring of the scalp. Subjects are asked if their dyspigmentation lasted 12 months or longer, in which case the dyspigmentation score is doubled. Each of the above parameters is measured in 13 different anatomical locations, included specifically because they are most often involved in cutaneous lupus erythematosus (CLE). The most severe lesion in each area is measured.

5.4.4 SRI (Systemic Lupus Erythematosus Responder Index of ≥4)

A subject achieves SRI(4) if all of the following criteria are met:
   Reduction from baseline of ≥4 points in the SLEDAI-2K;
   No new organ system affected as defined by 1 or more BILAG-2004 A or 2 or more BILAG-2004 B items compared to baseline using BILAG-2004;
   No worsening from baseline in the subjects' lupus disease activity defined by an increase≥0.30 points on a 3-point PGA VAS.

SRI(X) (X=5, 6, 7, or 8) is defined by the proportion of subjects who meet the following criteria:
   Reduction from baseline of ≥X points in the SLEDAI-2K;
   No new organ systems affected as defined by 1 or more BILAG-2004 A or 2 or more BILAG-2004 B items compared to baseline using BILAG-2004;
   No worsening from baseline in the subjects' lupus disease activity defined by an increase≥0.30 points on a 3-point PGA VAS

5.4.5 SLEDAI-2K (Systemic Lupus Erythematosus Disease Activity Index 2000)

The SLEDAI-2K disease activity index consists of a list of organ manifestations, each with a definition. A certified Investigator or designated physician will complete the SLE-DAI-2K assessment and decide whether each manifestation is "present" or "absent" in the last 4 weeks. The assessment also includes the collection of blood and urine for assessment of the laboratory categories of the SLEDAI-2K.

The SLEDAI-2K assessment consists of 24 lupus-related items. It is a weighted instrument, in which descriptors are multiplied by a particular organ's "weight". For example, renal descriptors are multiplied by 4 and central nervous descriptors by 8 and these weighted organ manifestations are totaled into the final score. The SLEDAI-2K score range is 0 to 105 points with 0 indicating inactive disease. The SLEDAI-2K scores are valid, reliable, and sensitive clinical assessments of lupus disease activity. The SLEDAI-2K calculated using a timeframe of 30 days prior to a visit for clinical and laboratory values has been shown to be similar to the SLEDAI-2K with a 10-day window[18].

5.5 Treatment

As used herein, the terms "treatment" or "treat" refer to both therapeutic treatment and prophylactic or preventative measures. Those in need of treatment include patients having a cardiometabolic disease as well as those prone to having cardiometabolic disease or those in which cardiometabolic disease is to be prevented. In some embodiments, the methods disclosed herein can be used to treat cardiometabolic disease. The present disclosure may be applied to other diseases in addition to cardiometabolic diseases such as diseases affiliated with cardiometabolic diseases.

5.6 Administration

As used herein, the terms "administration" or "administering" refer to providing, contacting, and/or delivering a compound or compounds by any appropriate route to achieve the desired effect. Administration may include, but is not limited to, oral, sublingual, parenteral (e.g., intravenous, subcutaneous, intracutaneous, intramuscular, intraarticular, intraarterial, intrasynovial, intrasternal, intrathecal, intralesional, or intracranial injection), transdermal, topical, buccal, rectal, vaginal, nasal, ophthalmic, via inhalation, and implants.

5.7 Biomarkers

5.7.1 Cholesterol Efflux Capacity (CEC)

Cholesterol efflux capacity (CEC) measures the ability of an individual's HDL to promote cholesterol efflux from cholesterol donor cells such as macrophages. Impaired CEC promotes accumulation of lipid-laden macrophages in atherosclerotic lesions, which secrete pro-inflammatory cytokines and are a hallmark of atherosclerosis. In some embodiments, treatment administered to the patient results in an increase in cholesterol efflux capacity from the patient's baseline level.

5.7.2 Neutrophils Release Neutrophil Extracellular Traps (NETs)

Neutrophils release neutrophil extracellular traps (NETs) in a cell death-associated process, and this phenomenon has proatherogenic effects. Immune complexes containing NET autoantigens induce plasmacytoid dendritic cells and other innate immune cells to aberrantly enhance type I IFN synthesis. In some embodiments, treatment administered to the patient results in a reduction in neutrophil extracellular trap formation from the patient's baseline level.

5.7.3 Glycoprotein Acetylation (GlycA)

Glycoprotein Acetylation (GlycA) is a biomarker of systemic inflammation. GlycA is associated with incident cardiovascular disease (CVD)[19,20], particularly atherosclerosis[21,22], and cardiometabolic (CM) disease[23]. GlycA is a nuclear magnetic resonance (NMR) signal, measured in the blood serum or plasma, and reflects mainly the glycosylation of acute-phase proteins a1-acid glycoprotein, haptoglobin, α1antitrypsin, α1antichymotrypsin and transferrin[22].

5.8 Steroids

Steroids, particularly oral corticosteroids (OCS, glucocorticoids) include prednisone, cortisone, hydrocortisone, methylprednisolone, prednisolone and triamcinolone. Examples of equivalent doses of oral prednisone are shown in Table 5-3.

TABLE 5-3

Examples of equivalent doses of oral prednisone

| | Oral Prednisone and Equivalents Equivalent Dose | | | | |
|---|---|---|---|---|---|
| Oral Prednisone | 7.5 mg | 10 mg | 20 mg | 30 mg | 40 mg |
| Cortisone | 37.5 mg | 50 mg | 100 mg | 150 mg | 200 mg |
| Hydrocortisone | 30 mg | 40 mg | 80 mg | 120 mg | 160 mg |
| Methylprednisolone | 6 mg | 8 mg | 16 mg | 24 mg | 32 mg |
| Prednisolone | 7.5 mg | 10 mg | 20 mg | 30 mg | 40 mg |
| Triamcinolone | 6 mg | 8 mg | 16 mg | 24 mg | 32 mg |

The Examples that follow are illustrative of specific embodiments of the disclosure, and various uses thereof. They are set forth for explanatory purposes only and should not be construed as limiting the scope of the disclosure in any way.

6 EXAMPLE 1: ANIFROLUMAB IN THE CLINIC

Anifrolumab safety has been evaluated in 8 blinded or open-label intravenous (IV) and subcutaneous (SC) studies: 6 studies in patients with SLE (Study 05, Study 04, Study 1013, Study 1145, and Study 08), 1 study in patients with systemic sclerosis (SSc) (Study MI-CP180), and 1 study in healthy volunteers (Study 06) (Table 6-1). Of these studies, two (Studies 08 and 06) employed SC anifrolumab administration. Two studies are ongoing: 1 study in patients with SLE (Study 09) and 1 study in patients with lupus nephritis (LN) (Study 07).

TABLE 6-1

Anifrolumab clinical studies

| | | Subjects | Admin. | Anifro Dose | CT.gov |
|---|---|---|---|---|---|
| Phase III studies | | | | | |
| Study 05 | TULIP II | SLE patients | IV | 300 mg Q4W | NCT02446899 |
| Study 04 | TULIP I | SLE patients | IV | 300 mg Q4W | NCT02962960 |
| Study 09 | Long-term extension | SLE patients | IV | 300 mg | |
| Phase II studies | | | | | |
| Study 1013 | MUSE | SLE patients | IV | 300 mg or 1000 mg Q4W | NCT01438489 |
| Study 1145 | MUSE OLE | | IV | 300 mg | NCT01753193 |
| Study 08 | | SLE patients | SC | | NCT02962960 |
| Study 07 | | LN patients | | | NCT02547922 |
| Phase I | | | | | |
| Study MI-CP180 | | Scleroderma patients | IV | | |
| Study 06[24] | | Healthy volunteers | IV and SC | 300 mg, SC, 300 mg IV or 600 mg SC | NCT02601625 |

Study 1013 is described in further detail in Furie et al. 2017[25], which is incorporated herein by reference in its entirety. Study 04 is described in further detail in Furie et al. 2019[26], which is incorporated herein by reference in its entirety. The results of Study 05 are presented in Morand et al. 2020[27], herein incorporated by reference in its entirety. A full summary of the evidence for intravenous anifrolumab clinical efficacy in SLE is provided in Tanaka et al., 2020[28], which is incorporated herein by reference in its entirety.

7 EXAMPLE 2: MODULATION OF CARDIOMETABOLIC DISEASE MARKERS BY INHIBITION OF TYPE I IFN SIGNALLING IN SLE

7.1 Introduction

The inventors evaluated the ability of anifrolumab, a type I IFN receptor-blocking antibody, to reduce neutrophil extracellular trap (NET) formation and modulate cardiometabolic disease markers in comparison to placebo.

7.2 Materials and Methods

7.2.1 Patients and Sample Collection

Blood samples were obtained from adults aged 18-65 years with moderate to severe systemic lupus erythematosus (SLE) as assessed by SLE Disease Activity Index 2000 (SLEDAI-2K), enrolled in the phase 2b MUSE randomized, double-blind study (NCT01438489)[29]. Patients were randomized 1:1:1 to receive intravenous infusions of anifrolumab 300 mg (n=99), anifrolumab 1,000 mg (n=104), or placebo (n=102) every 4 weeks alongside standard therapy, with the final dose administered at 48 weeks. Plasma/sera from fasting patients were collected at days 0, 169, and 365 of the MUSE study. Interferon gene signature (IFNGS) test status was measured prior to randomization, and oral corticosteroid tapering was allowed after randomization (Furie et al., 2017). Details on the inclusion and exclusion criteria and patient demographics for the MUSE trial have been published (Furie et al., 2017).

7.2.2 Measurement of Neutrophil Number

Blood samples from patients were collected pre-dose on day 1, and neutrophil number was derived from complete blood count with differential, performed using validated methods (Casey et al., Lupus Sci. Med. 5(1): e000286 (2018)).

7.2.3 IFN Target Gene Expression

For the IFNGS test an analytically validated four-gene (IFI27, IFI44, IFI44L, and RSAD2) IFNGS test was conducted in whole blood by quantitative polymerase chain reaction (qPCR) as previously published (Furie et al., 2017) to determine IFNGS test status. Patients were segregated into IFNGS test-high and IFNGS test-low categories at baseline using a predetermined $\Delta$Ct-based cutoff point in the trough of the bimodal distribution (FIG. 13).

The 21-IFNGS was generated using a 21-gene qPCR assay to measure the extent of type I interferon (IFN) signaling dysregulation in patients with SLE as previously described (Yao et al., Hum. Genomics Proteomics pii: 374312 (2009)).

7.2.4 Measurement of Neutrophil Extracellular Trap (NET) Complexes

NET remnants in patient sera were quantified using capture enzyme-linked immunosorbent assays (ELISAs) that detect complexes of myeloperoxidase (MPO)-DNA, neutrophil elastase (NE)-DNA, or citrullinated histone H3(CitH3)-DNA, as published previously (Lood et al., Nat. Med. 22(2): 146-53 (2016)). For detection of MPO-DNA, high-binding, 96-well ELISA plates were incubated overnight with a mouse anti-human MPO antibody (clone 4A4; AbD Serotec) at 4° C. in Cell Death Detection kit (Roche) coating buffer. Nonspecific binding sites were blocked in 1% bovine serum albumin, and plasma samples diluted in blocking buffer were incubated overnight at 4° C. After washing, anti-DNA-peroxidase (Roche) detection antibody was incubated for 1.5 hours at room temperature. 3,3',5,5'-Tetramethylbenzidine substrate (Sigma) was added, before stopping reagent (Sigma), and absorbance was measured at 450 nm. Similarly, NE-DNA and CitH3-DNA were detected using rabbit anti-human NE (Calbiochem) or rabbit anti-human CitH3 (Abcam ab5103) capture antibodies, respectively, followed by 1 hour incubations with the monoclonal mouse anti-double-stranded DNA primary antibody (Millipore) and anti-mouse immunoglobulin G horseradish peroxidase (Bio-Rad) secondary antibody.

7.2.5 LDG Gene Signature Analysis

PAXgene whole-blood RNA tubes were stored at −80° C. prior to shipment for RNA sequencing (Covance Genomics Laboratory). After RNA extraction using standard RNA preparation procedures, samples with an RNA integrity number score>5.0, as measured using an Agilent Bioanalyzer, were selected for downstream application. Globin messenger RNA (mRNA) was depleted using a GLOBIN-clear™ kit (Ambion) prior to mRNA selection and library preparation using the Illumina TruSeq Stranded mRNA kit. High-throughput sequencing was performed using an Illumina HiSeq 4000. Sequence-read qualities were assessed by FastQC and adapter primers were trimmed with Trimmomatic v0.32 (Bolger et al., Bioinformatics 30(15): 2114-20 (2014)). Paired-end reads were mapped to human genome GRCh38 using STAR 2.5 (Dobin et al., Bioinformatics 29(1): 15-21 (2013)) and read numbers were counted using HTSeq-count-0.6.1 (Anders et al., Bioinformatics 31(2): 166-69 (2015)). Genes were included for assessment if they had >50 mapped reads across all included samples. Differentially expressed genes were selected by DESeq2 (Love et al., Genome Biol. 15: 550 (2014)), which was also used alongside custom scripts to calculate fragments per kilobase exon per million fragments mapped. A composite LDG gene signature was calculated as a Z-score from the reads per kilobase million values of AZU1, MPO, CTSG, PRTN3, ELANE, and DEFA3 as previously described[15]. LDG gene signature[30] changes were obtained by comparing matched Z-scores at day 365 with day 1 in patients with Z-score>median Z-score at baseline.

7.2.6 Serum Protein Measurements

Serum samples were stored at −80° C. before shipment to Myriad RBM (Austin, TX, USA). Serum IFN-$\alpha$, IFN-$\beta$, IFN-$\gamma$, IL-10, and tumour necrosis factor alpha (TNF-$\alpha$) were quantified using a Simoa™ immunoassay (Myriad RBM, Ultrasensitive Immunoassays developed by Myriad RBM based on the Simoa™ technology, 2018 (available from myriadrbm.com/products-services/ultrasensitive-immunoassays). All other serum proteins were measured using Luminex quantitative immunoassay according to standard procedures.

7.2.7 Measurement of Cholesterol Efflux Capacity (CEC)

High-density lipoprotein (HDL) CEC assays were performed based on published methods using J774 cells derived from a murine macrophage cell line (Mehta et al., Atherosclerosis 224(1): 218-21 (2012)). Briefly, 3×105 J774 cells/well were plated and radiolabeled with 2 μCi of 3H-cholesterol/mL. ATP-binding cassette transporter A1 was upregulated by means of a 16-hour incubation with 0.3 mM of 8-(4-chlorophenylthio)-cAMP. Apolipoprotein B (ApoB)-depleted plasma (2.8%) was added to the efflux medium for 4 hours. Liquid scintillation counting was used to quantify the efflux of radioactive cholesterol from the cells. Efflux was calculated using the following formula: (µCi of 3H-cholesterol in media containing 2.8% apoB-depleted subject plasma—µCi of 3H-cholesterol in plasma-free media/µCi of 3H-cholesterol in media containing 2.8% apoB-depleted pooled control plasma—µCi of 3H-cholesterol in pooled control plasma-free media). A CEC defect was identified based on values that were two standard deviations below the mean CEC in plasma obtained from five healthy adult volunteers (FIG. 7). All assays were performed in duplicate.

7.2.8 GlycA and LipoProfile® Nuclear Magnetic Resonance (NMR) Spectroscopy

As per Otvos et al., Clin. Chem. 61(5): 714-23 (2015), plasma was adjusted to a density of 1.22 g/mL in sodium bromide and centrifuged to separate the lipoprotein and protein fractions (84,000 g, 48 hours at 4° C.). The two fractions were dialyzed against NMR diluent (50 mM sodium phosphate, 120 mM KCl, 5 mM $Na_2EDTA$, 1 mM $CaCl_2$, pH 7.4) and concentration-adjusted before centrifugal passage through a 10-kDa Centricon ultrafilter (Merck Millipore) to yield the desired molecular weight fraction. A standard 0.01-M N-acetylglucosamine sample was prepared in NMR diluent. GlycA and other lipid parameters were measured in plasma by NMR spectroscopy (LabCorp) using the NMR LipoProfile test spectrum (Otvos et al., 2015; LabCorp, GlycA TEST: 123850, 2018, available from labcorp.com/test-menu/26131/glyca). GlycA high and lipid cut-offs were determined as two standard deviations from the median value in healthy donors.

7.2.9 Insulin Resistance

Serum insulin concentrations were determined using an Insulin Human ELISA Kit (Thermo Fisher, #KAQ1251). Serum glucose concentrations were determined via an enzymatic assay as part of a clinical, validated chemistry panel performed by LabCorp (LabCorp, Glucose Test: 001032. 2019; available from www.labcorp.com/test-menu/26026/glucose). Insulin resistance (IR) was calculated from insulin and glucose concentrations using the HOMA2 Calculator (Diabetes Trials Unit, University of Oxford, HOMA2 Calculator; available from www.dtu.ox.ac.uk/homacalculator/).

7.2.10 Statistics

A 2-tailed Mann-Whitney U test was used to analyze CEC, GlycA, IL-10, IR, neutrophil number, NET complexes, and TNF-α in patients with SLE compared with healthy donors and comparison of anifrolumab 300 mg versus placebo. Spearman's rank correlation was used to analyze associations of vascular inflammatory markers, neutrophil number, and NET complexes with 21-IFNGS analyses and IFN-α protein measurements. Welch's t-test for group comparisons was used to analyze associations of vascular inflammatory markers, neutrophil number, and NET complexes with IFNGS test status, SLEDAI score, and Cutaneous Lupus Erythematosus Disease Area and Severity Index (CLASI) score. Signed-rank tests were used to compare changes from baseline in the aforementioned markers after treatment with anifrolumab 300 mg or placebo. RStudio 1.1.383 was used to perform all statistical analyses.

7.3 Results 7.3.1 Association of IFN-α with IFNGS in SLE Patients

Using ultrasensitive immunoassays, the association of serum protein levels of IFN-α and IFN-β with type I IFNGS was analyzed. IFN-α was quantifiable in baseline serum samples in the majority of patients (80.1%, 205/256), including 96.3% (184/191) who were IFNGS test-high and 32.3% (21/65) who were IFNGS test-low (FIG. 2A). In contrast, IFN-β was quantifiable in only 2.0% (5/256) of patients, indicating IFN-α is the dominant type I IFN protein in circulation in lupus.

IFNGS test-high patients had significantly higher serum IFN-α protein concentrations than IFNGS test-low patients (area under the curve (AUC)=0.92, p<0.001). Median IFN-α protein level in IFNGS test-high patients was greater than the maximum level of healthy donors (FIG. 2A). While the 4-gene IFNGS test categorizes patients into two distinct subgroups, a 21-gene IFNGS panel (21-IFNGS) generates a continuous 21-IFNGS score. Serum IFN-α protein levels correlated with whole blood 21-IFNGS in SLE (Spearman's rank correlation [R]=0.81, p<0.001; FIG. 2B), supporting a direct contribution of IFN-α to lupus IFN gene signatures.

Proteins that significantly correlated with both IFN-α protein and the 21-IFNGS included many atherosclerosis- and vascular dysfunction-associated proteins including tumour necrosis factor alpha (TNF-α), interleukin (IL)-10, angiopoietin 2, VCAM-1, MIP-3β, MCP-1, progranulin, IP-10, and von Willebrand factor (Table 7-1).

TABLE 7-1

Serum analytes that correlate with both IFN-α and IFN 21-gene signature expression

| | Analyte[a] | IFN-α | | | | 21-IFNGS | | | |
|---|---|---|---|---|---|---|---|---|---|
| | | N | Rho | P-value | FDR | n | Rho | P-value | FDR |
| IFN and | 21-IFNGS | 255 | 0.82 | <E−14 | <E−14 | NA | NA | NA | NA |
| IFN-Inducible | IFN-α | NA | NA | NA | NA | 255 | 0.82 | <E−14 | <E−14 |
| Cytokines | MCP-2 | 256 | 0.65 | <E−14 | <E−14 | 301 | 0.67 | <E−14 | <E−14 |
| | IP-10 | 256 | 0.63 | <E−14 | <E−14 | 301 | 0.63 | <E−14 | <E−14 |
| | BAFF | 256 | 0.62 | <E−14 | <E−14 | 301 | 0.57 | <E−14 | <E−14 |
| | MIP-3β | 256 | 0.60 | <E−14 | <E−14 | 301 | 0.63 | <E−14 | <E−14 |
| | ITAC | 256 | 0.59 | <E−14 | <E−14 | 301 | 0.56 | <E−14 | <E−14 |
| | BLC | 256 | 0.43 | 3.49E−13 | 2.48E−12 | 301 | 0.43 | 4.44E−15 | 3.61E−14 |
| | MCP-1 | 256 | 0.37 | 7.48E−10 | 4.03E−9 | 301 | 0.34 | 1.54E−9 | 7.93E−9 |
| | Eotaxin 2 | 256 | −0.23 | 1.88E−4 | 6.21E−4 | 301 | −0.21 | 1.84E−4 | 6.10E−4 |
| Vascular | TNF-α | 254 | 0.62 | <E−14 | <E−14 | 253 | 0.61 | <E−14 | <E−14 |
| Damage/ | IL-10 | 254 | 0.55 | <E−14 | <E−14 | 253 | 0.51 | <E−14 | <E−14 |
| Lipid | Angiopoietin 2 | 256 | 0.52 | <E−14 | <E−14 | 301 | 0.47 | <E−14 | <E−14 |
| Dysregulation | VCAM-1 | 256 | 0.49 | <E−14 | <E−14 | 301 | 0.47 | <E−14 | <E−14 |
| | vWF | 255 | 0.32 | 1.42E−7 | 6.35E−7 | 300 | 0.33 | 6.37E−9 | 3.15E−8 |
| | ApoA 1 | 50 | −0.33 | 0.021 | 0.044 | 50 | −0.37 | 0.009 | 0.021 |

TABLE 7-1-continued

Serum analytes that correlate with both IFN-α and IFN 21-gene signature expression

| | Analyte[a] | IFN-α | | | | 21-IFNGS | | | |
|---|---|---|---|---|---|---|---|---|---|
| | | N | Rho | P-value | FDR | n | Rho | P-value | FDR |
| | Medium cHDLP | 50 | −0.34 | 0.015 | 0.032 | 50 | −0.36 | 0.010 | 0.023 |
| | HDLC | 50 | −0.37 | 0.009 | 0.020 | 50 | −0.41 | 0.003 | 0.009 |
| | Total cholesterol | 50 | −0.39 | 0.005 | 0.013 | 50 | −0.39 | 0.005 | 0.012 |
| | H3P | 50 | −0.50 | 2.07E−4 | 6.81E−4 | 50 | −0.46 | 8.69E−4 | 0.003 |
| Neutrophil | Progranulin | 256 | 0.62 | <E−14 | <E−14 | 301 | 0.57 | <E−14 | <E−14 |
| Dysregulation | CitH3-DNA | 185 | 0.23 | 0.001 | 0.004 | 188 | 0.22 | 0.002 | 0.006 |
| | MPO-DNA | 185 | 0.19 | 0.008 | 0.020 | 188 | 0.21 | 0.003 | 0.009 |
| | Neutrophil number | 251 | −0.29 | 2.13E−6 | 8.89E−6 | 296 | −0.18 | 0.002 | 0.005 |
| Immune | B-2 microglobulin | 255 | 0.52 | <E−14 | <E−14 | 300 | 0.52 | <E−14 | <E−14 |
| Dysregulation/ | Ficolin 3 | 256 | 0.45 | 3.02E−14 | 2.28E−13 | 301 | 0.48 | <E−14 | <E−14 |
| Other | IL-2 | 253 | 0.43 | 6.89E−13 | 4.75E−12 | 252 | 0.40 | 2.37E−11 | 1.44E−10 |
| | IFN-γ | 256 | 0.42 | 1.67E−12 | 1.08E−11 | 255 | 0.46 | 1.04E−14 | 8.17E−14 |
| | IgE | 256 | 0.37 | 1.22E−9 | 6.40E−9 | 301 | 0.33 | 6.37E−9 | 3.15E−8 |
| | TRAIL-R3 | 256 | −0.22 | 5.11E−4 | 0.002 | 301 | −0.24 | 2.20E−5 | 8.08E−5 |
| | IL-1R2 | 256 | −0.36 | 4.08E−9 | 2.05E−8 | 301 | −0.29 | 4.09E−7 | 1.80E−6 |
| | Leukocyte number | 251 | −0.41 | 7.62E−12 | 4.79E−11 | 296 | −0.33 | 9.53E−9 | 4.63E−8 |
| | Lymphocyte number | 251 | −0.48 | 1.33E−15 | 1.09E−14 | 296 | −0.49 | <E−14 | <E−14 |

[a]Includes analytes measured with a p-value < 0.05 and an FDR < 0.05. ApoA 1, apolipoprotein A1; BAFF, B-cell-activating factor; BLC, B-cell lymphoma 2; cHDLP, high-density lipoprotein particle count; CitH3, citrullinated histone H3; FDR, false discovery rate; HDLC, high density lipoprotein count; IFN, interferon; IgE, immunoglobulin E; IL-2, interleukin 2; IL-1R2, interleukin 1 receptor type 2; IP-10, interferon gamma-induced protein 10; ITAC, interferon-inducible T-cell alpha chemoattractant; MCP-1, monocyte chemoattractant protein; MIP-3β, macrophage inflammatory protein 3-beta; MPO, myeloperoxidase; Rho, Spearman's rho; TNF, tumor necrosis factor, TRAIL-R3, TNF-related apoptosis-inducing ligand receptor 3; VCAM-1, vascular cell adhesion molecule 1; vWF, von Willebrand factor.

EXAMPLE 2: INHIBITION OF TYPE I IFN SIGNALLING MODULATES NET LEVELS IN SLE

To understand the relationship between type I IFN signalling, neutrophil dysregulation, and associated biology, the correlation of IFN-α protein and the 21-IFNGS was assessed with other analytes in sera (Table 7-2). Whole blood neutrophil numbers negatively correlated with serum IFN-α protein levels (R=−0.29, p<0.001; FIG. 2C) and with 21-IFNGS, while IFNGS test-high patients had significantly fewer neutrophils compared with IFNGS test-low patients. These results support a direct association between neutrophils and multiple measures of type I IFN pathway activity.

Levels of circulating NET complexes (citrullinated histone H3 [CitH3]-, MPO-, and neutrophil elastase [NE]-DNA) were elevated in SLE compared with healthy donors (FIG. 2D) and negatively correlated with neutrophil numbers (Table 7-2). IFNGS test-high patients had significantly elevated CitH3-DNA NET remnants compared with IFNGS test-low patients (p=0.030), and there was a correlation between CitH3-DNA and 21-IFNGS and IFN-α protein (Table 7-2). Similar associations were also observed between assessments of the other NET remnants (MPO-DNA and NE-DNA) and type I IFN measures. Thus, increased circulating NETs in SLE are associated with reduced neutrophil numbers and elevated type I IFN activity.

Statistical correlations of the type I IFN pathway with NETs and neutrophils are shown in FIG. 3. Associations with lupus disease activity are in FIG. 7. Patients with increased SLEDAI scores had significantly decreased CEC, reduced neutrophil numbers, and increased TNF-α compared with patients with lower SLEDAI scores (CEC: p=0.03066; neutrophil number: p=0.000224; TNF-α: p=8.27E-4). Patients with increased CLASI scores also had reduced neutrophil numbers and increased TNF-α compared with patients with lower CLASI scores (neutrophil numbers: p=0.00533; TNF-α: p=0.002). Patients with increased SLE-DAI scores were also significantly older and had increased HDL counts compared with patients who had lower SLE-DAI scores (age: p=6.66E-5; HDL: p=0.0421). There were no significant associations between NET complexes or GlycA with SLE disease activity. Together, these results demonstrate associations of NET complexes with the type I IFN pathway, but not to degree of SLE disease activity.

Given the association between NETs and the type I IFN pathway, NET complexes at days 1 and 365 in patients who received the anti-IFNAR1 antibody anifrolumab or placebo were investigated (FIG. 4). Notably, median NET complex levels were significantly decreased at day 365 in patients receiving anifrolumab. Placebo patients had increased CitH3-DNA levels (but not the other NET complexes) at day 365 (p=0.006). There were no changes in LDG-associated gene signature[15] in patients who received anifrolumab. These results demonstrate that type I IFN pathway inhibition significantly reduced circulating NETs without an apparent reduction in circulating LDGs, although it is possible that the LDG signature may have been diluted by other neutrophils.

TABLE 7-2

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
|---|---|---|---|---|---|
| 21-IFNGS | Lymphocyte count | 296 | −4.944E−01 | <E−14 | <E−14 |
| 21-IFNGS | ANG2 | 301 | 4.667E−01 | <E−14 | <E−14 |
| 21-IFNGS | VCAM1 | 301 | 4.669E−01 | <E−14 | <E−14 |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
| --- | --- | --- | --- | --- | --- |
| 21-IFNGS | Ficolin 3 | 301 | 4.765E-01 | <E-14 | <E-14 |
| 21-IFNGS | IL-10 | 253 | 5.063E-01 | <E-14 | <E-14 |
| 21-IFNGS | B2M | 300 | 5.159E-01 | <E-14 | <E-14 |
| 21-IFNGS | ITAC | 301 | 5.622E-01 | <E-14 | <E-14 |
| 21-IFNGS | Progranulin | 301 | 5.699E-01 | <E-14 | <E-14 |
| 21-IFNGS | BAFF | 301 | 5.700E-01 | <E-14 | <E-14 |
| 21-IFNGS | TNF-α | 253 | 6.089E-01 | <E-14 | <E-14 |
| 21-IFNGS | IP-10 | 301 | 6.266E-01 | <E-14 | <E-14 |
| 21-IFNGS | MIP3-β | 301 | 6.270E-01 | <E-14 | <E-14 |
| 21-IFNGS | MCP2 | 301 | 6.674E-01 | <E-14 | <E-14 |
| 21-IFNGS | IFN-α protein (pg/mL) | 255 | 8.181E-01 | <E-14 | <E-14 |
| 21-IFNGS | BLC | 301 | 4.314E-01 | <E-14 | 3.610E-14 |
| 21-IFNGS | IFN-γ | 255 | 4.592E-01 | 1.044E-14 | 8.170E-14 |
| 21-IFNGS | IL-2 | 252 | 4.047E-01 | 2.368E-11 | 1.440E-10 |
| 21-IFNGS | MCP1 | 301 | 3.392E-01 | 1.539E-09 | 7.930E-09 |
| 21-IFNGS | IgE | 301 | 3.268E-01 | 6.374E-09 | 3.150E-08 |
| 21-IFNGS | von Willebrand factor | 300 | 3.273E-01 | 6.365E-09 | 3.150E-08 |
| 21-IFNGS | Leukocyte count | 296 | -3.258E-01 | 9.527E-09 | 4.630E-08 |
| 21-IFNGS | IL1RII | 301 | -2.870E-01 | 4.092E-07 | 1.800E-06 |
| 21-IFNGS | TRAILR3 | 301 | -2.420E-01 | 2.197E-05 | 8.080E-05 |
| 21-IFNGS | Eotaxin-2 | 301 | -2.140E-01 | 1.836E-04 | 6.100E-04 |
| 21-IFNGS | HDL in the H3P size range (μM) | 50 | -4.562E-01 | 8.692E-04 | 2.608E-03 |
| 21-IFNGS | Neutrophil number | 296 | -1.823E-01 | 1.634E-03 | 4.675E-03 |
| 21-IFNGS | CitH3-DNA | 188 | 2.218E-01 | 2.219E-03 | 6.164E-03 |
| 21-IFNGS | HDLC (mg/dL) | 50 | -4.073E-01 | 3.330E-03 | 8.877E-03 |
| 21-IFNGS | MPO-DNA | 188 | 2.120E-01 | 3.492E-03 | 9.195E-03 |
| 21-IFNGS | NE-DNA | 188 | 2.052E-01 | 4.724E-03 | 1.169E-02 |
| 21-IFNGS | Total cholesterol (mg/dL) | 50 | -3.902E-01 | 5.084E-03 | 1.244E-02 |
| 21-IFNGS | Ferritin | 301 | 1.515E-01 | 8.486E-03 | 1.964E-02 |
| 21-IFNGS | Apolipoprotein A1 (mg/dL) | 50 | -3.655E-01 | 9.044E-03 | 2.062E-02 |
| 21-IFNGS | Medium cHDLP (μM) | 50 | -3.597E-01 | 1.031E-02 | 2.294E-02 |
| 21-IFNGS | cHDLP (μM) | 50 | -2.277E-01 | 1.118E-01 | 1.796E-01 |
| 21-IFNGS | CEC | 129 | -1.211E-01 | 1.716E-01 | 2.620E-01 |
| 21-IFNGS | Medium TRLP (nM) | 50 | 1.813E-01 | 2.077E-01 | 3.079E-01 |
| 21-IFNGS | IR | 121 | 1.063E-01 | 2.458E-01 | 3.504E-01 |
| 21-IFNGS | Very Small TRLP (nM) | 50 | 1.234E-01 | 3.932E-01 | 5.031E-01 |
| 21-IFNGS | GlycA | 50 | -1.005E-01 | 4.875E-01 | 5.924E-01 |
| 21-IFNGS | Very Large TRLP (nM) | 50 | -3.916E-02 | 7.872E-01 | 8.440E-01 |
| IFN-α protein (pg/mL) | ANG2 | 256 | 5.181E-01 | <E-14 | <E-14 |
| IFN-α protein (pg/mL) | B2M | 255 | 5.246E-01 | <E-14 | <E-14 |
| IFN-α protein (pg/mL) | BAFF | 256 | 6.193E-01 | <E-14 | <E-14 |
| IFN-α protein (pg/mL) | Ficolin 3 | 256 | 4.513E-01 | 3.020E-14 | 2.280E-13 |
| IFN-α protein (pg/mL) | BLC | 256 | 4.340E-01 | 3.491E-13 | 2.480E-12 |
| IFN-α protein (pg/mL) | IgE | 256 | 3.682E-01 | 1.219E-09 | 6.400E-09 |
| IFN-α protein (pg/mL) | Eotaxin-2 | 256 | -2.313E-01 | 1.884E-04 | 6.214E-04 |
| IFN-α protein (pg/mL) | HDL in the H3P size range (μM) | 50 | -5.015E-01 | 2.072E-04 | 6.810E-04 |
| IFN-α protein (pg/mL) | CitH3-DNA | 185 | 2.318E-01 | 1.498E-03 | 4.357E-03 |
| IFN-α protein (pg/mL) | HDLC (mg/dL) | 50 | -3.666E-01 | 8.836E-03 | 2.034E-02 |
| IFN-α protein (pg/mL) | Apolipoprotein A1 (mg/dL) | 50 | -3.254E-01 | 2.113E-02 | 4.426E-02 |
| IFN-α protein (pg/mL) | NE-DNA | 185 | 1.575E-01 | 3.231E-02 | 6.367E-02 |
| IFN-α protein (pg/mL) | Ferritin | 256 | 1.191E-01 | 5.704E-02 | 1.030E-01 |
| IFN-α protein (pg/mL) | CEC | 127 | -1.401E-01 | 1.162E-01 | 1.862E-01 |
| IFN-α protein (pg/mL) | cHDLP (μM) | 50 | -1.915E-01 | 1.828E-01 | 2.766E-01 |
| IFN-α protein (pg/mL) | IR | 106 | 9.313E-02 | 3.424E-01 | 4.487E-01 |
| IFN-α protein (pg/mL) | GlycA | 50 | -1.023E-01 | 4.795E-01 | 5.881E-01 |
| CitH3-DNA | ANG2 | 190 | 2.337E-01 | 1.176E-03 | 3.479E-03 |
| CitH3-DNA | CEC | 123 | -2.850E-01 | 1.397E-03 | 4.104E-03 |
| CitH3-DNA | BLC | 190 | 1.417E-01 | 5.108E-02 | 9.378E-02 |
| CitH3-DNA | Apolipoprotein A1 (mg/dL) | 48 | -2.362E-01 | 1.061E-01 | 1.742E-01 |
| CitH3-DNA | cHDLP (μM) | 48 | -1.416E-01 | 3.372E-01 | 4.446E-01 |
| CitH3-DNA | B2M | 189 | 5.637E-02 | 4.410E-01 | 5.480E-01 |
| CitH3-DNA | BAFF | 190 | 5.095E-02 | 4.851E-01 | 5.916E-01 |
| MPO-DNA | NE-DNA | 190 | 4.851E-01 | 1.319E-12 | 8.740E-12 |
| MPO-DNA | CitH3-DNA | 190 | 4.002E-01 | 1.061E-08 | 5.130E-08 |
| MPO-DNA | ITAC | 190 | 2.412E-01 | 8.008E-04 | 2.433E-03 |
| MPO-DNA | Eotaxin-2 | 190 | -2.399E-01 | 8.579E-04 | 2.583E-03 |
| MPO-DNA | ANG2 | 190 | 2.220E-01 | 2.078E-03 | 5.829E-03 |
| MPO-DNA | CEC | 123 | -2.613E-01 | 3.512E-03 | 9.214E-03 |
| MPO-DNA | IL1RII | 190 | -2.107E-01 | 3.531E-03 | 9.214E-03 |
| MPO-DNA | IgE | 190 | 2.042E-01 | 4.718E-03 | 1.169E-02 |
| MPO-DNA | Ficolin 3 | 190 | 2.035E-01 | 4.868E-03 | 1.197E-02 |
| MPO-DNA | IFN-α protein (pg/mL) | 185 | 1.930E-01 | 8.482E-03 | 1.964E-02 |
| MPO-DNA | MCP2 | 190 | 1.547E-01 | 3.304E-02 | 6.451E-02 |
| MPO-DNA | BLC | 190 | 1.422E-01 | 5.027E-02 | 9.268E-02 |
| MPO-DNA | MIP3-β | 190 | 1.324E-01 | 6.853E-02 | 1.192E-01 |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
| --- | --- | --- | --- | --- | --- |
| MPO-DNA | GlycA | 48 | −2.278E−01 | 1.194E−01 | 1.907E−01 |
| MPO-DNA | Lymphocyte count | 184 | −8.838E−02 | 2.329E−01 | 3.364E−01 |
| MPO-DNA | IL-2 | 182 | 8.366E−02 | 2.615E−01 | 3.697E−01 |
| MPO-DNA | Medium TRLP (nM) | 48 | 1.619E−01 | 2.715E−01 | 3.792E−01 |
| MPO-DNA | BAFF | 190 | 7.978E−02 | 2.739E−01 | 3.809E−01 |
| MPO-DNA | HDL in the H3P size range (μM) | 48 | −1.499E−01 | 3.091E−01 | 4.165E−01 |
| MPO-DNA | IP-10 | 190 | 6.977E−02 | 3.388E−01 | 4.461E−01 |
| MPO-DNA | Medium cHDLP (μM) | 48 | −1.304E−01 | 3.768E−01 | 4.872E−01 |
| MPO-DNA | B2M | 189 | 6.253E−02 | 3.926E−01 | 5.031E−01 |
| MPO-DNA | IR | 76 | −7.167E−02 | 5.384E−01 | 6.350E−01 |
| MPO-DNA | IFN-γ | 185 | 4.009E−02 | 5.880E−01 | 6.804E−01 |
| MPO-DNA | HDLC (mg/dL) | 48 | −6.501E−02 | 6.606E−01 | 7.465E−01 |
| MPO-DNA | Apolipoprotein A1 (mg/dL) | 48 | −5.931E−02 | 6.888E−01 | 7.682E−01 |
| MPO-DNA | IL-10 | 183 | −2.567E−02 | 7.301E−01 | 8.028E−01 |
| MPO-DNA | cHDLP (μM) | 48 | 4.773E−02 | 7.473E−01 | 8.145E−01 |
| MPO-DNA | MCP1 | 190 | −2.208E−02 | 7.624E−01 | 8.236E−01 |
| MPO-DNA | Ferritin | 190 | −3.934E−03 | 9.570E−01 | 9.671E−01 |
| MPO-DNA | MPO-DNA | 190 | | 1.000E+00 | |
| NE-DNA | CitH3-DNA | 190 | 7.106E−01 | <E−14 | <E−14 |
| NE-DNA | Eotaxin-2 | 190 | −2.071E−01 | 4.141E−03 | 1.052E−02 |
| NE-DNA | ANG2 | 190 | 1.629E−01 | 2.470E−02 | 5.004E−02 |
| NE-DNA | CEC | 123 | −1.953E−01 | 3.042E−02 | 6.021E−02 |
| NE-DNA | Ficolin 3 | 190 | 1.315E−01 | 7.058E−02 | 1.220E−01 |
| NE-DNA | BLC | 190 | 1.090E−01 | 1.344E−01 | 2.093E−01 |
| NE-DNA | HDL in the H3P size range (μM) | 48 | −1.457E−01 | 3.230E−01 | 4.305E−01 |
| NE-DNA | B2M | 189 | 5.800E−02 | 4.279E−01 | 5.339E−01 |
| NE-DNA | BAFF | 190 | 3.634E−02 | 6.187E−01 | 7.102E−01 |
| NE-DNA | HDLC (mg/dL) | 48 | −7.077E−02 | 6.327E−01 | 7.234E−01 |
| NE-DNA | Ferritin | 190 | −3.322E−02 | 6.491E−01 | 7.354E−01 |
| NE-DNA | cHDLP (μM) | 48 | −4.062E−02 | 7.840E−01 | 8.427E−01 |
| NE-DNA | Apolipoprotein A1 (mg/dL) | 48 | −3.536E−02 | 8.114E−01 | 8.625E−01 |
| NE-DNA | GlycA | 48 | 1.211E−02 | 9.349E−01 | 9.532E−01 |
| NE-DNA | NE-DNA | 190 | | 1.000E+00 | |
| IL-10 | BLC | 254 | 4.905E−01 | <E−14 | <E−14 |
| IL-10 | IFN-α protein (pg/mL) | 254 | 5.486E−01 | <E−14 | <E−14 |
| IL-10 | B2M | 253 | 5.959E−01 | <E−14 | <E−14 |
| IL-10 | IP-10 | 254 | 6.689E−01 | <E−14 | <E−14 |
| IL-10 | ITAC | 254 | 4.775E−01 | <E−14 | <E−14 |
| IL-10 | BAFF | 254 | 4.620E−01 | <E−14 | 6.250E−14 |
| IL-10 | IFN-γ | 254 | 4.601E−01 | 1.021E−14 | 8.070E−14 |
| IL-10 | ANG2 | 254 | 4.558E−01 | 1.954E−14 | 1.490E−13 |
| IL-10 | Ficolin 3 | 254 | 2.639E−01 | 2.029E−05 | 7.530E−05 |
| IL-10 | cHDLP (μM) | 50 | −4.470E−01 | 1.138E−03 | 3.377E−03 |
| IL-10 | IgE | 254 | 1.902E−01 | 2.332E−03 | 6.437E−03 |
| IL-10 | IR | 105 | 2.835E−01 | 3.386E−03 | 8.989E−03 |
| IL-10 | IL1RII | 254 | −1.817E−01 | 3.658E−03 | 9.482E−03 |
| IL-10 | GlycA | 50 | 3.746E−01 | 7.364E−03 | 1.737E−02 |
| IL-10 | Apolipoprotein A1 (mg/dL) | 50 | −3.365E−01 | 1.689E−02 | 3.573E−02 |
| IL-10 | HDLC (mg/dL) | 50 | −3.220E−01 | 2.260E−02 | 4.712E−02 |
| IL-10 | Ferritin | 254 | 1.418E−01 | 2.385E−02 | 4.890E−02 |
| IL-10 | HDL in the H3P size range (μM) | 50 | −1.432E−01 | 3.211E−01 | 4.293E−01 |
| IL-10 | CitH3-DNA | 183 | 6.972E−02 | 3.484E−01 | 4.558E−01 |
| IL-10 | CEC | 125 | −7.410E−02 | 4.115E−01 | 5.193E−01 |
| IL-10 | NE-DNA | 183 | 5.199E−02 | 4.846E−01 | 5.916E−01 |
| IL-10 | Eotaxin-2 | 254 | −9.713E−03 | 8.776E−01 | 9.159E−01 |
| IL-10 | IL-10 | 254 | | 1.000E+00 | |
| TNF-α | MCP1 | 254 | 4.939E−01 | <E−14 | <E−14 |
| TNF-α | ANG2 | 254 | 5.323E−01 | <E−14 | <E−14 |
| TNF-α | IFN-γ | 254 | 5.361E−01 | <E−14 | <E−14 |
| TNF-α | BAFF | 254 | 5.682E−01 | <E−14 | <E−14 |
| TNF-α | Progranulin | 254 | 5.700E−01 | <E−14 | <E−14 |
| TNF-α | ITAC | 254 | 5.831E−01 | <E−14 | <E−14 |
| TNF-α | MCP2 | 254 | 5.983E−01 | <E−14 | <E−14 |
| TNF-α | IFN-α protein (pg/mL) | 254 | 6.172E−01 | <E−14 | <E−14 |
| TNF-α | IL-2 | 252 | 6.262E−01 | <E−14 | <E−14 |
| TNF-α | MIP3-β | 254 | 6.899E−01 | <E−14 | <E−14 |
| TNF-α | B2M | 253 | 7.086E−01 | <E−14 | <E−14 |
| TNF-α | IP-10 | 254 | 7.222E−01 | <E−14 | <E−14 |
| TNF-α | IL-10 | 253 | 7.324E−01 | <E−14 | <E−14 |
| TNF-α | BLC | 254 | 4.297E−01 | 7.807E−13 | 5.330E−12 |
| TNF-α | Lymphocyte count | 249 | −3.186E−01 | 2.800E−07 | 1.240E−06 |
| TNF-α | IL1RII | 254 | −2.957E−01 | 1.606E−06 | 6.780E−06 |
| TNF-α | IgE | 254 | 2.355E−01 | 1.517E−04 | 5.162E−04 |
| TNF-α | Ficolin 3 | 254 | 2.305E−01 | 2.112E−04 | 6.915E−04 |
| TNF-α | HDLC (mg/dL) | 50 | −4.609E−01 | 7.554E−04 | 2.306E−03 |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
| --- | --- | --- | --- | --- | --- |
| TNF-α | Neutrophil number | 249 | −1.949E−01 | 2.008E−03 | 5.669E−03 |
| TNF-α | Apolipoprotein A1 (mg/dL) | 50 | −4.184E−01 | 2.497E−03 | 6.826E−03 |
| TNF-α | cHDLP (μM) | 50 | −3.883E−01 | 5.331E−03 | 1.297E−02 |
| TNF-α | Medium cHDLP (μM) | 50 | −3.416E−01 | 1.520E−02 | 3.246E−02 |
| TNF-α | HDL in the H3P size range (μM) | 50 | −3.398E−01 | 1.577E−02 | 3.352E−02 |
| TNF-α | Eotaxin-2 | 254 | −1.383E−01 | 2.754E−02 | 5.489E−02 |
| TNF-α | CEC | 126 | −1.962E−01 | 2.771E−02 | 5.510E−02 |
| TNF-α | Total cholesterol (mg/dL) | 50 | −2.919E−01 | 3.971E−02 | 7.548E−02 |
| TNF-α | Ferritin | 254 | 1.202E−01 | 5.578E−02 | 1.011E−01 |
| TNF-α | CitH3-DNA | 183 | 1.185E−01 | 1.102E−01 | 1.777E−01 |
| TNF-α | NE-DNA | 183 | 1.039E−01 | 1.618E−01 | 2.483E−01 |
| TNF-α | MPO-DNA | 183 | 7.888E−02 | 2.885E−01 | 3.949E−01 |
| TNF-α | Medium TRLP (nM) | 50 | 1.407E−01 | 3.297E−01 | 4.367E−01 |
| TNF-α | IR | 106 | 9.146E−02 | 3.511E−01 | 4.587E−01 |
| TNF-α | TRAILR3 | 254 | −4.429E−02 | 4.822E−01 | 5.904E−01 |
| TNF-α | GlycA | 50 | 2.381E−02 | 8.696E−01 | 9.098E−01 |
| GlycA | BAFF | 50 | −2.471E−01 | 8.364E−02 | 1.415E−01 |
| GlycA | Eotaxin-2 | 50 | 2.409E−01 | 9.188E−02 | 1.536E−01 |
| GlycA | BLC | 50 | 1.916E−01 | 1.825E−01 | 2.766E−01 |
| GlycA | CitH3-DNA | 48 | −1.288E−01 | 3.829E−01 | 4.928E−01 |
| GlycA | cHDLP (μM) | 50 | −1.172E−01 | 4.178E−01 | 5.244E−01 |
| GlycA | Apolipoprotein A1 (mg/dL) | 50 | −8.643E−02 | 5.506E−01 | 6.459E−01 |
| GlycA | B2M | 49 | −8.382E−02 | 5.669E−01 | 6.605E−01 |
| GlycA | Ficolin 3 | 50 | 5.595E−02 | 6.996E−01 | 7.762E−01 |
| GlycA | CEC | 50 | −4.466E−02 | 7.581E−01 | 8.221E−01 |
| GlycA | Ferritin | 50 | −3.667E−02 | 8.004E−01 | 8.549E−01 |
| GlycA | ANG2 | 50 | −5.693E−03 | 9.687E−01 | 9.768E−01 |
| CEC | Apolipoprotein A1 (mg/dL) | 50 | 4.846E−01 | 3.625E−04 | 1.156E−03 |
| CEC | BAFF | 129 | −2.266E−01 | 9.824E−03 | 2.191E−02 |
| CEC | ANG2 | 129 | −2.152E−01 | 1.430E−02 | 3.078E−02 |
| CEC | B2M | 128 | −1.862E−01 | 3.536E−02 | 6.827E−02 |
| CEC | BLC | 129 | −7.015E−02 | 4.296E−01 | 5.353E−01 |
| Leukocyte count | Lymphocyte count | 298 | 4.622E−01 | <E−14 | <E−14 |
| Leukocyte count | Neutrophil number | 297 | 9.381E−01 | <E−14 | <E−14 |
| Leukocyte count | Progranulin | 295 | −3.929E−01 | 2.513E−12 | 1.600E−11 |
| Leukocyte count | IFN-α protein (pg/mL) | 251 | −4.146E−01 | 7.620E−12 | 4.790E−11 |
| Leukocyte count | IP-10 | 295 | −3.479E−01 | 8.067E−10 | 4.290E−09 |
| Leukocyte count | TRAILR3 | 295 | 3.464E−01 | 9.658E−10 | 5.100E−09 |
| Leukocyte count | MIP3-β | 295 | −3.322E−01 | 4.974E−09 | 2.490E−08 |
| Leukocyte count | MCP2 | 295 | −3.267E−01 | 9.195E−09 | 4.500E−08 |
| Leukocyte count | ITAC | 295 | −3.098E−01 | 5.580E−08 | 2.600E−07 |
| Leukocyte count | IL1RII | 295 | 3.013E−01 | 1.316E−07 | 6.000E−07 |
| Leukocyte count | BAFF | 295 | −3.012E−01 | 1.329E−07 | 6.020E−07 |
| Leukocyte count | B2M | 294 | −2.911E−01 | 3.758E−07 | 1.660E−06 |
| Leukocyte count | VCAM1 | 295 | −2.839E−01 | 7.107E−07 | 3.070E−06 |
| Leukocyte count | IL-2 | 248 | −2.950E−01 | 2.266E−06 | 9.430E−06 |
| Leukocyte count | Eotaxin-2 | 295 | 2.683E−01 | 2.951E−06 | 1.210E−05 |
| Leukocyte count | TNF-α | 249 | −2.859E−01 | 4.542E−06 | 1.820E−05 |
| Leukocyte count | IFN-γ | 251 | −2.552E−01 | 4.309E−05 | 1.539E−04 |
| Leukocyte count | ANG2 | 295 | −2.246E−01 | 9.960E−05 | 3.430E−04 |
| Leukocyte count | Total cholesterol (mg/dL) | 50 | 4.890E−01 | 3.142E−04 | 1.009E−03 |
| Leukocyte count | Ficolin 3 | 295 | −2.007E−01 | 5.239E−04 | 1.628E−03 |
| Leukocyte count | BLC | 295 | −1.850E−01 | 1.414E−03 | 4.126E−03 |
| Leukocyte count | Very Large TRLP (nM) | 50 | 4.359E−01 | 1.555E−03 | 4.492E−03 |
| Leukocyte count | IgE | 295 | −1.687E−01 | 3.667E−03 | 9.482E−03 |
| Leukocyte count | von Willebrand factor | 294 | −1.540E−01 | 8.153E−03 | 1.908E−02 |
| Leukocyte count | MPO-DNA | 184 | −1.919E−01 | 9.053E−03 | 2.062E−02 |
| Leukocyte count | CitH3-DNA | 184 | −1.878E−01 | 1.067E−02 | 2.361E−02 |
| Leukocyte count | NE-DNA | 184 | −1.658E−01 | 2.452E−02 | 4.991E−02 |
| Leukocyte count | HDL in the H3P size range (μM) | 50 | 2.690E−01 | 5.889E−02 | 1.059E−01 |
| Leukocyte count | MCP1 | 295 | −1.091E−01 | 6.127E−02 | 1.090E−01 |
| Leukocyte count | cHDLP (μM) | 50 | 2.614E−01 | 6.668E−02 | 1.165E−01 |
| Leukocyte count | Apolipoprotein A1 (mg/dL) | 50 | 2.551E−01 | 7.375E−02 | 1.273E−01 |
| Leukocyte count | IL-10 | 249 | −1.129E−01 | 7.539E−02 | 1.293E−01 |
| Leukocyte count | HDLC (mg/dL) | 50 | 2.363E−01 | 9.849E−02 | 1.634E−01 |
| Leukocyte count | GlycA | 50 | 2.308E−01 | 1.068E−01 | 1.742E−01 |
| Leukocyte count | Medium TRLP (nM) | 50 | 2.219E−01 | 1.214E−01 | 1.922E−01 |
| Leukocyte count | IR | 121 | 1.404E−01 | 1.245E−01 | 1.960E−01 |
| Leukocyte count | CEC | 128 | 1.177E−01 | 1.857E−01 | 2.800E−01 |
| Leukocyte count | Ferritin | 295 | −6.562E−02 | 2.612E−01 | 3.697E−01 |
| Leukocyte count | Medium cHDLP (μM) | 50 | 1.002E−01 | 4.885E−01 | 5.924E−01 |
| Leukocyte count | Very Small TRLP (nM) | 50 | 4.953E−02 | 7.327E−01 | 8.046E−01 |
| Leukocyte count | Leukocyte count | 298 | | 1.000E+00 | |
| von Willebrand factor | VCAM1 | 302 | 5.206E−01 | <E−14 | <E−14 |
| von Willebrand factor | B2M | 302 | 4.025E−01 | 3.459E−13 | 2.480E−12 |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
| --- | --- | --- | --- | --- | --- |
| von Willebrand factor | TNF-α | 253 | 4.268E-01 | 1.277E-12 | 8.590E-12 |
| von Willebrand factor | IP-10 | 302 | 3.630E-01 | 7.752E-11 | 4.540E-10 |
| von Willebrand factor | IL-10 | 253 | 3.939E-01 | 8.073E-11 | 4.700E-10 |
| von Willebrand factor | MCP2 | 302 | 3.538E-01 | 2.486E-10 | 1.380E-09 |
| von Willebrand factor | Progranulin | 302 | 3.150E-01 | 2.204E-08 | 1.050E-07 |
| von Willebrand factor | IFN-α protein (pg/mL) | 255 | 3.223E-01 | 1.417E-07 | 6.350E-07 |
| von Willebrand factor | BLC | 302 | 2.966E-01 | 1.513E-07 | 6.750E-07 |
| von Willebrand factor | Ferritin | 302 | 2.765E-01 | 1.056E-06 | 4.530E-06 |
| von Willebrand factor | ITAC | 302 | 2.719E-01 | 1.617E-06 | 6.790E-06 |
| von Willebrand factor | MIP3-β | 302 | 2.629E-01 | 3.641E-06 | 1.480E-05 |
| von Willebrand factor | BAFF | 302 | 2.602E-01 | 4.614E-06 | 1.840E-05 |
| von Willebrand factor | MCP1 | 302 | 2.492E-01 | 1.176E-05 | 4.540E-05 |
| von Willebrand factor | Ficolin 3 | 302 | 2.469E-01 | 1.418E-05 | 5.430E-05 |
| von Willebrand factor | ANG2 | 302 | 2.452E-01 | 1.633E-05 | 6.200E-05 |
| von Willebrand factor | IL-2 | 252 | 2.659E-01 | 1.887E-05 | 7.090E-05 |
| von Willebrand factor | Lymphocyte count | 294 | -2.369E-01 | 4.087E-05 | 1.472E-04 |
| von Willebrand factor | IFN-γ | 255 | 1.861E-01 | 2.847E-03 | 7.685E-03 |
| von Willebrand factor | Very Small TRLP (nM) | 49 | 2.319E-01 | 1.089E-01 | 1.762E-01 |
| von Willebrand factor | MPO-DNA | 189 | -1.021E-01 | 1.621E-01 | 2.483E-01 |
| von Willebrand factor | TRAILR3 | 302 | -7.787E-02 | 1.771E-01 | 2.690E-01 |
| von Willebrand factor | cHDLP (μM) | 49 | -1.830E-01 | 2.082E-01 | 3.080E-01 |
| von Willebrand factor | Neutrophil number | 294 | -7.097E-02 | 2.251E-01 | 3.268E-01 |
| von Willebrand factor | IL1RII | 302 | -6.234E-02 | 2.802E-01 | 3.860E-01 |
| von Willebrand factor | Very Large TRLP (nM) | 49 | -1.508E-01 | 3.010E-01 | 4.100E-01 |
| von Willebrand factor | Eotaxin-2 | 302 | 5.890E-02 | 3.076E-01 | 4.158E-01 |
| von Willebrand factor | CEC | 128 | 7.140E-02 | 4.232E-01 | 5.288E-01 |
| von Willebrand factor | GlycA | 49 | 6.935E-02 | 6.359E-01 | 7.242E-01 |
| von Willebrand factor | HDLC (mg/dL) | 49 | -6.381E-02 | 6.631E-01 | 7.476E-01 |
| von Willebrand factor | Medium TRLP (nM) | 49 | 6.377E-02 | 6.634E-01 | 7.476E-01 |
| von Willebrand factor | Apolipoprotein A1 (mg/dL) | 49 | -5.765E-02 | 6.940E-01 | 7.710E-01 |
| von Willebrand factor | Medium cHDLP (μM) | 49 | -5.431E-02 | 7.109E-01 | 7.857E-01 |
| von Willebrand factor | NE-DNA | 189 | -2.424E-02 | 7.406E-01 | 8.092E-01 |
| von Willebrand factor | CitH3-DNA | 189 | -1.054E-02 | 8.856E-01 | 9.198E-01 |
| von Willebrand factor | IR | 118 | -1.245E-02 | 8.936E-01 | 9.269E-01 |
| von Willebrand factor | IgE | 302 | 7.378E-03 | 8.984E-01 | 9.308E-01 |
| von Willebrand factor | HDL in the H3P size range (μM) | 49 | -3.626E-03 | 9.803E-01 | 9.837E-01 |
| von Willebrand factor | Total cholesterol (mg/dL) | 49 | 2.731E-03 | 9.851E-01 | 9.863E-01 |
| Very Small TRLP (nM) | BAFF | 50 | 4.007E-01 | 3.932E-03 | 1.008E-02 |
| Very Small TRLP (nM) | TNF-α | 50 | 3.671E-01 | 8.740E-03 | 2.017E-02 |
| Very Small TRLP (nM) | B2M | 49 | 2.906E-01 | 4.284E-02 | 8.071E-02 |
| Very Small TRLP (nM) | HDLC (mg/dL) | 50 | -2.730E-01 | 5.508E-02 | 1.003E-01 |
| Very Small TRLP (nM) | VCAM1 | 50 | 2.658E-01 | 6.207E-02 | 1.098E-01 |
| Very Small TRLP (nM) | ANG2 | 50 | 2.539E-01 | 7.515E-02 | 1.293E-01 |
| Very Small TRLP (nM) | IL-10 | 50 | 2.524E-01 | 7.700E-02 | 1.318E-01 |
| Very Small TRLP (nM) | ITAC | 50 | 2.145E-01 | 1.347E-01 | 2.094E-01 |
| Very Small TRLP (nM) | IFN-γ | 50 | 2.025E-01 | 1.585E-01 | 2.437E-01 |
| Very Small TRLP (nM) | IL-2 | 49 | 1.977E-01 | 1.732E-01 | 2.640E-01 |
| Very Small TRLP (nM) | Apolipoprotein A1 (mg/dL) | 50 | -1.912E-01 | 1.835E-01 | 2.772E-01 |
| Very Small TRLP (nM) | MCP1 | 50 | 1.870E-01 | 1.935E-01 | 2.892E-01 |
| Very Small TRLP (nM) | MIP3-β | 50 | 1.853E-01 | 1.977E-01 | 2.950E-01 |
| Very Small TRLP (nM) | cHDLP (μM) | 50 | -1.748E-01 | 2.246E-01 | 3.267E-01 |
| Very Small TRLP (nM) | Ferritin | 50 | 1.582E-01 | 2.726E-01 | 3.798E-01 |
| Very Small TRLP (nM) | Medium cHDLP (μM) | 50 | -1.565E-01 | 2.779E-01 | 3.840E-01 |
| Very Small TRLP (nM) | IFN-α protein (pg/mL) | 50 | 1.488E-01 | 3.024E-01 | 4.113E-01 |
| Very Small TRLP (nM) | HDL in the H3P size range (μM) | 50 | -1.452E-01 | 3.142E-01 | 4.214E-01 |
| Very Small TRLP (nM) | Progranulin | 50 | 1.378E-01 | 3.399E-01 | 4.461E-01 |
| Very Small TRLP (nM) | Ficolin 3 | 50 | 1.267E-01 | 3.805E-01 | 4.904E-01 |
| Very Small TRLP (nM) | IP-10 | 50 | 1.187E-01 | 4.118E-01 | 5.193E-01 |
| Very Small TRLP (nM) | Medium TRLP (nM) | 50 | 1.167E-01 | 4.197E-01 | 5.252E-01 |
| Very Small TRLP (nM) | MCP2 | 50 | 1.128E-01 | 4.354E-01 | 5.417E-01 |
| Very Small TRLP (nM) | Total cholesterol (mg/dL) | 50 | 1.087E-01 | 4.525E-01 | 5.598E-01 |
| Very Small TRLP (nM) | BLC | 50 | -1.003E-01 | 4.882E-01 | 5.924E-01 |
| Very Small TRLP (nM) | Eotaxin-2 | 50 | -9.795E-02 | 4.986E-01 | 6.021E-01 |
| Very Small TRLP (nM) | Neutrophil number | 50 | 8.363E-02 | 5.637E-01 | 6.576E-01 |
| Very Small TRLP (nM) | GlycA | 50 | 6.948E-02 | 6.316E-01 | 7.232E-01 |
| Very Small TRLP (nM) | Very Large TRLP (nM) | 50 | 4.752E-02 | 7.431E-01 | 8.109E-01 |
| Very Small TRLP (nM) | CEC | 50 | -4.121E-02 | 7.763E-01 | 8.355E-01 |
| Very Small TRLP (nM) | IR | 34 | -4.482E-02 | 8.013E-01 | 8.549E-01 |
| Very Small TRLP (nM) | IgE | 50 | 2.850E-02 | 8.442E-01 | 8.923E-01 |
| Very Small TRLP (nM) | IL1RII | 50 | -2.209E-02 | 8.790E-01 | 9.162E-01 |
| Very Small TRLP (nM) | CitH3-DNA | 48 | 1.630E-02 | 9.124E-01 | 9.428E-01 |
| Very Small TRLP (nM) | MPO-DNA | 48 | -1.353E-02 | 9.273E-01 | 9.516E-01 |
| Very Small TRLP (nM) | Lymphocyte count | 50 | -1.197E-02 | 9.342E-01 | 9.532E-01 |
| Very Small TRLP (nM) | TRAILR3 | 50 | 1.005E-02 | 9.448E-01 | 9.578E-01 |
| Very Small TRLP (nM) | NE-DNA | 48 | 8.747E-03 | 9.529E-01 | 9.641E-01 |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
|---|---|---|---|---|---|
| Very Small TRLP (nM) | Very Small TRLP (nM) | 50 | | 1.000E+00 | |
| Very Large TRLP (nM) | cHDLP (μM) | 50 | 5.339E-01 | 6.517E-05 | 2.290E-04 |
| Very Large TRLP (nM) | Total cholesterol (mg/dL) | 50 | 4.824E-01 | 3.887E-04 | 1.226E-03 |
| Very Large TRLP (nM) | Apolipoprotein A1 (mg/dL) | 50 | 4.658E-01 | 6.531E-04 | 2.001E-03 |
| Very Large TRLP (nM) | Neutrophil number | 50 | 4.022E-01 | 3.787E-03 | 9.733E-03 |
| Very Large TRLP (nM) | IR | 34 | 4.804E-01 | 4.034E-03 | 1.028E-02 |
| Very Large TRLP (nM) | HDL in the H3P size range (μM) | 50 | 3.810E-01 | 6.337E-03 | 1.516E-02 |
| Very Large TRLP (nM) | IL1RII | 50 | 3.657E-01 | 9.016E-03 | 2.062E-02 |
| Very Large TRLP (nM) | HDLC (mg/dL) | 50 | 3.622E-01 | 9.742E-03 | 2.179E-02 |
| Very Large TRLP (nM) | B2M | 49 | -3.228E-01 | 2.370E-02 | 4.883E-02 |
| Very Large TRLP (nM) | Medium cHDLP (μM) | 50 | 2.976E-01 | 3.584E-02 | 6.903E-02 |
| Very Large TRLP (nM) | VCAM1 | 50 | -2.815E-01 | 4.763E-02 | 8.857E-02 |
| Very Large TRLP (nM) | MIP3-β | 50 | -2.583E-01 | 7.015E-02 | 1.215E-01 |
| Very Large TRLP (nM) | Progranulin | 50 | -2.310E-01 | 1.065E-01 | 1.742E-01 |
| Very Large TRLP (nM) | CEC | 50 | 2.299E-01 | 1.082E-01 | 1.757E-01 |
| Very Large TRLP (nM) | TRAILR3 | 50 | 2.219E-01 | 1.215E-01 | 1.922E-01 |
| Very Large TRLP (nM) | BAFF | 50 | -2.177E-01 | 1.289E-01 | 2.014E-01 |
| Very Large TRLP (nM) | Ferritin | 50 | -1.808E-01 | 2.089E-01 | 3.086E-01 |
| Very Large TRLP (nM) | IP-10 | 50 | -1.792E-01 | 2.131E-01 | 3.136E-01 |
| Very Large TRLP (nM) | TNF-α | 50 | -1.785E-01 | 2.148E-01 | 3.151E-01 |
| Very Large TRLP (nM) | IL-10 | 50 | -1.672E-01 | 2.458E-01 | 3.504E-01 |
| Very Large TRLP (nM) | Lymphocyte count | 50 | 1.601E-01 | 2.668E-01 | 3.753E-01 |
| Very Large TRLP (nM) | ANG2 | 50 | -1.569E-01 | 2.765E-01 | 3.840E-01 |
| Very Large TRLP (nM) | Medium TRLP (nM) | 50 | 1.474E-01 | 3.070E-01 | 4.158E-01 |
| Very Large TRLP (nM) | IgE | 50 | 1.409E-01 | 3.289E-01 | 4.367E-01 |
| Very Large TRLP (nM) | MCP1 | 50 | 1.173E-01 | 4.172E-01 | 5.244E-01 |
| Very Large TRLP (nM) | Eotaxin-2 | 50 | 1.033E-01 | 4.754E-01 | 5.847E-01 |
| Very Large TRLP (nM) | IFN-α protein (pg/mL) | 50 | -9.687E-02 | 5.033E-01 | 6.061E-01 |
| Very Large TRLP (nM) | IL-2 | 49 | -9.369E-02 | 5.220E-01 | 6.224E-01 |
| Very Large TRLP (nM) | GlycA | 50 | 7.964E-02 | 5.825E-01 | 6.750E-01 |
| Very Large TRLP (nM) | IFN-γ | 50 | -6.757E-02 | 6.411E-01 | 7.272E-01 |
| Very Large TRLP (nM) | NE-DNA | 48 | -6.026E-02 | 6.841E-01 | 7.640E-01 |
| Very Large TRLP (nM) | Ficolin 3 | 50 | 4.509E-02 | 7.559E-01 | 8.207E-01 |
| Very Large TRLP (nM) | MPO-DNA | 48 | -4.480E-02 | 7.624E-01 | 8.236E-01 |
| Very Large TRLP (nM) | CitH3-DNA | 48 | -4.015E-02 | 7.864E-01 | 8.440E-01 |
| Very Large TRLP (nM) | MCP2 | 50 | 3.532E-02 | 8.076E-01 | 8.595E-01 |
| Very Large TRLP (nM) | ITAC | 50 | -2.831E-02 | 8.453E-01 | 8.923E-01 |
| Very Large TRLP (nM) | BLC | 50 | -4.225E-03 | 9.768E-01 | 9.813E-01 |
| VCAM1 | BLC | 303 | 4.577E-01 | <E-14 | <E-14 |
| VCAM1 | MCP2 | 303 | 4.590E-01 | <E-14 | <E-14 |
| VCAM1 | ANG2 | 303 | 4.630E-01 | <E-14 | <E-14 |
| VCAM1 | ITAC | 303 | 4.671E-01 | <E-14 | <E-14 |
| VCAM1 | BAFF | 303 | 4.683E-01 | <E-14 | <E-14 |
| VCAM1 | IFN-α protein (pg/mL) | 256 | 4.946E-01 | <E-14 | <E-14 |
| VCAM1 | Progranulin | 303 | 5.128E-01 | <E-14 | <E-14 |
| VCAM1 | MIP3-β | 303 | 5.304E-01 | <E-14 | <E-14 |
| VCAM1 | IP-10 | 303 | 5.431E-01 | <E-14 | <E-14 |
| VCAM1 | B2M | 302 | 6.078E-01 | <E-14 | <E-14 |
| VCAM1 | IL-10 | 254 | 6.128E-01 | <E-14 | <E-14 |
| VCAM1 | TNF-α | 254 | 6.843E-01 | <E-14 | <E-14 |
| VCAM1 | IL-2 | 253 | 4.359E-01 | 3.733E-13 | 2.610E-12 |
| VCAM1 | IFN-γ | 256 | 4.032E-01 | 2.005E-11 | 1.220E-10 |
| VCAM1 | Lymphocyte count | 295 | -3.609E-01 | 1.673E-10 | 9.670E-10 |
| VCAM1 | MCP1 | 303 | 3.017E-01 | 8.544E-08 | 3.910E-07 |
| VCAM1 | Ficolin 3 | 303 | 2.429E-01 | 1.908E-05 | 7.140E-05 |
| VCAM1 | Neutrophil number | 295 | -1.686E-01 | 3.678E-03 | 9.482E-03 |
| VCAM1 | Ferritin | 303 | 1.626E-01 | 4.546E-03 | 1.135E-02 |
| VCAM1 | IL1RII | 303 | -1.537E-01 | 7.353E-03 | 1.737E-02 |
| VCAM1 | cHDLP (μM) | 50 | -3.522E-01 | 1.214E-02 | 2.646E-02 |
| VCAM1 | HDLC (mg/dL) | 50 | -3.293E-01 | 1.954E-02 | 4.124E-02 |
| VCAM1 | Total cholesterol (mg/dL) | 50 | -3.216E-01 | 2.278E-02 | 4.738E-02 |
| VCAM1 | IgE | 303 | 1.191E-01 | 3.832E-02 | 7.316E-02 |
| VCAM1 | Apolipoprotein A1 (mg/dL) | 50 | -2.925E-01 | 3.930E-02 | 7.486E-02 |
| VCAM1 | Medium cHDLP (μM) | 50 | -2.834E-01 | 4.610E-02 | 8.621E-02 |
| VCAM1 | HDL in the H3P size range (μM) | 50 | -2.630E-01 | 6.496E-02 | 1.141E-01 |
| VCAM1 | CEC | 129 | -1.350E-01 | 1.271E-01 | 1.990E-01 |
| VCAM1 | CitH3-DNA | 190 | 7.692E-02 | 2.915E-01 | 3.978E-01 |
| VCAM1 | IR | 119 | 6.989E-02 | 4.501E-01 | 5.576E-01 |
| VCAM1 | NE-DNA | 190 | 5.172E-02 | 4.785E-01 | 5.877E-01 |
| VCAM1 | MPO-DNA | 190 | 4.944E-02 | 4.981E-01 | 6.021E-01 |
| VCAM1 | GlycA | 50 | 8.964E-02 | 5.359E-01 | 6.338E-01 |
| VCAM1 | Medium TRLP (nM) | 50 | 6.984E-02 | 6.299E-01 | 7.221E-01 |
| VCAM1 | TRAILR3 | 303 | -9.001E-03 | 8.760E-01 | 9.153E-01 |
| VCAM1 | Eotaxin-2 | 303 | -4.492E-03 | 9.379E-01 | 9.546E-01 |
| VCAM1 | VCAM1 | 303 | | 1.000E+00 | |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
|---|---|---|---|---|---|
| TRAILR3 | Neutrophil number | 295 | 3.352E−01 | 3.548E−09 | 1.810E−08 |
| TRAILR3 | IL1RII | 303 | 2.255E−01 | 7.508E−05 | 2.617E−04 |
| TRAILR3 | Eotaxin-2 | 303 | 2.132E−01 | 1.842E−04 | 6.100E−04 |
| TRAILR3 | IFN-α protein (pg/mL) | 256 | −2.157E−01 | 5.114E−04 | 1.601E−03 |
| TRAILR3 | Ficolin 3 | 303 | −1.487E−01 | 9.516E−03 | 2.150E−02 |
| TRAILR3 | IFN-γ | 256 | −1.421E−01 | 2.298E−02 | 4.767E−02 |
| TRAILR3 | Lymphocyte count | 295 | 1.265E−01 | 2.990E−02 | 5.932E−02 |
| TRAILR3 | Progranulin | 303 | −1.214E−01 | 3.467E−02 | 6.707E−02 |
| TRAILR3 | IL-2 | 253 | −1.191E−01 | 5.863E−02 | 1.056E−01 |
| TRAILR3 | GlycA | 50 | 2.419E−01 | 9.060E−02 | 1.518E−01 |
| TRAILR3 | B2M | 302 | 9.448E−02 | 1.013E−01 | 1.670E−01 |
| TRAILR3 | BLC | 303 | −8.897E−02 | 1.223E−01 | 1.931E−01 |
| TRAILR3 | ANG2 | 303 | 7.157E−02 | 2.141E−01 | 3.146E−01 |
| TRAILR3 | CitH3-DNA | 190 | −8.013E−02 | 2.718E−01 | 3.792E−01 |
| TRAILR3 | IgE | 303 | 5.921E−02 | 3.043E−01 | 4.132E−01 |
| TRAILR3 | HDL in the H3P size range (μM) | 50 | 1.431E−01 | 3.216E−01 | 4.294E−01 |
| TRAILR3 | IP-10 | 303 | −5.618E−02 | 3.297E−01 | 4.367E−01 |
| TRAILR3 | Total cholesterol (mg/dL) | 50 | 1.273E−01 | 3.785E−01 | 4.885E−01 |
| TRAILR3 | MCP1 | 303 | −3.887E−02 | 5.002E−01 | 6.032E−01 |
| TRAILR3 | MPO-DNA | 190 | −4.874E−02 | 5.043E−01 | 6.064E−01 |
| TRAILR3 | IL-10 | 254 | −4.103E−02 | 5.151E−01 | 6.160E−01 |
| TRAILR3 | BAFF | 303 | 2.927E−02 | 6.119E−01 | 7.043E−01 |
| TRAILR3 | NE-DNA | 190 | −2.970E−02 | 6.842E−01 | 7.640E−01 |
| TRAILR3 | Apolipoprotein A1 (mg/dL) | 50 | 5.749E−02 | 6.917E−01 | 7.704E−01 |
| TRAILR3 | MCP2 | 303 | −1.811E−02 | 7.536E−01 | 8.193E−01 |
| TRAILR3 | Medium TRLP (nM) | 50 | 4.206E−02 | 7.718E−01 | 8.327E−01 |
| TRAILR3 | Ferritin | 303 | 1.469E−02 | 7.989E−01 | 8.545E−01 |
| TRAILR3 | HDLC (mg/dL) | 50 | 3.195E−02 | 8.257E−01 | 8.755E−01 |
| TRAILR3 | CEC | 129 | −1.520E−02 | 8.643E−01 | 9.075E−01 |
| TRAILR3 | MIP3-β | 303 | 6.143E−03 | 9.152E−01 | 9.437E−01 |
| TRAILR3 | ITAC | 303 | −5.800E−03 | 9.199E−01 | 9.463E−01 |
| TRAILR3 | cHDLP (μM) | 50 | 1.247E−02 | 9.315E−01 | 9.532E−01 |
| TRAILR3 | IR | 119 | 2.967E−03 | 9.745E−01 | 9.812E−01 |
| TRAILR3 | Medium cHDLP (μM) | 50 | 2.763E−03 | 9.848E−01 | 9.863E−01 |
| TRAILR3 | TRAILR3 | 303 |  | 1.000E+00 |  |
| Total cholesterol (mg/dL) | cHDLP (μM) | 50 | 5.077E−01 | 1.677E−04 | 5.664E−04 |
| Total cholesterol (mg/dL) | Apolipoprotein A1 (mg/dL) | 50 | 4.963E−01 | 2.465E−04 | 7.980E−04 |
| Total cholesterol (mg/dL) | HDLC (mg/dL) | 50 | 4.702E−01 | 5.707E−04 | 1.761E−03 |
| Total cholesterol (mg/dL) | HDL in the H3P size range (M) | 50 | 4.684E−01 | 6.029E−04 | 1.854E−03 |
| Total cholesterol (mg/dL) | Lymphocyte count | 50 | 4.218E−01 | 2.282E−03 | 6.318E−03 |
| Total cholesterol (mg/dL) | Progranulin | 50 | −4.123E−01 | 2.930E−03 | 7.882E−03 |
| Total cholesterol (mg/dL) | BAFF | 50 | −3.965E−01 | 4.359E−03 | 1.094E−02 |
| Total cholesterol (mg/dL) | Neutrophil number | 50 | 3.935E−01 | 4.698E−03 | 1.169E−02 |
| Total cholesterol (mg/dL) | IFN-α protein (pg/mL) | 50 | −3.878E−01 | 5.386E−03 | 1.306E−02 |
| Total cholesterol (mg/dL) | IL-2 | 49 | −3.860E−01 | 6.162E−03 | 1.482E−02 |
| Total cholesterol (mg/dL) | Medium cHDLP (μM) | 50 | 3.648E−01 | 9.205E−03 | 2.091E−02 |
| Total cholesterol (mg/dL) | MCP2 | 50 | −3.415E−01 | 1.523E−02 | 3.246E−02 |
| Total cholesterol (mg/dL) | IL1RII | 50 | 3.180E−01 | 2.444E−02 | 4.986E−02 |
| Total cholesterol (mg/dL) | Eotaxin-2 | 50 | 3.141E−01 | 2.633E−02 | 5.293E−02 |
| Total cholesterol (mg/dL) | GlycA | 50 | 2.994E−01 | 3.465E−02 | 6.707E−02 |
| Total cholesterol (mg/dL) | MIP3-β | 50 | −2.466E−01 | 8.424E−02 | 1.422E−01 |
| Total cholesterol (mg/dL) | B2M | 49 | −2.379E−01 | 9.976E−02 | 1.649E−01 |
| Total cholesterol (mg/dL) | Medium TRLP (nM) | 50 | 2.355E−01 | 9.974E−02 | 1.649E−01 |
| Total cholesterol (mg/dL) | IP-10 | 50 | −2.308E−01 | 1.068E−01 | 1.742E−01 |
| Total cholesterol (mg/dL) | CEC | 50 | 2.301E−01 | 1.079E−01 | 1.756E−01 |
| Total cholesterol (mg/dL) | IFN-γ | 50 | −2.230E−01 | 1.196E−01 | 1.907E−01 |
| Total cholesterol (mg/dL) | ANG2 | 50 | −2.079E−01 | 1.473E−01 | 2.282E−01 |
| Total cholesterol (mg/dL) | IR | 34 | 2.310E−01 | 1.888E−01 | 2.841E−01 |
| Total cholesterol (mg/dL) | CitH3-DNA | 48 | −1.927E−01 | 1.894E−01 | 2.846E−01 |
| Total cholesterol (mg/dL) | IL-10 | 50 | −1.379E−01 | 3.396E−01 | 4.461E−01 |
| Total cholesterol (mg/dL) | ITAC | 50 | −1.231E−01 | 3.946E−01 | 5.040E−01 |
| Total cholesterol (mg/dL) | BLC | 50 | −8.912E−02 | 5.382E−01 | 6.350E−01 |
| Total cholesterol (mg/dL) | MCP1 | 50 | −5.384E−02 | 7.104E−01 | 7.857E−01 |
| Total cholesterol (mg/dL) | MPO-DNA | 48 | 4.278E−02 | 7.728E−01 | 8.328E−01 |
| Total cholesterol (mg/dL) | IgE | 50 | −3.330E−02 | 8.184E−01 | 8.689E−01 |
| Total cholesterol (mg/dL) | NE-DNA | 48 | 2.443E−02 | 8.691E−01 | 9.098E−01 |
| Total cholesterol (mg/dL) | Ficolin 3 | 50 | 1.089E−02 | 9.402E−01 | 9.546E−01 |
| Total cholesterol (mg/dL) | Ferritin | 50 | −5.668E−03 | 9.688E−01 | 9.768E−01 |
| Progranulin | ANG2 | 303 | 4.719E−01 | <E−14 | <E−14 |
| Progranulin | IL-2 | 253 | 4.918E−01 | <E−14 | <E−14 |
| Progranulin | BAFF | 303 | 4.956E−01 | <E−14 | <E−14 |
| Progranulin | IL-10 | 254 | 5.378E−01 | <E−14 | <E−14 |
| Progranulin | ITAC | 303 | 5.448E−01 | <E−14 | <E−14 |
| Progranulin | B2M | 302 | 5.482E−01 | <E−14 | <E−14 |
| Progranulin | MCP2 | 303 | 5.713E−01 | <E−14 | <E−14 |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
| --- | --- | --- | --- | --- | --- |
| Progranulin | IP-10 | 303 | 5.936E-01 | <E-14 | <E-14 |
| Progranulin | IFN-α protein (pg/mL) | 256 | 6.208E-01 | <E-14 | <E-14 |
| Progranulin | MIP3-β | 303 | 6.291E-01 | <E-14 | <E-14 |
| Progranulin | IFN-γ | 256 | 4.835E-01 | <E-14 | <E-14 |
| Progranulin | Ficolin 3 | 303 | 3.686E-01 | 3.478E-11 | 2.070E-10 |
| Progranulin | BLC | 303 | 3.667E-01 | 4.454E-11 | 2.630E-10 |
| Progranulin | MCP1 | 303 | 3.440E-01 | 7.635E-10 | 4.080E-09 |
| Progranulin | Lymphocyte count | 295 | −3.199E-01 | 1.925E-08 | 9.260E-08 |
| Progranulin | Neutrophil number | 295 | −3.155E-01 | 3.047E-08 | 1.450E-07 |
| Progranulin | IgE | 303 | 3.101E-01 | 3.537E-08 | 1.660E-07 |
| Progranulin | IL1RII | 303 | −2.270E-01 | 6.701E-05 | 2.345E-04 |
| Progranulin | Ferritin | 303 | 1.983E-01 | 5.173E-04 | 1.614E-03 |
| Progranulin | HDL in the H3P size range (μM) | 50 | −4.356E-01 | 1.568E-03 | 4.514E-03 |
| Progranulin | Eotaxin-2 | 303 | −1.556E-01 | 6.650E-03 | 1.582E-02 |
| Progranulin | MPO-DNA | 190 | 1.629E-01 | 2.469E-02 | 5.004E-02 |
| Progranulin | CitH3-DNA | 190 | 1.611E-01 | 2.643E-02 | 5.293E-02 |
| Progranulin | NE-DNA | 190 | 1.557E-01 | 3.197E-02 | 6.313E-02 |
| Progranulin | Apolipoprotein A1 (mg/dL) | 50 | −2.833E-01 | 4.616E-02 | 8.621E-02 |
| Progranulin | HDLC (mg/dL) | 50 | −2.673E-01 | 6.054E-02 | 1.079E-01 |
| Progranulin | cHDLP (μM) | 50 | −2.393E-01 | 9.424E-02 | 1.572E-01 |
| Progranulin | Medium cHDLP (μM) | 50 | −1.945E-01 | 1.760E-01 | 2.677E-01 |
| Progranulin | GlycA | 50 | −9.944E-02 | 4.920E-01 | 5.958E-01 |
| Progranulin | Medium TRLP (nM) | 50 | −9.632E-02 | 5.058E-01 | 6.074E-01 |
| Progranulin | CEC | 129 | −5.719E-02 | 5.197E-01 | 6.206E-01 |
| Progranulin | IR | 119 | 1.759E-02 | 8.494E-01 | 8.940E-01 |
| Progranulin | Progranulin | 303 | | 1.000E+00 | |
| Neutrophil number | Eotaxin-2 | 295 | 2.804E-01 | 9.877E-07 | 4.250E-06 |
| Neutrophil number | IFN-α protein (pg/mL) | 251 | −2.941E-01 | 2.128E-06 | 8.890E-06 |
| Neutrophil number | IL1RII | 295 | 2.573E-01 | 7.603E-06 | 2.980E-05 |
| Neutrophil number | MIP3-β | 295 | −2.519E-01 | 1.195E-05 | 4.590E-05 |
| Neutrophil number | IP-10 | 295 | −2.321E-01 | 5.716E-05 | 2.017E-04 |
| Neutrophil number | MCP2 | 295 | −2.251E-01 | 9.639E-05 | 3.346E-04 |
| Neutrophil number | ITAC | 295 | −2.249E-01 | 9.733E-05 | 3.366E-04 |
| Neutrophil number | IL-2 | 248 | −2.310E-01 | 2.440E-04 | 7.928E-04 |
| Neutrophil number | B2M | 294 | −1.893E-01 | 1.108E-03 | 3.301E-03 |
| Neutrophil number | BAFF | 295 | −1.792E-01 | 2.001E-03 | 5.666E-03 |
| Neutrophil number | IFN-γ | 251 | −1.898E-01 | 2.538E-03 | 6.917E-03 |
| Neutrophil number | Lymphocyte count | 297 | 1.691E-01 | 3.472E-03 | 9.170E-03 |
| Neutrophil number | CitH3-DNA | 184 | −1.937E-01 | 8.431E-03 | 1.962E-02 |
| Neutrophil number | MPO-DNA | 184 | −1.908E-01 | 9.493E-03 | 2.150E-02 |
| Neutrophil number | NE-DNA | 184 | −1.886E-01 | 1.037E-02 | 2.301E-02 |
| Neutrophil number | GlycA | 50 | 3.519E-01 | 1.220E-02 | 2.652E-02 |
| Neutrophil number | ANG2 | 295 | −1.428E-01 | 1.410E-02 | 3.043E-02 |
| Neutrophil number | Ficolin 3 | 295 | −1.320E-01 | 2.337E-02 | 4.825E-02 |
| Neutrophil number | IgE | 295 | −1.316E-01 | 2.384E-02 | 4.890E-02 |
| Neutrophil number | IR | 121 | 1.623E-01 | 7.538E-02 | 1.293E-01 |
| Neutrophil number | Medium TRLP (nM) | 50 | 2.169E-01 | 1.302E-01 | 2.031E-01 |
| Neutrophil number | CEC | 128 | 1.076E-01 | 2.266E-01 | 3.285E-01 |
| Neutrophil number | HDL in the H3P size range (μM) | 50 | 1.689E-01 | 2.408E-01 | 3.456E-01 |
| Neutrophil number | Apolipoprotein A1 (mg/dL) | 50 | 1.591E-01 | 2.698E-01 | 3.784E-01 |
| Neutrophil number | cHDLP (μM) | 50 | 1.586E-01 | 2.712E-01 | 3.792E-01 |
| Neutrophil number | HDLC (mg/dL) | 50 | 1.330E-01 | 3.572E-01 | 4.639E-01 |
| Neutrophil number | BLC | 295 | −4.842E-02 | 4.074E-01 | 5.158E-01 |
| Neutrophil number | MCP1 | 295 | −4.377E-02 | 4.539E-01 | 5.607E-01 |
| Neutrophil number | Ferritin | 295 | −3.650E-02 | 5.323E-01 | 6.323E-01 |
| Neutrophil number | IL-10 | 249 | 3.693E-02 | 5.619E-01 | 6.567E-01 |
| Neutrophil number | Medium cHDLP (μM) | 50 | 1.581E-02 | 9.132E-01 | 9.428E-01 |
| MCP2 | IFN-γ | 256 | 4.875E-01 | <E-14 | <E-14 |
| MCP2 | IL-2 | 253 | 5.008E-01 | <E-14 | <E-14 |
| MCP2 | ANG2 | 303 | 5.069E-01 | <E-14 | <E-14 |
| MCP2 | IL-10 | 254 | 5.161E-01 | <E-14 | <E-14 |
| MCP2 | MCP1 | 303 | 5.330E-01 | <E-14 | <E-14 |
| MCP2 | BAFF | 303 | 5.652E-01 | <E-14 | <E-14 |
| MCP2 | B2M | 302 | 5.932E-01 | <E-14 | <E-14 |
| MCP2 | ITAC | 303 | 6.108E-01 | <E-14 | <E-14 |
| MCP2 | IFN-α protein (pg/mL) | 256 | 6.514E-01 | <E-14 | <E-14 |
| MCP2 | MIP3-β | 303 | 6.585E-01 | <E-14 | <E-14 |
| MCP2 | IP-10 | 303 | 7.476E-01 | <E-14 | <E-14 |
| MCP2 | Ficolin 3 | 303 | 3.905E-01 | 1.770E-12 | 1.140E-11 |
| MCP2 | IgE | 303 | 3.747E-01 | 1.559E-11 | 9.660E-11 |
| MCP2 | BLC | 303 | 3.735E-01 | 1.827E-11 | 1.120E-10 |
| MCP2 | Lymphocyte count | 295 | −3.601E-01 | 1.847E-10 | 1.060E-09 |
| MCP2 | Ferritin | 303 | 2.150E-01 | 1.628E-04 | 5.518E-04 |
| MCP2 | HDLC (mg/dL) | 50 | −4.950E-01 | 2.581E-04 | 8.322E-04 |
| MCP2 | CitH3-DNA | 190 | 2.550E-01 | 3.841E-04 | 1.220E-03 |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
|---|---|---|---|---|---|
| MCP2 | Apolipoprotein A1 (mg/dL) | 50 | −4.482E−01 | 1.097E−03 | 3.279E−03 |
| MCP2 | cHDLP (μM) | 50 | −4.361E−01 | 1.546E−03 | 4.481E−03 |
| MCP2 | IL1RII | 303 | −1.564E−01 | 6.383E−03 | 1.522E−02 |
| MCP2 | Eotaxin-2 | 303 | −1.485E−01 | 9.617E−03 | 2.168E−02 |
| MCP2 | NE-DNA | 190 | 1.873E−01 | 9.677E−03 | 2.171E−02 |
| MCP2 | HDL in the H3P size range (μM) | 50 | −2.729E−01 | 5.522E−02 | 1.003E−01 |
| MCP2 | CEC | 129 | −1.516E−01 | 8.634E−02 | 1.455E−01 |
| MCP2 | Medium cHDLP (μM) | 50 | −2.309E−01 | 1.067E−01 | 1.742E−01 |
| MCP2 | GlycA | 50 | −1.175E−01 | 4.163E−01 | 5.240E−01 |
| MCP2 | IR | 119 | 5.233E−02 | 5.719E−01 | 6.654E−01 |
| MCP2 | Medium TRLP (nM) | 50 | −6.501E−02 | 6.538E−01 | 7.397E−01 |
| MCP1 | IP-10 | 303 | 4.637E−01 | <E−14 | <E−14 |
| MCP1 | B2M | 302 | 3.934E−01 | 1.289E−12 | 8.600E−12 |
| MCP1 | IL-10 | 254 | 4.245E−01 | 1.556E−12 | 1.010E−11 |
| MCP1 | MIP3-β | 303 | 3.534E−01 | 2.429E−10 | 1.360E−09 |
| MCP1 | IL-2 | 253 | 3.792E−01 | 4.492E−10 | 2.460E−09 |
| MCP1 | IFN-α protein (pg/mL) | 256 | 3.726E−01 | 7.481E−10 | 4.030E−09 |
| MCP1 | IFN-γ | 256 | 3.664E−01 | 1.489E−09 | 7.730E−09 |
| MCP1 | BAFF | 303 | 3.243E−01 | 7.541E−09 | 3.710E−08 |
| MCP1 | ANG2 | 303 | 3.025E−01 | 7.907E−08 | 3.660E−07 |
| MCP1 | ITAC | 303 | 2.651E−01 | 2.871E−06 | 1.180E−05 |
| MCP1 | BLC | 303 | 2.427E−01 | 1.938E−05 | 7.220E−05 |
| MCP1 | Ficolin 3 | 303 | 2.332E−01 | 4.154E−05 | 1.490E−04 |
| MCP1 | Lymphocyte count | 295 | −1.536E−01 | 8.230E−03 | 1.920E−02 |
| MCP1 | Ferritin | 303 | 1.501E−01 | 8.886E−03 | 2.040E−02 |
| MCP1 | HDLC (mg/dL) | 50 | −3.205E−01 | 2.327E−02 | 4.816E−02 |
| MCP1 | Medium cHDLP (μM) | 50 | −3.150E−01 | 2.589E−02 | 5.220E−02 |
| MCP1 | Eotaxin-2 | 303 | 1.140E−01 | 4.734E−02 | 8.822E−02 |
| MCP1 | Apolipoprotein A1 (mg/dL) | 50 | −2.803E−01 | 4.866E−02 | 9.030E−02 |
| MCP1 | CEC | 129 | −1.645E−01 | 6.242E−02 | 1.101E−01 |
| MCP1 | IgE | 303 | 1.046E−01 | 6.906E−02 | 1.199E−01 |
| MCP1 | cHDLP (μM) | 50 | −2.487E−01 | 8.159E−02 | 1.388E−01 |
| MCP1 | HDL in the H3P size range (μM) | 50 | −2.280E−01 | 1.113E−01 | 1.791E−01 |
| MCP1 | IL1RII | 303 | −6.735E−02 | 2.425E−01 | 3.474E−01 |
| MCP1 | Medium TRLP (nM) | 50 | 1.613E−01 | 2.630E−01 | 3.713E−01 |
| MCP1 | GlycA | 50 | 9.456E−02 | 5.136E−01 | 6.151E−01 |
| MCP1 | IR | 119 | 5.596E−02 | 5.456E−01 | 6.417E−01 |
| MCP1 | NE-DNA | 190 | −3.739E−02 | 6.085E−01 | 7.023E−01 |
| MCP1 | CitH3-DNA | 190 | −2.308E−02 | 7.519E−01 | 8.184E−01 |
| MCP1 | MCP1 | 303 | | 1.000E+00 | |
| Medium TRLP (nM) | IgE | 50 | −3.493E−01 | 1.291E−02 | 2.801E−02 |
| Medium TRLP (nM) | IL-2 | 49 | −3.520E−01 | 1.314E−02 | 2.842E−02 |
| Medium TRLP (nM) | CitH3-DNA | 48 | −2.429E−01 | 9.616E−02 | 1.601E−01 |
| Medium TRLP (nM) | IR | 34 | −2.714E−01 | 1.205E−01 | 1.915E−01 |
| Medium TRLP (nM) | Eotaxin-2 | 50 | 2.089E−01 | 1.455E−01 | 2.257E−01 |
| Medium TRLP (nM) | Medium cHDLP (μM) | 50 | −1.813E−01 | 2.078E−01 | 3.079E−01 |
| Medium TRLP (nM) | ANG2 | 50 | −1.566E−01 | 2.774E−01 | 3.840E−01 |
| Medium TRLP (nM) | NE-DNA | 48 | −1.486E−01 | 3.133E−01 | 4.213E−01 |
| Medium TRLP (nM) | GlycA | 50 | 1.397E−01 | 3.333E−01 | 4.402E−01 |
| Medium TRLP (nM) | Lymphocyte count | 50 | 1.297E−01 | 3.692E−01 | 4.788E−01 |
| Medium TRLP (nM) | Ficolin 3 | 50 | 1.288E−01 | 3.728E−01 | 4.826E−01 |
| Medium TRLP (nM) | cHDLP (μM) | 50 | 1.224E−01 | 3.972E−01 | 5.063E−01 |
| Medium TRLP (nM) | MIP3-β | 50 | 1.221E−01 | 3.983E−01 | 5.066E−01 |
| Medium TRLP (nM) | ITAC | 50 | 1.111E−01 | 4.424E−01 | 5.489E−01 |
| Medium TRLP (nM) | B2M | 49 | 9.137E−02 | 5.324E−01 | 6.323E−01 |
| Medium TRLP (nM) | IP-10 | 50 | −8.998E−02 | 5.343E−01 | 6.331E−01 |
| Medium TRLP (nM) | IL1RII | 50 | 8.504E−02 | 5.571E−01 | 6.526E−01 |
| Medium TRLP (nM) | Ferritin | 50 | 7.971E−02 | 5.821E−01 | 6.750E−01 |
| Medium TRLP (nM) | IFN-α protein (pg/mL) | 50 | 6.873E−02 | 6.353E−01 | 7.242E−01 |
| Medium TRLP (nM) | IFN-γ | 50 | −6.767E−02 | 6.406E−01 | 7.272E−01 |
| Medium TRLP (nM) | IL-10 | 50 | 6.156E−02 | 6.711E−01 | 7.553E−01 |
| Medium TRLP (nM) | BAFF | 50 | −6.133E−02 | 6.722E−01 | 7.556E−01 |
| Medium TRLP (nM) | BLC | 50 | −2.805E−02 | 8.467E−01 | 8.923E−01 |
| Medium TRLP (nM) | HDL in the H3P size range (μM) | 50 | −2.119E−02 | 8.839E−01 | 9.198E−01 |
| Medium TRLP (nM) | CEC | 50 | 1.369E−02 | 9.248E−01 | 9.502E−01 |
| Medium TRLP (nM) | Apolipoprotein A1 (mg/dL) | 50 | 1.175E−02 | 9.354E−01 | 9.532E−01 |
| Medium TRLP (nM) | HDLC (mg/dL) | 50 | −9.902E−03 | 9.456E−01 | 9.578E−01 |
| Medium cHDLP (μM) | HDL in the H3P size range (μM) | 50 | 8.236E−01 | 2.078E−13 | 1.500E−12 |
| Medium cHDLP (μM) | Apolipoprotein A1 (mg/dL) | 50 | 6.058E−01 | 3.142E−06 | 1.280E−05 |
| Medium cHDLP (μM) | HDLC (mg/dL) | 50 | 6.015E−01 | 3.844E−06 | 1.550E−05 |
| Medium cHDLP (μM) | cHDLP (μM) | 50 | 5.537E−01 | 3.028E−05 | 1.100E−04 |
| Medium cHDLP (μM) | CEC | 50 | 4.757E−01 | 4.799E−04 | 1.508E−03 |
| Medium cHDLP (μM) | BAFF | 50 | −4.589E−01 | 8.027E−04 | 2.433E−03 |
| Medium cHDLP (μM) | IFN-α protein (pg/mL) | 50 | −3.430E−01 | 1.476E−02 | 3.162E−02 |
| Medium cHDLP (μM) | MIP3-β | 50 | −2.951E−01 | 3.745E−02 | 7.166E−02 |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
| --- | --- | --- | --- | --- | --- |
| Medium cHDLP (μM) | B2M | 49 | −2.710E−01 | 5.967E−02 | 1.068E−01 |
| Medium cHDLP (μM) | IP-10 | 50 | −2.498E−01 | 8.018E−02 | 1.370E−01 |
| Medium cHDLP (μM) | Ficolin 3 | 50 | 2.200E−01 | 1.248E−01 | 1.961E−01 |
| Medium cHDLP (μM) | ANG2 | 50 | −2.034E−01 | 1.566E−01 | 2.412E−01 |
| Medium cHDLP (μM) | GlycA | 50 | 1.780E−01 | 2.163E−01 | 3.168E−01 |
| Medium cHDLP (μM) | IL-10 | 50 | −1.757E−01 | 2.223E−01 | 3.240E−01 |
| Medium cHDLP (μM) | IL1RII | 50 | 1.757E−01 | 2.224E−01 | 3.240E−01 |
| Medium cHDLP (μM) | BLC | 50 | −1.565E−01 | 2.777E−01 | 3.840E−01 |
| Medium cHDLP (μM) | IR | 34 | 1.797E−01 | 3.091E−01 | 4.165E−01 |
| Medium cHDLP (μM) | IL-2 | 49 | −1.454E−01 | 3.189E−01 | 4.270E−01 |
| Medium cHDLP (μM) | IgE | 50 | 1.331E−01 | 3.567E−01 | 4.639E−01 |
| Medium cHDLP (μM) | CitH3-DNA | 48 | −1.284E−01 | 3.843E−01 | 4.939E−01 |
| Medium cHDLP (μM) | Lymphocyte count | 50 | 1.186E−01 | 4.119E−01 | 5.193E−01 |
| Medium cHDLP (μM) | ITAC | 50 | −6.896E−02 | 6.342E−01 | 7.242E−01 |
| Medium cHDLP (μM) | Ferritin | 50 | −6.845E−02 | 6.367E−01 | 7.242E−01 |
| Medium cHDLP (μM) | NE-DNA | 48 | −5.431E−02 | 7.139E−01 | 7.880E−01 |
| Medium cHDLP (μM) | IFN-γ | 50 | −4.443E−02 | 7.593E−01 | 8.224E−01 |
| Medium cHDLP (μM) | Eotaxin-2 | 50 | 1.196E−02 | 9.343E−01 | 9.532E−01 |
| Medium cHDLP (μM) | Medium cHDLP (μM) | 50 | | 1.000E+00 | |
| MIP3-β | ANG2 | 303 | 5.214E−01 | <E−14 | <E−14 |
| MIP3-β | IL-10 | 254 | 5.853E−01 | <E−14 | <E−14 |
| MIP3-β | BAFF | 303 | 5.928E−01 | <E−14 | <E−14 |
| MIP3-β | IFN-α protein (pg/mL) | 256 | 6.010E−01 | <E−14 | <E−14 |
| MIP3-β | B2M | 302 | 6.184E−01 | <E−14 | <E−14 |
| MIP3-β | ITAC | 303 | 6.191E−01 | <E−14 | <E−14 |
| MIP3-β | IP-10 | 303 | 6.658E−01 | <E−14 | <E−14 |
| MIP3-β | IL-2 | 253 | 4.819E−01 | <E−14 | <E−14 |
| MIP3-β | IFN-γ | 256 | 4.451E−01 | 7.327E−14 | 5.440E−13 |
| MIP3-β | BLC | 303 | 4.016E−01 | 3.568E−13 | 2.520E−12 |
| MIP3-β | Ficolin 3 | 303 | 3.552E−01 | 1.946E−10 | 1.100E−09 |
| MIP3-β | Lymphocyte count | 295 | −3.136E−01 | 3.746E−08 | 1.750E−07 |
| MIP3-β | IgE | 303 | 2.971E−01 | 1.363E−07 | 6.140E−07 |
| MIP3-β | IL1RII | 303 | −2.385E−01 | 2.723E−05 | 9.940E−05 |
| MIP3-β | HDLC (mg/dL) | 50 | −4.251E−01 | 2.091E−03 | 5.846E−03 |
| MIP3-β | cHDLP (μM) | 50 | −4.119E−01 | 2.956E−03 | 7.928E−03 |
| MIP3-β | Ferritin | 303 | 1.678E−01 | 3.393E−03 | 8.989E−03 |
| MIP3-β | HDL in the H3P size range (μM) | 50 | −4.049E−01 | 3.534E−03 | 9.214E−03 |
| MIP3-β | Apolipoprotein A1 (mg/dL) | 50 | −3.964E−01 | 4.376E−03 | 1.095E−02 |
| MIP3-β | NE-DNA | 190 | 1.427E−01 | 4.953E−02 | 9.151E−02 |
| MIP3-β | CEC | 129 | −1.706E−01 | 5.322E−02 | 9.728E−02 |
| MIP3-β | CitH3-DNA | 190 | 1.265E−01 | 8.194E−02 | 1.391E−01 |
| MIP3-β | Eotaxin-2 | 303 | −6.681E−02 | 2.463E−01 | 3.505E−01 |
| MIP3-β | GlycA | 50 | −8.395E−02 | 5.622E−01 | 6.567E−01 |
| MIP3-β | IR | 119 | 1.557E−02 | 8.665E−01 | 9.087E−01 |
| Lymphocyte count | IFN-α protein (pg/mL) | 251 | −4.754E−01 | <E−14 | 1.090E−14 |
| Lymphocyte count | BLC | 295 | −4.307E−01 | <E−14 | 7.430E−14 |
| Lymphocyte count | IL-10 | 249 | −4.603E−01 | 1.821E−14 | 1.400E−13 |
| Lymphocyte count | BAFF | 295 | −4.210E−01 | 4.219E−14 | 3.160E−13 |
| Lymphocyte count | IP-10 | 295 | −3.986E−01 | 1.119E−12 | 7.580E−12 |
| Lymphocyte count | B2M | 294 | −3.443E−01 | 1.327E−09 | 6.920E−09 |
| Lymphocyte count | ITAC | 295 | −3.145E−01 | 3.397E−08 | 1.610E−07 |
| Lymphocyte count | Ficolin 3 | 295 | −2.691E−01 | 2.740E−06 | 1.130E−05 |
| Lymphocyte count | IFN-γ | 251 | −2.796E−01 | 6.865E−06 | 2.710E−05 |
| Lymphocyte count | IL-2 | 248 | −2.809E−01 | 7.062E−06 | 2.780E−05 |
| Lymphocyte count | ANG2 | 295 | −2.470E−01 | 1.781E−05 | 6.730E−05 |
| Lymphocyte count | IL1RII | 295 | 1.855E−01 | 1.373E−03 | 4.050E−03 |
| Lymphocyte count | IgE | 295 | −1.472E−01 | 1.136E−02 | 2.508E−02 |
| Lymphocyte count | cHDLP (μM) | 50 | 2.227E−01 | 1.200E−01 | 1.910E−01 |
| Lymphocyte count | HDL in the H3P size range (M) | 50 | 1.872E−01 | 1.929E−01 | 2.888E−01 |
| Lymphocyte count | GlycA | 50 | −1.777E−01 | 2.169E−01 | 3.171E−01 |
| Lymphocyte count | HDLC (mg/dL) | 50 | 1.731E−01 | 2.292E−01 | 3.317E−01 |
| Lymphocyte count | Ferritin | 295 | −6.942E−02 | 2.345E−01 | 3.382E−01 |
| Lymphocyte count | Apolipoprotein A1 (mg/dL) | 50 | 1.691E−01 | 2.405E−01 | 3.456E−01 |
| Lymphocyte count | IR | 121 | −1.066E−01 | 2.444E−01 | 3.496E−01 |
| Lymphocyte count | Eotaxin-2 | 295 | 6.683E−02 | 2.525E−01 | 3.582E−01 |
| Lymphocyte count | CitH3-DNA | 184 | −4.686E−02 | 5.276E−01 | 6.283E−01 |
| Lymphocyte count | CEC | 128 | 2.956E−02 | 7.405E−01 | 8.092E−01 |
| Lymphocyte count | NE-DNA | 184 | −1.583E−02 | 8.311E−01 | 8.802E−01 |
| Lymphocyte count | Lymphocyte count | 298 | | 1.000E+00 | |
| IL-2 | B2M | 252 | 4.884E−01 | <E−14 | <E−14 |
| IL-2 | IL-10 | 253 | 5.185E−01 | <E−14 | <E−14 |
| IL-2 | IP-10 | 253 | 5.577E−01 | <E−14 | <E−14 |
| IL-2 | IFN-γ | 253 | 5.654E−01 | <E−14 | <E−14 |
| IL-2 | ITAC | 253 | 4.813E−01 | <E−14 | <E−14 |
| IL-2 | IFN-α protein (pg/mL) | 253 | 4.314E−01 | 6.892E−13 | 4.750E−12 |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
|---|---|---|---|---|---|
| IL-2 | BAFF | 253 | 4.199E-01 | 3.149E-12 | 1.990E-11 |
| IL-2 | BLC | 253 | 3.806E-01 | 3.810E-10 | 2.100E-09 |
| IL-2 | ANG2 | 253 | 3.604E-01 | 3.561E-09 | 1.810E-08 |
| IL-2 | IL1RII | 253 | -2.335E-01 | 1.786E-04 | 5.961E-04 |
| IL-2 | Eotaxin-2 | 253 | -1.965E-01 | 1.685E-03 | 4.804E-03 |
| IL-2 | Ficolin 3 | 253 | 1.805E-01 | 3.979E-03 | 1.017E-02 |
| IL-2 | IgE | 253 | 1.672E-01 | 7.706E-03 | 1.813E-02 |
| IL-2 | CitH3-DNA | 182 | 1.868E-01 | 1.155E-02 | 2.544E-02 |
| IL-2 | IR | 105 | 2.441E-01 | 1.209E-02 | 2.643E-02 |
| IL-2 | cHDLP (µM) | 49 | -3.035E-01 | 3.404E-02 | 6.616E-02 |
| IL-2 | CEC | 124 | -1.827E-01 | 4.228E-02 | 7.984E-02 |
| IL-2 | HDL in the H3P size range (µM) | 49 | -2.791E-01 | 5.211E-02 | 9.547E-02 |
| IL-2 | Apolipoprotein A1 (mg/dL) | 49 | -2.760E-01 | 5.495E-02 | 1.002E-01 |
| IL-2 | NE-DNA | 182 | 1.396E-01 | 6.018E-02 | 1.075E-01 |
| IL-2 | HDLC (mg/dL) | 49 | -2.685E-01 | 6.208E-02 | 1.098E-01 |
| IL-2 | GlycA | 49 | -1.351E-01 | 3.547E-01 | 4.620E-01 |
| IL-2 | Ferritin | 253 | 9.104E-03 | 8.854E-01 | 9.198E-01 |
| IL1RII | IFN-α protein (pg/mL) | 256 | -3.571E-01 | 4.077E-09 | 2.050E-08 |
| IL1RII | Eotaxin-2 | 303 | 2.414E-01 | 2.152E-05 | 7.950E-05 |
| IL1RII | IP-10 | 303 | -2.352E-01 | 3.535E-05 | 1.279E-04 |
| IL1RII | IFN-γ | 256 | -1.961E-01 | 1.613E-03 | 4.631E-03 |
| IL1RII | ITAC | 303 | -1.767E-01 | 2.019E-03 | 5.680E-03 |
| IL1RII | CEC | 129 | 2.448E-01 | 5.176E-03 | 1.263E-02 |
| IL1RII | BAFF | 303 | -1.585E-01 | 5.687E-03 | 1.376E-02 |
| IL1RII | HDL in the H3P size range (µM) | 50 | 3.764E-01 | 7.052E-03 | 1.673E-02 |
| IL1RII | NE-DNA | 190 | -1.921E-01 | 7.920E-03 | 1.858E-02 |
| IL1RII | CitH3-DNA | 190 | -1.823E-01 | 1.183E-02 | 2.598E-02 |
| IL1RII | ANG2 | 303 | -1.443E-01 | 1.192E-02 | 2.611E-02 |
| IL1RII | Apolipoprotein A1 (mg/dL) | 50 | 3.022E-01 | 3.293E-02 | 6.444E-02 |
| IL1RII | cHDLP (µM) | 50 | 2.955E-01 | 3.724E-02 | 7.141E-02 |
| IL1RII | IR | 119 | 1.708E-01 | 6.334E-02 | 1.115E-01 |
| IL1RII | HDLC (mg/dL) | 50 | 2.496E-01 | 8.050E-02 | 1.372E-01 |
| IL1RII | BLC | 303 | -9.741E-02 | 9.054E-02 | 1.518E-01 |
| IL1RII | B2M | 302 | -8.861E-02 | 1.244E-01 | 1.960E-01 |
| IL1RII | Ficolin 3 | 303 | -7.378E-02 | 2.003E-01 | 2.984E-01 |
| IL1RII | GlycA | 50 | 1.562E-01 | 2.786E-01 | 3.844E-01 |
| IL1RII | IgE | 303 | -5.886E-02 | 3.071E-01 | 4.158E-01 |
| IL1RII | Ferritin | 303 | 4.362E-03 | 9.397E-01 | 9.546E-01 |
| ITAC | IgE | 303 | 4.832E-01 | <E-14 | <E-14 |
| ITAC | BAFF | 303 | 5.209E-01 | <E-14 | <E-14 |
| ITAC | ANG2 | 303 | 5.710E-01 | <E-14 | <E-14 |
| ITAC | B2M | 302 | 5.804E-01 | <E-14 | <E-14 |
| ITAC | IFN-α protein (pg/mL) | 256 | 5.922E-01 | <E-14 | <E-14 |
| ITAC | IP-10 | 303 | 7.055E-01 | <E-14 | <E-14 |
| ITAC | IFN-γ | 256 | 4.568E-01 | 1.332E-14 | 1.030E-13 |
| ITAC | BLC | 303 | 4.116E-01 | 8.127E-14 | 5.980E-13 |
| ITAC | Ficolin 3 | 303 | 3.447E-01 | 7.015E-10 | 3.800E-09 |
| ITAC | CitH3-DNA | 190 | 2.747E-01 | 1.255E-04 | 4.304E-04 |
| ITAC | Eotaxin-2 | 303 | -1.670E-01 | 3.542E-03 | 9.214E-03 |
| ITAC | NE-DNA | 190 | 1.980E-01 | 6.187E-03 | 1.484E-02 |
| ITAC | CEC | 129 | -1.955E-01 | 2.641E-02 | 5.293E-02 |
| ITAC | HDLC (mg/dL) | 50 | -2.682E-01 | 5.966E-02 | 1.068E-01 |
| ITAC | Apolipoprotein A1 (mg/dL) | 50 | -2.293E-01 | 1.093E-01 | 1.765E-01 |
| ITAC | cHDLP (µM) | 50 | -2.197E-01 | 1.253E-01 | 1.965E-01 |
| ITAC | Ferritin | 303 | 7.916E-02 | 1.693E-01 | 2.590E-01 |
| ITAC | HDL in the H3P size range (µM) | 50 | -1.401E-01 | 3.317E-01 | 4.387E-01 |
| ITAC | GlycA | 50 | 8.993E-02 | 5.346E-01 | 6.331E-01 |
| ITAC | IR | 119 | 3.070E-02 | 7.403E-01 | 8.092E-01 |
| ITAC | ITAC | 303 | | 1.000E+00 | |
| IFN-γ | IP-10 | 256 | 5.626E-01 | <E-14 | <E-14 |
| IFN-γ | IFN-α protein (pg/mL) | 256 | 4.224E-01 | 1.673E-12 | 1.080E-11 |
| IFN-γ | B2M | 255 | 4.020E-01 | 2.538E-11 | 1.530E-10 |
| IFN-γ | BAFF | 256 | 3.274E-01 | 8.275E-08 | 3.810E-07 |
| IFN-γ | BLC | 256 | 2.991E-01 | 1.093E-06 | 4.660E-06 |
| IFN-γ | ANG2 | 256 | 2.518E-01 | 4.600E-05 | 1.637E-04 |
| IFN-γ | Eotaxin-2 | 256 | -2.323E-01 | 1.763E-04 | 5.906E-04 |
| IFN-γ | IgE | 256 | 2.142E-01 | 5.599E-04 | 1.734E-03 |
| IFN-γ | Ficolin 3 | 256 | 1.891E-01 | 2.377E-03 | 6.538E-03 |
| IFN-γ | CitH3-DNA | 185 | 1.898E-01 | 9.682E-03 | 2.171E-02 |
| IFN-γ | NE-DNA | 185 | 1.686E-01 | 2.179E-02 | 4.555E-02 |
| IFN-γ | cHDLP (µM) | 50 | -2.872E-01 | 4.318E-02 | 8.118E-02 |
| IFN-γ | Apolipoprotein A1 (mg/dL) | 50 | -1.545E-01 | 2.840E-01 | 3.900E-01 |
| IFN-γ | Ferritin | 256 | 6.190E-02 | 3.239E-01 | 4.310E-01 |
| IFN-γ | IR | 106 | 8.302E-02 | 3.975E-01 | 5.063E-01 |
| IFN-γ | HDLC (mg/dL) | 50 | -1.218E-01 | 3.994E-01 | 5.072E-01 |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
| --- | --- | --- | --- | --- | --- |
| IFN-γ | HDL in the H3P size range (μM) | 50 | −8.834E−02 | 5.418E−01 | 6.382E−01 |
| IFN-γ | CEC | 127 | −3.366E−02 | 7.072E−01 | 7.836E−01 |
| IFN-γ | GlycA | 50 | −3.757E−02 | 7.956E−01 | 8.520E−01 |
| IP-10 | BLC | 303 | 4.661E−01 | <E−14 | <E−14 |
| IP-10 | ANG2 | 303 | 5.811E−01 | <E−14 | <E−14 |
| IP-10 | BAFF | 303 | 5.878E−01 | <E−14 | <E−14 |
| IP-10 | B2M | 302 | 6.266E−01 | <E−14 | <E−14 |
| IP-10 | IFN-α protein (pg/mL) | 256 | 6.268E−01 | <E−14 | <E−14 |
| IP-10 | IgE | 303 | 3.997E−01 | 4.712E−13 | 3.270E−12 |
| IP-10 | Ficolin 3 | 303 | 2.824E−01 | 5.792E−07 | 2.520E−06 |
| IP-10 | cHDLP (μM) | 50 | −5.577E−01 | 2.583E−05 | 9.470E−05 |
| IP-10 | Apolipoprotein A1 (mg/dL) | 50 | −5.112E−01 | 1.482E−04 | 5.065E−04 |
| IP-10 | HDLC (mg/dL) | 50 | −4.995E−01 | 2.218E−04 | 7.235E−04 |
| IP-10 | Eotaxin-2 | 303 | −1.738E−01 | 2.392E−03 | 6.558E−03 |
| IP-10 | Ferritin | 303 | 1.613E−01 | 4.880E−03 | 1.197E−02 |
| IP-10 | NE-DNA | 190 | 1.749E−01 | 1.582E−02 | 3.355E−02 |
| IP-10 | CEC | 129 | −1.983E−01 | 2.430E−02 | 4.969E−02 |
| IP-10 | CitH3-DNA | 190 | 1.548E−01 | 3.293E−02 | 6.444E−02 |
| IP-10 | HDL in the H3P size range (μM) | 50 | −2.960E−01 | 3.688E−02 | 7.088E−02 |
| IP-10 | IR | 119 | 1.093E−01 | 2.368E−01 | 3.409E−01 |
| IP-10 | GlycA | 50 | 1.071E−01 | 4.589E−01 | 5.661E−01 |
| IP-10 | IP-10 | 303 | | 1.000E+00 | |
| IgE | ANG2 | 303 | 4.074E−01 | 1.519E−13 | 1.110E−12 |
| IgE | B2M | 302 | 3.694E−01 | 3.363E−11 | 2.010E−10 |
| IgE | BAFF | 303 | 2.567E−01 | 6.027E−06 | 2.390E−05 |
| IgE | Ficolin 3 | 303 | 2.448E−01 | 1.631E−05 | 6.200E−05 |
| IgE | NE-DNA | 190 | 2.301E−01 | 1.402E−03 | 4.105E−03 |
| IgE | Eotaxin-2 | 303 | −1.640E−01 | 4.213E−03 | 1.064E−02 |
| IgE | CitH3-DNA | 190 | 2.037E−01 | 4.824E−03 | 1.190E−02 |
| IgE | BLC | 303 | 1.404E−01 | 1.447E−02 | 3.107E−02 |
| IgE | CEC | 129 | −2.038E−01 | 2.053E−02 | 4.311E−02 |
| IgE | Ferritin | 303 | 6.664E−02 | 2.475E−01 | 3.517E−01 |
| IgE | IR | 119 | 4.844E−02 | 6.009E−01 | 6.945E−01 |
| IgE | cHDLP (μM) | 50 | −7.381E−02 | 6.105E−01 | 7.036E−01 |
| IgE | GlycA | 50 | 5.030E−02 | 7.287E−01 | 8.023E−01 |
| IgE | HDL in the H3P size range (μM) | 50 | −1.629E−02 | 9.106E−01 | 9.424E−01 |
| IgE | Apolipoprotein A1 (mg/dL) | 50 | −1.282E−02 | 9.296E−01 | 9.528E−01 |
| IgE | HDLC (mg/dL) | 50 | 4.455E−03 | 9.755E−01 | 9.812E−01 |
| IgE | IgE | 303 | | 1.000E+00 | |
| IR | Ficolin 3 | 119 | 1.697E−01 | 6.506E−02 | 1.141E−01 |
| IR | CEC | 79 | −2.083E−01 | 6.547E−02 | 1.146E−01 |
| IR | Eotaxin-2 | 119 | −1.478E−01 | 1.086E−01 | 1.761E−01 |
| IR | GlycA | 34 | 2.727E−01 | 1.187E−01 | 1.900E−01 |
| IR | HDL in the H3P size range (μM) | 34 | 2.242E−01 | 2.024E−01 | 3.009E−01 |
| IR | BLC | 119 | 9.916E−02 | 2.833E−01 | 3.896E−01 |
| IR | Apolipoprotein A1 (mg/dL) | 34 | 1.643E−01 | 3.531E−01 | 4.607E−01 |
| IR | Ferritin | 119 | −7.918E−02 | 3.920E−01 | 5.030E−01 |
| IR | CitH3-DNA | 76 | 9.392E−02 | 4.196E−01 | 5.252E−01 |
| IR | BAFF | 119 | −6.795E−02 | 4.628E−01 | 5.700E−01 |
| IR | cHDLP (μM) | 34 | 1.246E−01 | 4.828E−01 | 5.904E−01 |
| IR | NE-DNA | 76 | 5.870E−02 | 6.145E−01 | 7.064E−01 |
| IR | ANG2 | 119 | −3.768E−02 | 6.841E−01 | 7.640E−01 |
| IR | B2M | 118 | 3.278E−02 | 7.245E−01 | 7.987E−01 |
| IR | HDLC (mg/dL) | 34 | 4.339E−02 | 8.075E−01 | 8.595E−01 |
| HDLC (mg/dL) | Apolipoprotein A1 (mg/dL) | 50 | 9.651E−01 | <E−14 | <E−14 |
| HDLC (mg/dL) | cHDLP (μM) | 50 | 8.071E−01 | 1.456E−12 | 9.570E−12 |
| HDLC (mg/dL) | HDL in the H3P size range (μM) | 50 | 5.788E−01 | 1.068E−05 | 4.140E−05 |
| HDLC (mg/dL) | CEC | 50 | 5.073E−01 | 1.698E−04 | 5.709E−04 |
| HDLC (mg/dL) | ANG2 | 50 | −4.289E−01 | 1.883E−03 | 5.352E−03 |
| HDLC (mg/dL) | BAFF | 50 | −4.156E−01 | 2.690E−03 | 7.284E−03 |
| HDLC (mg/dL) | Eotaxin-2 | 50 | 3.156E−01 | 2.559E−02 | 5.172E−02 |
| HDLC (mg/dL) | Ferritin | 50 | −2.910E−01 | 4.032E−02 | 7.647E−02 |
| HDLC (mg/dL) | CitH3-DNA | 48 | −2.856E−01 | 4.907E−02 | 9.086E−02 |
| HDLC (mg/dL) | BLC | 50 | −2.325E−01 | 1.042E−01 | 1.715E−01 |
| HDLC (mg/dL) | B2M | 49 | −1.470E−01 | 3.136E−01 | 4.213E−01 |
| HDLC (mg/dL) | GlycA | 50 | −8.003E−02 | 5.806E−01 | 6.746E−01 |
| HDLC (mg/dL) | Ficolin 3 | 50 | −5.727E−02 | 6.928E−01 | 7.707E−01 |
| HDL in the H3P size range (μM) | Apolipoprotein A1 (mg/dL) | 50 | 6.216E−01 | 1.450E−06 | 6.150E−06 |
| HDL in the H3P size range (μM) | cHDLP (μM) | 50 | 5.397E−01 | 5.240E−05 | 1.857E−04 |
| HDL in the H3P size range (μM) | BAFF | 50 | −4.888E−01 | 3.158E−04 | 1.011E−03 |
| HDL in the H3P size range (μM) | CEC | 50 | 4.233E−01 | 2.193E−03 | 6.111E−03 |
| HDL in the H3P size range (μM) | ANG2 | 50 | −2.718E−01 | 5.618E−02 | 1.016E−01 |
| HDL in the H3P size range (μM) | GlycA | 50 | 2.600E−01 | 6.825E−02 | 1.190E−01 |
| HDL in the H3P size range (μM) | BLC | 50 | −2.053E−01 | 1.527E−01 | 2.361E−01 |
| HDL in the H3P size range (μM) | B2M | 49 | −1.899E−01 | 1.912E−01 | 2.868E−01 |

TABLE 7-2-continued

The correlation between analyte pairs was analyzed using Spearman's rank correlation.
Analyte pairs with a false-discovery rate (FDR) of <0.05 are indicated by bold text.

| Analyte | Analyte | n | rho | P value | FDR |
|---|---|---|---|---|---|
| HDL in the H3P size range (μM) | Eotaxin-2 | 50 | 1.593E−01 | 2.690E−01 | 3.779E−01 |
| HDL in the H3P size range (μM) | CitH3-DNA | 48 | −1.570E−01 | 2.865E−01 | 3.928E−01 |
| HDL in the H3P size range (μM) | Ficolin 3 | 50 | 1.003E−01 | 4.882E−01 | 5.924E−01 |
| HDL in the H3P size range (μM) | Ferritin | 50 | −1.525E−02 | 9.163E−01 | 9.437E−01 |
| HDL in the H3P size range (μM) | HDL in the H3P size range (μM) | 50 | | 1.000E+00 | |
| Ficolin 3 | B2M | 302 | 3.544E−01 | 2.292E−10 | 1.290E−09 |
| Ficolin 3 | Ferritin | 303 | 3.304E−01 | 3.770E−09 | 1.910E−08 |
| Ficolin 3 | BAFF | 303 | 2.844E−01 | 4.781E−07 | 2.090E−06 |
| Ficolin 3 | ANG2 | 303 | 2.534E−01 | 7.975E−06 | 3.110E−05 |
| Ficolin 3 | BLC | 303 | 2.026E−01 | 3.875E−04 | 1.226E−03 |
| Ficolin 3 | Eotaxin-2 | 303 | −7.217E−02 | 2.103E−01 | 3.101E−01 |
| Ficolin 3 | CitH3-DNA | 190 | 7.733E−02 | 2.889E−01 | 3.949E−01 |
| Ficolin 3 | cHDLP (μM) | 50 | 8.726E−02 | 5.468E−01 | 6.423E−01 |
| Ficolin 3 | CEC | 129 | −1.722E−02 | 8.464E−01 | 8.923E−01 |
| Ficolin 3 | Apolipoprotein A1 (mg/dL) | 50 | 9.864E−04 | 9.946E−01 | 9.946E−01 |
| Ficolin 3 | Ficolin 3 | 303 | | 1.000E+00 | |
| Ferritin | B2M | 302 | 2.612E−01 | 4.226E−06 | 1.700E−05 |
| Ferritin | ANG2 | 303 | 1.724E−01 | 2.601E−03 | 7.064E−03 |
| Ferritin | Apolipoprotein A1 (mg/dL) | 50 | −3.016E−01 | 3.330E−02 | 6.486E−02 |
| Ferritin | cHDLP (μM) | 50 | −2.897E−01 | 4.128E−02 | 7.811E−02 |
| Ferritin | BAFF | 303 | 1.160E−01 | 4.356E−02 | 8.171E−02 |
| Ferritin | CitH3-DNA | 190 | −2.981E−02 | 6.831E−01 | 7.640E−01 |
| Ferritin | BLC | 303 | 2.369E−02 | 6.813E−01 | 7.640E−01 |
| Ferritin | Eotaxin-2 | 303 | 1.957E−02 | 7.344E−01 | 8.055E−01 |
| Ferritin | CEC | 129 | 1.675E−02 | 8.505E−01 | 8.942E−01 |
| Eotaxin-2 | CitH3-DNA | 190 | −2.406E−01 | 8.283E−04 | 2.502E−03 |
| Eotaxin-2 | Apolipoprotein A1 (mg/dL) | 50 | 3.136E−01 | 2.656E−02 | 5.305E−02 |
| Eotaxin-2 | cHDLP (μM) | 50 | 2.782E−01 | 5.044E−02 | 9.281E−02 |
| Eotaxin-2 | CEC | 129 | 1.650E−01 | 6.171E−02 | 1.096E−01 |
| Eotaxin-2 | ANG2 | 303 | −9.977E−02 | 8.295E−02 | 1.406E−01 |
| Eotaxin-2 | BAFF | 303 | −8.212E−02 | 1.539E−01 | 2.375E−01 |
| Eotaxin-2 | B2M | 302 | 4.808E−02 | 4.051E−01 | 5.137E−01 |
| Eotaxin-2 | BLC | 303 | −3.804E−02 | 5.095E−01 | 6.110E−01 |
| Eotaxin-2 | Eotaxin-2 | 303 | | 1.000E+00 | |
| cHDLP (μM) | Apolipoprotein A1 (mg/dL) | 50 | 8.885E−01 | <E−14 | <E−14 |
| cHDLP (μM) | BAFF | 50 | −3.982E−01 | 4.183E−03 | 1.059E−02 |
| cHDLP (μM) | CEC | 50 | 3.833E−01 | 6.002E−03 | 1.448E−02 |
| cHDLP (μM) | ANG2 | 50 | −3.270E−01 | 2.046E−02 | 4.307E−02 |
| cHDLP (μM) | B2M | 49 | −3.059E−01 | 3.253E−02 | 6.394E−02 |
| cHDLP (μM) | BLC | 50 | −2.377E−01 | 9.651E−02 | 1.604E−01 |
| cHDLP (μM) | cHDLP (μM) | 50 | | 1.000E+00 | |
| B2M | ANG2 | 302 | 5.034E−01 | <E−14 | <E−14 |
| B2M | BAFF | 302 | 5.400E−01 | <E−14 | <E−14 |
| B2M | BLC | 302 | 3.458E−01 | 6.604E−10 | 3.600E−09 |
| B2M | Apolipoprotein A1 (mg/dL) | 49 | −1.627E−01 | 2.640E−01 | 3.720E−01 |
| B2M | B2M | 302 | | 1.000E+00 | |
| BLC | ANG2 | 303 | 3.772E−01 | 1.106E−11 | 6.900E−11 |
| BLC | BAFF | 303 | 3.552E−01 | 1.946E−10 | 1.100E−09 |
| BLC | Apolipoprotein A1 (mg/dL) | 50 | −2.438E−01 | 8.803E−02 | 1.480E−01 |
| BAFF | ANG2 | 303 | 5.373E−01 | <E−14 | <E−14 |
| BAFF | Apolipoprotein A1 (mg/dL) | 50 | −4.085E−01 | 3.232E−03 | 8.641E−03 |
| BAFF | BAFF | 303 | | 1.000E+00 | |
| Apolipoprotein A1 (mg/dL) | ANG2 | 50 | −3.968E−01 | 4.335E−03 | 1.091E−02 |
| ANG2 | ANG2 | 303 | | 1.000E+00 | |

Figure 5A:
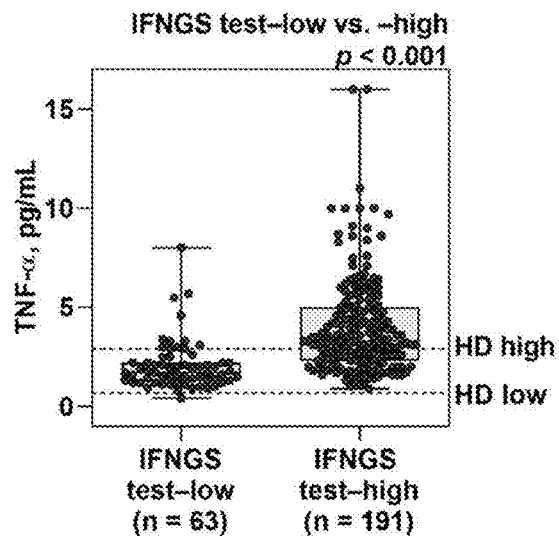
Figure 5B:
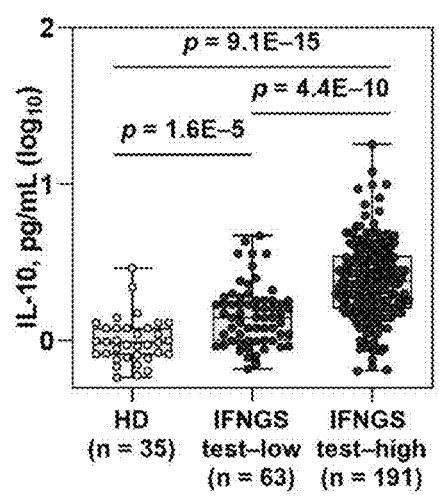

7.3.2 Cytokines Associated with Vascular Dysfunction are Modulated by Anifrolumab Type I IFN signalling and NET formation directly impact the vasculature and were upregulated in SLE. Serum TNF-α was elevated in IFNGS test-high patients compared with IFNGS test-low patients (p<0.001; FIG. 5A). The median TNF-α concentration in IFNGS test-high patients was above the range of healthy donors, but not in IFNGS test-low patients. TNF-α, 21-IFNGS, and IFN-α protein significantly correlated in SLE (FIG. 3, Table 7-2). IFNGS test-high patients had elevated IL-10 compared with those who were IFNGS test-low (p=4.4E−10; FIG. 5B). Similar to TNF-α, serum IL-10 levels correlated with 21-IFNGS (R=0.506, p<E−14) and serum IFN-α protein levels (R=0.549, p<E−14; FIG. 3, Table 7-2). TNF-α and IL-10 levels were correlated (R=0.732, p<E−14; Table 7-2). Together, these results demonstrate an association between TNF-α, IL-10, and type I IFN signalling, three putative key mediators of vascular dysfunction in SLE.

Figure 5C:
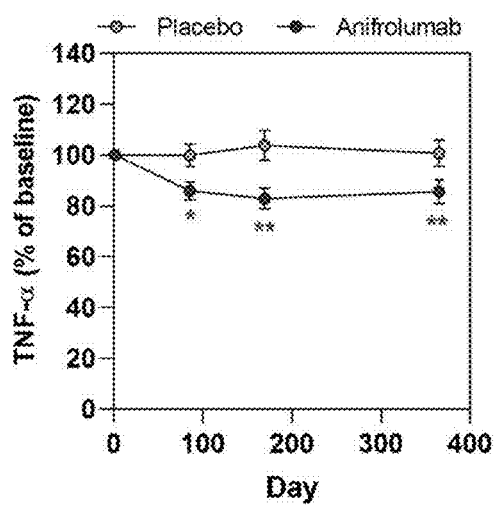
Figure 5D:
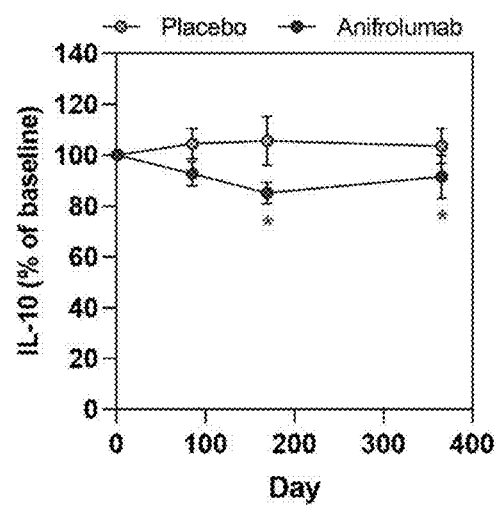

TNF-α and IL-10 significantly decreased in IFNGS test-high patients after anifrolumab compared with placebo at various timepoints (FIG. 5C-D). In IFNGS test-high patients, but not in IFNGS test-low patients, IL-10 levels decreased with anifrolumab compared with placebo at days 169 (p=0.037) and 365 (p=0.016). Overall, anifrolumab significantly decreased TNF-α and IL-10 levels.

7.3.3 Inhibition of Type I IFN Signalling Modulates Cardiometabolic Disease Markers Given that NETs can oxidize HDL and impact CEC, the impact of NET inhibition with anifrolumab on these parameters was assessed. Baseline CEC values were significantly reduced in SLE compared with healthy donors in both IFNGS test-low and test-high patients, suggesting proatherogenic dysregulation of HDL function (FIG. 6A). While multiple proinflammatory and proatherogenic proteins associated with the type I IFN pathway (Table 7-1), no association between CEC and IFNGS test status was found, serum IFN-α, or 21-IFNGS in this cohort (FIG. 3, Table 7-2). In contrast, a significant negative correlation between CEC and circulating NET complex levels was observed (FIG. 6B) consistent with aberrant HDL function resulting from neutrophil-mediated oxidation.

To investigate whether anifrolumab could improve impaired (≥2 standard deviations [SD] below healthy donor mean) CEC, CEC levels of those patients were measured before and after treatment (FIG. 7). In IFNGS test-high patients receiving anifrolumab, and not in the IFNGS test-low or placebo groups, CEC increased significantly (17.3%) at day 365 compared with baseline (p<0.001; FIG. 6C). This effect was more pronounced in patients with highest CEC impairments at baseline (FIG. 8). CEC was not altered by corticosteroid tapering alone (FIG. 9).

Lipoprotein levels were quantified (including particle count and size) by NMR in IFNGS test-high SLE. HDL cholesterol (HDL-C), HDL in the H3P size range, HDL particle count (cHDLP), medium cHDLP, apolipoprotein A-1, and very large triglyceride-rich lipoprotein particles (TRLP) were significantly lower in SLE patients than in healthy donors, whereas medium TRLP was significantly higher (Table 7-3). Statistical significance was assessed using a Mann-Whitney U test, parameters above the thick line indicate p<0.05.

TABLE 7-3

Baseline lipid parameters in patients with SLE

| Analyte | AUC | P-value | FDR |
|---|---|---|---|
| H3P (μmol/L) | 0.15 | 5.56E−04 | 1.83E−02 |
| Medium high-density lipoprotein (HDL) particle count (cHDLP) (μmol/L) | 0.18 | 1.45E−03 | 2.39E−02 |
| Medium triglyceride-rich lipoprotein particle (TRLP) (nmol/L) | 0.76 | 1.11E−02 | 1.05E−01 |
| Apolipoprotein A-1 (mg/dL) | 0.25 | 1.35E−02 | 1.05E−01 |
| Very large TRLP (nmol/L) | 0.28 | 1.58E−02 | 1.05E−01 |
| HDL count (HDL-C) (mg/dL) | 0.28 | 2.76E−02 | 1.52E−01 |
| cHDLP (μmol/L) | 0.29 | 4.20E−02 | 1.98E−01 |
| Very small TRLP (nmol/L) | 0.31 | 6.35E−02 | 2.33E−01 |
| Total cholesterol (TC) (mg/dL) | 0.31 | 6.36E−02 | 2.33E−01 |
| Small cHDLP (μmol/L) | 0.66 | 1.15E−01 | 3.79E−01 |
| Low-density lipoprotein (LDL) count (LDLC) (mg/dL) | 0.36 | 1.56E−01 | 4.29E−01 |
| LDL particle (LDLP) count (cLDLP) (nmol/L) | 0.36 | 1.56E−01 | 4.29E−01 |
| Triglyceride-rich lipoprotein (TRL)-triglyceride (TRLTG) (mg/dL) | 0.64 | 1.84E−01 | 4.66E−01 |
| Large cHDLP (μmol/L) | 0.37 | 2.11E−01 | 4.98E−01 |
| H6P (μmol/L) | 0.38 | 2.37E−01 | 5.21E−01 |
| Triglycerides (TG) (mg/dL) | 0.61 | 2.89E−01 | 5.34E−01 |
| H1P (μmol/L) | 0.60 | 3.25E−01 | 5.34E−01 |
| H2P (μmol/L) | 0.59 | 3.56E−01 | 5.34E−01 |
| Apolipoprotein B (mg/dL) | 0.41 | 3.72E−01 | 5.34E−01 |
| Medium cLDLP (nmol/L) | 0.41 | 3.76E−01 | 5.34E−01 |
| H123 (μmol/L) | 0.41 | 3.77E−01 | 5.34E−01 |
| H5P (μmol/L) | 0.41 | 3.87E−01 | 5.34E−01 |
| Small TRLP (nmol/L) | 0.59 | 3.94E−01 | 5.34E−01 |
| HDL size (nm) | 0.42 | 4.03E−01 | 5.34E−01 |
| TRL count (TRLC) (mg/dL) | 0.59 | 4.04E−01 | 5.34E−01 |
| Large cLDLP (nmol/L) | 0.43 | 5.06E−01 | 6.43E−01 |
| H7P (μmol/L) | 0.56 | 5.57E−01 | 6.72E−01 |
| LDL size (nm) | 0.44 | 5.70E−01 | 6.72E−01 |
| Small cLDLP (nmol/L) | 0.45 | 6.13E−01 | 6.94E−01 |
| Large TRLP (nmol/L) | 0.55 | 6.31E−01 | 6.94E−01 |

TABLE 7-3-continued

Baseline lipid parameters in patients with SLE

| Analyte | AUC | P-value | FDR |
|---|---|---|---|
| H4P (μmol/L) | 0.52 | 8.35E−01 | 8.89E−01 |
| TRLP (nmol/L) | 0.52 | 8.82E−01 | 9.09E−01 |
| TRL size (nm) | 0.49 | 9.13E−01 | 9.13E−01 |

The correlations between HDL-C and total cholesterol with IFN-α protein were assessed using 21-IFNGS, and IFNGS test. IFNGS test-high patients had reduced levels of total cholesterol and HDL-C compared with IFNGS test-low patients (FIG. 3). Total cholesterol and HDL-C negatively correlated with 21-IFNGS and IFN-α. Traditional CVD risk factors like body mass index (BMI) and age also inversely associated with type I IFN measures. Patients who were IFNGS test-high had significantly decreased body mass index (BMIs) compared with those who were IFNGS test-low (p=0.000136). BMI also negatively correlated with IFN 21-gene signature and IFN-α protein (IFN 21-gene signature: R=−0.17303, p=0.002508; IFN-α: R=−0.14517, p=0.0144). Patients who were IFNGS test-high were younger than patients who were IFNGS-test low, and age also negatively correlated with IFN 21-gene signature and IFN-α protein (IFNGS test-status: p=0.00527; IFN 21-gene signature: R=−0.25517, p=6.86E-6; IFN-α: R=−0.2918, p=0.000179). There was no association between smoking status and the type I IFN measures. These results indicate that, although IFNGS test-high patients had reduced traditional CVD risk factors (age, BMI, total cholesterol) compared with IFNGS test-low patients, they had increased immune markers of vascular dysfunction and neutrophil dysregulation and lower levels of HDL-C, supporting elevated CVD risk that is not predicted by traditional CVD risk factors alone.

To further examine the association between lipoprotein/lipid parameters and type I IFN pathway, the effect of anifrolumab on lipid parameters were evaluated for which there were ≥10 patients with baseline lipid defects (measurements≥2 SD from healthy donor mean; Table 5-1). Lipid parameters were assessed by NMR LipoProfile® in patients with SLE to calculate median change at day 365 compared with day 1. A signed-rank test was used to compare longitudinal median changes. In patients with reduced baseline HDL in the H3P size range, H3P levels significantly increased from baseline after anifrolumab (p=0.0223) but not placebo. There were no significant, treatment-specific changes in medium, small, or very small TRLP.

TABLE 7-4

Longitudinal changes in lipid NMR measurements after type I IFN inhibition in patients with SLE with a baseline NMR defect[a]

| Median change Signed rank test p-value Lipid analyte (n = placebo, anifrolumab) | Placebo | Anifrolumab 300 mg | Placebo | Anifrolumab 300 mg |
|---|---|---|---|---|
| Medium TRLP (n = 13, 7) | −6.10 | −18.20 | 4.79E−2 | 3.13E-2 |
| Small TRLP (n = 7, 6) | −41.90 | −30.90 | 5.78E−1 | 9.38E-2 |

TABLE 7-4-continued

Longitudinal changes in lipid NMR measurements after type I IFN inhibition in patients with SLE with a baseline NMR defect[a]

| Median change Signed rank test p-value Lipid analyte (n = placebo, anifrolumab) | Placebo | Anifrolumab 300 mg | Placebo | Anifrolumab 300 mg |
|---|---|---|---|---|
| Very small TRLP (n = 9, 4) | 16.10 | 29.50 | 3.46E−2 | 2.50E−1 |
| H3P (n = 7, 7) | 0.70 | 1.50 | 2.71E−1 | 2.23E−2 |

[a]Lipid analytes were included in the assessment if ≥10 patients had a defect at baseline compared with healthy donors, with a defect defined as a lipid measurement outside the bounds of two standard deviations from the mean of the healthy donors. IFN, interferon; NMR, nuclear magnetic resonance; SLE, systemic lupus erythematosus; TRLP, triglyceride-rich lipoprotein.

It was analysed whether IR correlated with type I IFN measures at baseline. Analysis of all patients, regardless of IR status, showed no significant difference in IR between those who were IFNGS test-high or test-low. No correlation was detected between IR and IFN-α or 21-IFNGS (Table 7-1). However, among the few patients who had early IR (≥1.9 [49]), IFNGS test-high patients had greater IR than IFNGS test-low patients (p=0.046). There was no reduction in percentage IR change from baseline after anifrolumab compared with placebo, even in patients in the upper quartile of IR (IR≥3.9). Overall, these results do not support a role for type I IFN pathway inhibition in modulation of IR in SLE, although there may be value in examining this relationship in a cohort further enriched for IR.

GlycA levels were significantly elevated in IFNGS test-high patients compared with healthy donors (AUC=0.84, p<0.001; FIG. 10A). The effect of anifrolumab treatment on GlycA levels in IFNGS test-high patients who had increased GlycA at baseline were investigated. Surprisingly GlycA levels significantly decreased by day 365 with anifrolumab (n=10, p=0.006), but not with placebo (n=11; FIG. 10B). These results demonstrate that type I IFN-signalling inhibition in SLE significantly normalized GlycA toward healthy donor levels.

Similar to the observed normalization of CEC, it was found that type I IFN pathway inhibition decreased GlycA levels in SLE. GlycA was previously associated with neutrophil gene networks, and the major protein contributors to the GlycA NMR signal (α1-acid glycoprotein and haptoglobin) can be synthesized and secreted from neutrophil granules[31]. These observations support a model centred on pathogenic neutrophil effector functions leading to aberrant type I IFN production, cardiometabolic dysregulation, and vascular damage in SLE (FIG. 11). These findings further support a model where vascular damage occurs through multiple mechanisms driven by the downstream effects of unabated IFN-α signalling.

Studying CVD risk in SLE using traditional approaches has low feasibility given disease incidence/prevalence and relatively young age at lupus diagnosis. Identification of meaningful biomarkers of CVD risk to select patients for intervention is a promising approach to address such challenges. The present disclosure advantageously demonstrates that several subclinical markers with direct physiological links to SLE-associated CVD risk (enhanced NET formation, impaired CEC, and elevated GlycA) are significantly modulated by anifrolumab, which have the potential to be practical tools to facilitate earlier CVD detection and improved symptom monitoring of CVD risk and vasculopathy.

8 EXAMPLE 4: EFFICACY OF ANIFROLUMAB IN TREATING CARDIOVASCULAR DISEASE IN SLE PATIENTS

8.1 Introduction

The similarity in design of the TULIP-1 and TULIP-2 trials facilitated pooling of data for assessment of individual organ systems with greater statistical power than possible with individual trials alone. In this post hoc analysis of pooled data from the TULIP-1 and TULIP-2 trials, we assessed the effects of anifrolumab on individual SLE organ domain disease activity.

8.2 Methods

8.2.1 Patients and Study Design

This was a post hoc analysis of pooled data from the 52-week TULIP-1 and TULIP-2 trials, in which patients who had moderate to severe SLE despite standard therapy with oral glucocorticoids, antimalarials, and/or immunosuppressants were randomized to receive anifrolumab 300 mg or placebo intravenously every 4 weeks for 48 weeks.

The study design and methods have been described in detail previously[26,27]. In brief, all patients were aged 18 to 70 years and fulfilled the American College of Rheumatology classification criteria for SLE. Patients with active severe neuropsychiatric SLE or severe lupus nephritis were excluded. Mandatory attempts to taper oral glucocorticoids to ≤7.5 mg/day between Week 8 and Week 40 were required for patients receiving prednisone or equivalent≥10 mg/day at baseline; tapering was also permitted for patients receiving lower doses at baseline. In all patients, glucocorticoid doses were required to be stable from Week 40 through Week 52.

8.2.2 Study Endpoints and Assessments

Organ domain involvement was assessed using BILAG-2004[17] and SLEDAI-2K.[18] BILAG-2004 response was defined as a reduction from A (severe disease) at baseline to B (moderate), C (mild), or D (no current disease), or from B at baseline to C or D. The proportions of patients who improved 1 step (eg, from A to B or B to C), 2 steps (eg, from A to C or B to D), and up to 3 steps (ie, from A to D) in a given organ domain from baseline to Week 52 were evaluated. SLEDAI-2K improvement was defined as a reduction in domain scores in patients with baseline scores≥0. For both BILAG-2004 and SLEDAI-2K, patients who were treated with restricted medication beyond protocol-allowed thresholds or who discontinued investigational product were classified as nonresponders.

In addition to changes in mean hematologic and serologic values, the percentages of patients with abnormal (low or high) values at baseline who converted to normal values at Week 52 were evaluated. Patients who discontinued study treatments or had missing Week 52 data were assumed not to have normalized.

8.2.3 Statistical Analyses

The similar TULIP-1 and TULIP-2 trial designs allowed for the results to be pooled. BILAG-2004 and SLEDAI-2K organ domain responder rates, SLEDAI-2K organ domain responders over time, CLASI-A responders over time, and ≥50% reductions in joint counts from baseline were calculated using a stratified Cochran-Mantel-Haenszel approach, with stratification factors (matching those in the TULIP studies) of SLEDAI-2K score at screening, type I IFN gene signature test status at screening, and Day 1 oral glucocorticoid dose. The reported 2-sided P-values and 95% confidence intervals (CIs) are based on this approach. All reported P-values are nominal. For assessment of pooled TULIP data, TULIP-1 data were analysed according to the TULIP-2-revised restricted medication analytic rules. Missing data were imputed using the last observation carried forward for the first visit with missing data; subsequent visits with missing data were not imputed.

8.3 Results

8.3.1 Baseline Characteristics

Data were pooled for 726 patients; 360 received anifrolumab 300 mg (180 patients in each trial), and 366 received placebo (184 and 182 patients in TULIP-1 and TULIP-2, respectively). Baseline demographics and background treatment for SLE were comparable between groups (Table 8-1).

Of the 726 patients enrolled, the mean age was 41.8 years; 92.8% were women, and 66.0% were white. At baseline, 82.0% (595/726) of patients were receiving oral glucocorticoids, of whom 52.8% (190/360) of the anifrolumab group and 50.5% (185/366) of the placebo group were receiving ≥10 mg/day (prednisone or equivalent). Baseline disease activity levels, measured with BILAG and SLEDAI-2K, were similar between the pooled treatment arms (Table 8-1), with a mean SLEDAI-2K of approximately 11 and approximately half of all patients having at least one BILAG A domain score.

Figure 14A:
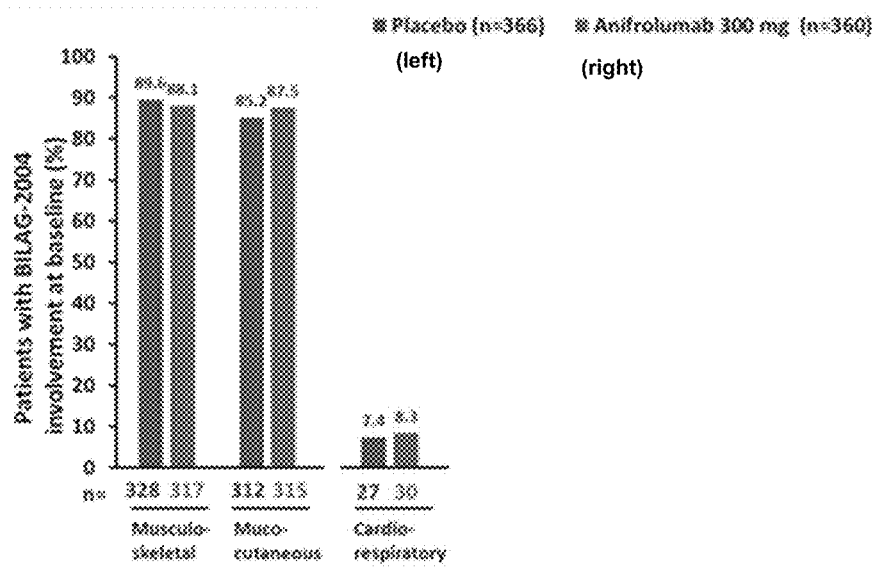
Figure 14B:
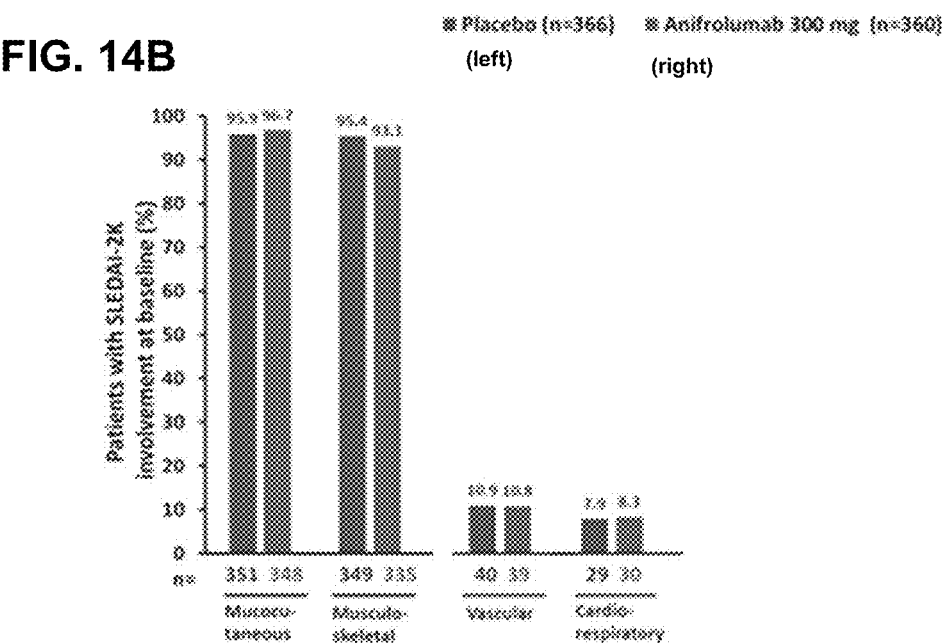

Baseline organ domain involvement assessed using BILAG-2004 and SLEDAI-2K was similar between treatment groups (FIG. 14A and FIG. 14B). The most commonly affected organ domains at baseline were mucocutaneous (BILAG-2004 86.4% [627/726]; SLEDAI-2K 96.3% [699/726]) and musculoskeletal (BILAG-2004 88.8% [645/726]; SLEDAI-2K 94.2% [684/726]) FIG. 14A and FIG. 14B). In the most commonly affected BILAG-2004 domains, musculoskeletal and mucocutaneous, the majority of patients had severe or moderate disease activity at baseline as shown by the overall frequency of BILAG A (musculoskeletal 31.5% [229/726], mucocutaneous 21.9% [159/726]) or BILAG B (musculoskeletal 57.3% [416/726]; mucocutaneous 64.5% [468/726]) scores.

TABLE 8-1

Baseline patient demographics, disease characteristics, and SLE medications of patients enrolled in and TULIP-2 (pooled data)

| Characteristics | Placebo (n = 366) | Anifrolumab 300 mg (n = 360) |
|---|---|---|
| Age, mean (SD), years | 41.0 (11.9) | 42.6 (12.0) |
| Female, n (%) | 341 (93.2) | 333 (92.5) |
| Race, n (%) | | |
| White | 244 (66.7) | 235 (65.3) |
| Black | 48 (13.1) | 46 (12.8) |
| Asian | 35 (9.6) | 41 (11.4) |
| Other | 31 (8.5) | 30 (8.3) |
| Time from initial SLE diagnosis to randomization, median (range), months | 78.5 (4-503) | 91.0 (0-555) |
| BILAG-2004, n (%) | | |
| ≥1 A item | 179 (48.9) | 174 (48.3) |
| No A items and ≥2 B items | 162 (44.3) | 170 (47.2) |
| SLEDAI-2K | | |
| Mean (SD) | 11.5 (3.7) | 11.4 (3.8) |
| ≥10, n (%) | 266 (72.7) | 254 (70.6) |
| PGA, mean (SD) | 1.8 (0.4) | 1.8 (0.4) |
| CLASI-A | 7.8 (7.2) | 8.4 (7.6) |
| Mean (SD) | 7.8 (7.2) | 8.4 (7.6) |
| ≥10, n (%) | 4 (25.7) | 107 (29.7) |
| SDI, mean (SD) | 0.6 (0.9) | 0.6 (1.0) |
| Number of swollen joints, mean (SD) | 7.2 (5.7) | 6.8 (5.8) |
| Number of tender joints, mean (SD) | 10.8 (7.5) | 10.3 (7.4) |
| Baseline treatment for SLE, n (%) | | |
| Oral glucocorticoid use[a] | 304 (83.1) | 291 (80.8) |
| <10 mg/day | 181 (49.5) | 170 (47.2) |
| ≥10 mg/day | 185 (50.5) | 190 (52.8) |
| Antimalarial | 267 (73.0) | 243 (67.5) |
| Immunosuppressant[b] | 177 (48.4) | 173 (48.1) |

BILAG-2004, British Isles Lupus Assessment Group-2004; CLASI, Cutaneous Lupus Erythematosus Disease Area and Severity Index; CLASI-A, CLASI activity score; PGA, Physician's Global Assessment; SD, standard deviation; SDI, Systemic Lupus International Collaborating Clinics/American College of Rheumatology Damage Index; SLE, systemic lupus erythematosus; SLEDAI-2K, Systemic Lupus Erythematosus Disease Activity Index 2000.

[a]Oral glucocorticoids contains prednisone or equivalent;

[b]Immunosuppressant: azathioprine, methotrexate, mycophenolate mofetil, mycophenolic acid, and mizoribine.

8.3.2 Efficacy in BILAG-2004 Cardiorespiratory Organ Domain

Improvements favouring anifrolumab for the mucocutaneous, musculoskeletal and cardiorespiratory BILAG-2004 domains were observed from Week 4, Week 32 and Week 28, respectively (FIG. 15).

8.3.3 Efficacy in SLEDAI-2K Cardiorespiratory and Vascular Organ Domain

At Week 52, significantly more anifrolumab-treated than placebo-receiving patients had improvements in the SLEDAI-2K organ domains most frequently affected at baseline: mucocutaneous (54.7% [190/348] vs 39.4% [138/351]; nominal P<0.001), musculoskeletal (48.8% [164/335] vs 40.4% [141/349]; nominal P<0.05), nominal P<0.05) (FIG. 16). Greater proportions of patients receiving anifrolumab versus placebo had improvements at Week 52 for vascular and cardiorespiratory SLEDAI-2K domains (FIG. 16).

8.3.4 Laboratory Markers—Hematology and Serology

Patients in the anifrolumab and placebo groups had similar mean hematology values at baseline (Table 8-2).

At Week 52, treatment effects favouring anifrolumab versus placebo were seen for mean (SD) increase in haemoglobin (0.5 [10.59] vs −2.7 [11.33] g/L) and platelets (24.3 [58.2] vs 3.2 [49.8]×109/L). In the anifrolumab group, 6.4% (23/360) of patients with leukopenia at baseline demonstrated normalization, versus 3.0% (11/366) of patients receiving placebo.

Among patients who were anti-dsDNA positive at baseline, mean (SD) levels of anti-dsDNA antibodies decreased with anifrolumab treatment, compared with an increase for placebo (−25.0 [238.4] vs 28.0 [498.5] U/mL; Table 3). Accordingly, 7.8% (13/167) of patients receiving anifrolumab versus 5.8% (9/155) of patients receiving placebo converted to anti-dsDNA negative by Week 52 (Table 8-3).

At Week 52, greater improvements from baseline in mean (SD) complement C3 levels were observed with anifrolumab (0.13 [0.18]) versus placebo (0.04 [0.16] U/mL) (Table 8-3). In patients with low C3 at baseline, normalization was observed in 16.2% (21/130) of anifrolumab-treated and 9.5% (13/137) of placebo-treated patients. Similarly, nor-

TABLE 8-2

Changes in hematologic measures from baseline to Week 52

| | Placebo (n = 365)[a] | Anifrolumab 300 mg (n = 360) |
|---|---|---|
| Hemoglobin | | |
| Baseline mean (SD), g/L | 126.0 (15.2) | 125.0 (14.8) |
| Change from baseline, mean (SD), g/L | −2.7 (11.33) | 0.5 (10.59) |
| Normalization at Week 52 in patients with abnormal hemoglobin at baseline, n (%)[b] | 0 (0) | 0 (0) |
| Hematocrit | | |
| Baseline mean (SD) | 0.4 (0.04) | 0.4 (0.04) |
| Change from baseline, mean (SD) | −0.005 (0.03) | 0.005 (0.03) |
| Normalization at Week 52 in patients with abnormal hematocrit at baseline, n (%)[b] | 0 (0) | 0 (0) |
| Lymphocytes | | |
| Baseline mean (SD), $10^9$/L | 1.3 (0.6) | 1.3 (0.6) |
| Change from baseline, mean (SD), $10^9$/L | −0.03 (0.5) | 0.3 (0.6) |
| Normalization at Week 52 in patients with abnormal lymphocytes at baseline, n (%)[b] | 11 (3.0) | 23 (6.4) |
| Neutrophils | | |
| Baseline mean (SD), $10^9$/L | 4.0 (2.1) | 3.8 (1.8) |
| Change from baseline, mean (SD), $10^9$/L | 0.1 (2.0) | 0.7 (1.8) |
| Normalization at Week 52 in patients with abnormal neutrophils at baseline, n (%)[b] | 0 (0) | 1 (0.3) |
| Platelets | | |
| Baseline mean (SD), $10^9$/L | 250.2 (79.8) | 239.9 (78.2) |
| Change from baseline, mean (SD), $10^9$/L | 3.2 (49.8) | 24.3 (58.2) |
| Normalization at Week 52 in patients with abnormal platelets at baseline, n (%)[b] | 1 (0.3) | 0 (0.0) |

SD, standard deviation.

[a]1 patient was removed from the analysis after study completion;

[b]Range of normal values for hemoglobin (>60 to <200 g/L), hematocrit (>0.18 to <0.64), lymphocytes (>0.5 to <10.0 109/L), neutrophils (>0.5 to <20.0 109/L), and platelets (>20 to <600 109/L).

malization of low baseline C4 occurred in more patients receiving anifrolumab versus placebo (22.6% [19/84] vs 7.1% [6/85]).

TABLE 8-3

Change in laboratory markers from baseline to Week 52

|  | Placebo (n = 366) | Anifrolumab 300 mg (n = 360) |
|---|---|---|
| Anti-dsDNA[a,b] | | |
| Anti-dsDNA positive at baseline, n (%) | 155 (42.3) | 167 (43.4) |
| Mean (SD), U/mL | 211.95 (549.65) | 129.34 (261.40) |
| Change from baseline, mean (SD), U/mL | 27.96 (498.47) | −24.98 (238.39) |
| Normalization at Week 52 in patients with abnormal anti-dsDNA at baseline, n (%) | 9 (5.8%) | 13 (7.8%) |
| C3[a,c] | | |
| Abnormal C3 at baseline, n (%) | 137 (37.4) | 130 (36.1) |
| Mean (SD), U/mL | 0.70 (0.14) | 0.69 (0.15) |
| Change from baseline, mean (SD), U/mL | 0.04 (0.16) | 0.13 (0.18) |
| Normalization at Week 52 in patients with abnormal C3 at baseline, n (%) | 13 (9.5) | 21 (16.2) |
| C4[a,d] | | |
| Abnormal C4 at baseline, n (%) | 85 (23.2) | 84 (23.3) |
| Mean (SD), U/mL | 0.07 (0.02) | 0.07 (0.02) |
| Change from baseline, mean (SD), U/mL | 0.02 (0.04) | 0.02 (0.03) |
| Normalization at Week 52 in patients with abnormal C4 at baseline, n (%) | 6 (7.1) | 19 (22.6) | anti-dsDNA, anti-double-stranded DNA; C3, complement 3; C4, complement 4; SD, standard deviation.
[a]Only patients with baseline positive anti-dsDNA or low C3 or C4 are included in the summary statistics for the respective variables;
[b]Anti-dsDNA antibody "positive" defined as a result of >15 U/mL;
[c]Complement C3 "abnormal" levels defined as a result of <0.9 g/L;
[d]Complement C4 "abnormal" levels defined as a result of <0.1 g/L.

8.4 Discussion

In this post hoc analysis of pooled data from the TULIP-1 and TULIP-2 trials, compared with placebo, anifrolumab treatment was associated with greater improvement in the cardiorespiratory and vascular organ domains of patients with moderate to severe SLE. Anifrolumab treatment also resulted in greater frequency of hematologic and serologic normalization compared with placebo.

Results of the TULIP-1 and TULIP-2 trials previously demonstrated that patients treated with anifrolumab had higher BICLA responder rates compared with patients receiving placebo. The present analyses also surprisingly demonstrate consistency between BILAG-2004 and SLE-DAI-2K activity assessments in the cardiorespiratory and cardiovascular organ domains.

Serologic activity is indicative of immune system activation and is typically associated with SLE disease activity. More anifrolumab-treated patients were able to normalize anti-dsDNA antibodies and complement C3 and C4 levels compared with placebo-treated patients. These results suggest that the effects of anifrolumab on serologic markers are consistent with the greater improvements observed in those treated with anifrolumab compared with placebo in the SLEDAI-2K immunologic domain.

In conclusion, in pooled data from the phase 3 TULIP-1 and TULIP-2 trials, compared with placebo, anifrolumab treatment in patients with moderate to severe SLE was associated with improvements across cardiovascular and cardiorespiratory organ systems, as measured by BILAG-2004 and SLEDAI-2K domain scores. These data thus surprisingly demonstrate the inhibition of type I IFN signalling treats cardiovascular disease in SLE patients.

9 EXAMPLE 5: INJECTION DEVICE

Anifrolumab is administered by an injection device [1] [9] such as a prefilled syringe (PFS) (FIG. 17A) or an autoinjector (AI) (FIG. 17B).

9.1 Autoinjector

Anifrolumab may be administered by an autoinjector [1]. The autoinjector is shown in exploded view (FIG. 18A) and in an assembled form (FIG. 18B). A label [4] is wrapped around and attached to the autoinjector [1] (FIG. 18C). The autoinjector has an autoinjector housing [3], cap and cap remover [2] and drive unit [5]. The liquid anifrolumab formulation unit dose [6] is contained in the autoinjector housing [3]. The unit dose [6] can be viewed through the viewing window [7].

9.2 Accessorized Pre-Frilled Syringe

Anifrolumab may be administered by accessorized prefilled syringe (APFS) [8]. The APFS [8] includes the unit dose of anifrolumab [6] contained in a primary container [9] shown in an assembled state in FIG. 19A and in an exploded view in FIG. 19B. The primary container [9] has a plunger stopper [16]. The primary container has a nominal fill volume [17] of 0.8 ml but may contain slightly more than 0.8 ml. The remainder of the space in the primary container [9] is taken up by an air bubble [18]. The air bubble [18] may have a size of 3-5 mm, optionally, 4 mm. The primary container [9] has a defined stopper position [19].

Figure 19C:
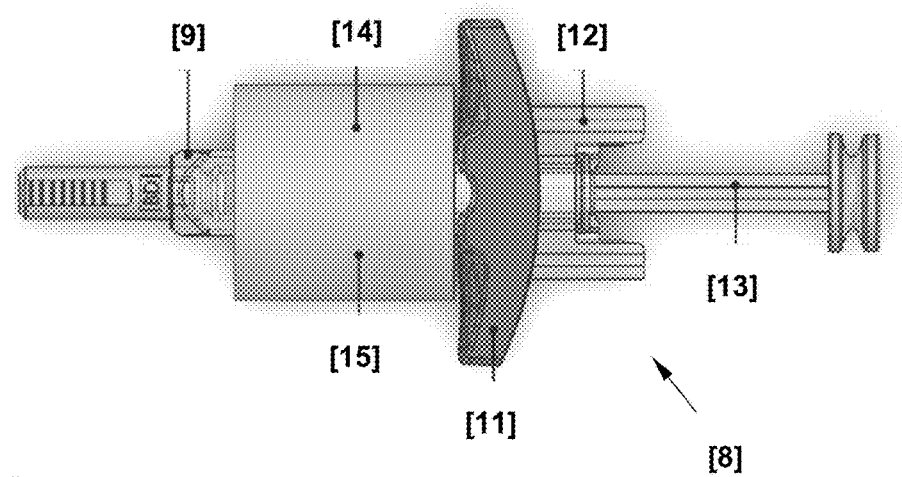
Figure 19D:
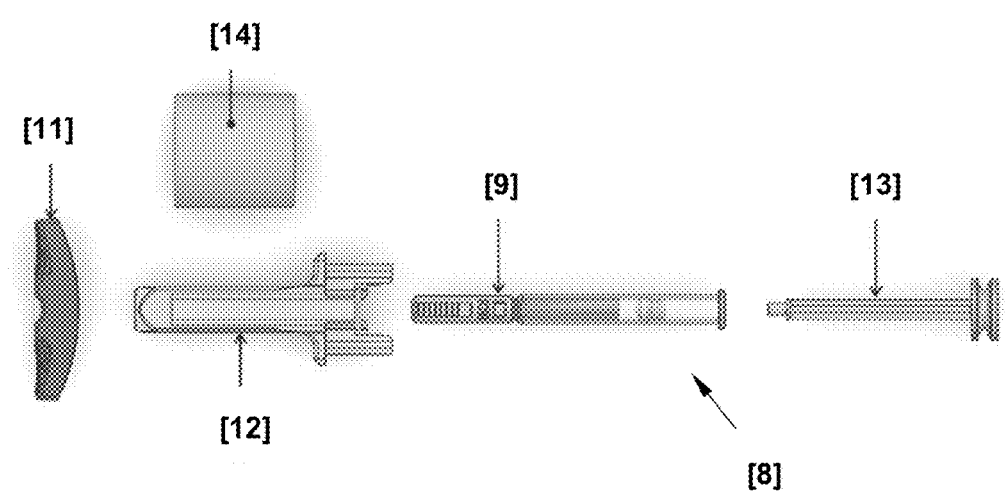

The accessorized pre-filled syringe (APFS) primary container [9] is provided in a PFS assembly [8] including a needle guard [12], a finger flange [11] and a plunger rod [13] (FIG. 19C, FIG. 19D). A label [14] is provided with the primary container [9] in the PFS assembly [8]. The label [14] is wrapped around the syringe [9] in the label placement position [15].

9.3 Packaging

The injection device [1] [8] is provided in a kit [20] (FIG. 20). A label [4] [14] is provided with the APFS or autoinjector in the packaging. The label includes instruction for the use of the injection device [1], [8]. The packaging includes a tamper seal.

REFERENCES

All publications mentioned in the specification are herein incorporated by reference.

(1) Skamra, C.; Ramsey-Goldman, R. Management of Cardiovascular Complications in Systemic Lupus Erythematosus. Int J Clin Rheumtol 2010, 5 (1), 75-100. https://doi.org/10.2217/ijr.09.73.

(2) Björnadal, L.; Yin, L.; Granath, F.; Klareskog, L.; Ekbom, A. Cardiovascular Disease a Hazard despite Improved Prognosis in Patients with Systemic Lupus Erythematosus: Results from a Swedish Population Based Study 1964-95. The Journal of Rheumatology 2004, 31 (4), 713-719.

(3) Nossent, J.; Cikes, N.; Kiss, E.; Marchesoni, A.; Nassonova, V.; Mosca, M.; Olesinska, M.; Pokorny, G.; Rozman, B.; Schneider, M.; Vlachoyiannopoulos, P. G.; Swaak, A. Current Causes of Death in Systemic Lupus Erythematosus in Europe, 2000-2004: Relation to Disease Activity and Damage Accrual. Lupus 2007, 16 (5), 309-317. https://doi.org/10.1177/0961203307077987.

(4) Wade, N. S.; Major, A. S. The Problem of Accelerated Atherosclerosis in Systemic Lupus Erythematosus: Insights into a Complex Co-Morbidity. Thromb Haemost 2011, 106 (5), 849-857. https://doi.org/10.1160/TH 11-05-0330.

(5) Pons-Estel, G. J.; Alarcon, G. S.; Scofield, L.; Reinlib, L.; Cooper, G. S. Understanding the Epidemiology and Progression of Systemic Lupus Erythematosus. Semin Arthritis Rheum 2010, 39 (4), 257-268. https://doi.org/10.1016/j.semarthrit.2008.10.007.

(6) McCauliffe, D. P. Cutaneous Lupus Erythematosus. Semin Cutan Med Surg 2001, 20 (1), 14-26. https://doi.org/10.1053/sder.2001.23091.

(7) Uva, L.; Miguel, D.; Pinheiro, C.; Freitas, J. P.; Marques Gomes, M.; Filipe, P. Cutaneous Manifestations of Systemic Lupus Erythematosus. Autoimmune Dis 2012, 2012, 834291. https://doi.org/10.1155/2012/834291.

(8) Zayat, A. S.; Md Yusof, M. Y.; Wakefield, R. J.; Conaghan, P. G.; Emery, P.; Vital, E. M. The Role of Ultrasound in Assessing Musculoskeletal Symptoms of Systemic Lupus Erythematosus: A Systematic Literature Review. Rheumatology (Oxford) 2016, 55 (3), 485-494. https://doi.org/10.1093/rheumatology/kev343.

(9) Sa, C.; E, A.; A, R.; D, I. Damage and mortality in a group of British patients with systemic lupus erythematosus followed up for over 10 years https://pubmed.ncbi.nlm.nih.gov/19359343/(accessed Feb. 8, 2021). https://doi.org/10.1093/rheumatology/kep062.

(10) Murimi-Worstell, I. B.; Lin, D. H.; Nab, H.; Kan, H. J.; Onasanya, O.; Tierce, J. C.; Wang, X.; Desta, B.; Alexander, G. C.; Hammond, E. R. Association between Organ Damage and Mortality in Systemic Lupus Erythematosus: A Systematic Review and Meta-Analysis. BMJ Open 2020, 10 (5), e031850. https://doi.org/10.1136/bmjopen-2019-031850.

(11) Doria, A.; Briani, C. Lupus: Improving Long-Term Prognosis. Lupus 2008, 17 (3), 166-170. https://doi.org/10.1177/0961203307087612.

(12) Petri, M. Long-Term Outcomes in Lupus. Am J Manag Care 2001, 7 (16 Suppl), S480-485.

(13) Zonana-Nacach, A.; Barr, S. G.; Magder, L. S.; Petri, M. Damage in Systemic Lupus Erythematosus and Its Association with Corticosteroids. Arthritis Rheum 2000, 43 (8), 1801-1808. https://doi.org/10.1002/1529-0131 (200008)43:8<1801::AID-ANR16>3.0.CO; 2-O.

(14) Urowitz, M. B.; Bookman, A. A.; Koehler, B. E.; Gordon, D. A.; Smythe, H. A.; Ogryzlo, M. A. The Bimodal Mortality Pattern of Systemic Lupus Erythematosus. Am J Med 1976, 60 (2), 221-225. https://doi.org/10.1016/0002-9343(76)90431-9.

(15) Carlucci, P. M.; Purmalek, M. M.; Dey, A. K.; Temesgen-Oyelakin, Y.; Sakhardande, S.; Joshi, A. A.; Lerman, J. B.; Fike, A.; Davis, M.; Chung, J. H.; Playford, M. P.; Naqi, M.; Mistry, P.; Gutierrez-Cruz, G.; Dell'Orso, S.; Naz, F.; Salahuddin, T.; Natarajan, B.; Manna, Z.; Tsai, W. L.; Gupta, S.; Grayson, P.; Teague, H.; Chen, M. Y.; Sun, H.-W.; Hasni, S.; Mehta, N. N.; Kaplan, M. J. Neutrophil Subsets and Their Gene Signature Associate with Vascular Inflammation and Coronary Atherosclerosis in Lupus. JCI Insight 2018, 3 (8). https://doi.org/10.1172/jci.insight.99276.

(16) Ferguson, G. T.; Mansur, A. H.; Jacobs, J. S.; Hebert, J.; Clawson, C.; Tao, W.; Wu, Y.; Goldman, M. Assessment of an Accessorized Pre-Filled Syringe for Home-Administered Benralizumab in Severe Asthma. J Asthma Allergy 2018, 11, 63-72. https://doi.org/10.2147/JAA.S157762.

(17) Interferon-Inducible Gene Expression Kit As a Potential Diagnostic Test for Anifrolumab: Analytical Validation for Use in Clinical Trials. ACR Meeting Abstracts.

(18) Touma, Z.; Urowitz, M.; Gladman, D. SLEDAI-2K for a 30-Day Window. Lupus 2010, 19 (1), 49-51. https://doi.org/10.1177/0961203309346505.

(19) Gruppen, E. G.; Riphagen, I. J.; Connelly, M. A.; Otvos, J. D.; Bakker, S. J. L.; Dullaart, R. P. F. GlycA, a Pro-Inflammatory Glycoprotein Biomarker, and Incident Cardiovascular Disease: Relationship with C-Reactive Protein and Renal Function. PLOS ONE 2015, 10 (9), e0139057. https://doi.org/10.1371/journal.pone.0139057.

(20) Connelly, M. A.; Otvos, J. D.; Shalaurova, I.; Playford, M. P.; Mehta, N. N. GlycA, a Novel Biomarker of Systemic Inflammation and Cardiovascular Disease Risk. Journal of Translational Medicine 2017, 15 (1).

(21) Fashanu, O. E.; Oyenuga, A. O.; Zhao, D.; Tibuakuu, M.; Mora, S.; Otvos, J. D.; Stein, J. H.; Michos, E. D. GlycA, a Novel Inflammatory Marker and Its Association With Peripheral Arterial Disease and Carotid Plaque: The Multi-Ethnic Study of Atherosclerosis. Angiology 2019, 70 (8), 737-746. https://doi.org/10.1177/0003319719845185.

(22) Ormseth, M. J.; Chung, C. P.; Oeser, A. M.; Connelly, M. A.; Sokka, T.; Raggi, P.; Solus, J. F.; Otvos, J. D.; Stein, C. M. Utility of a Novel Inflammatory Marker, GlycA, for Assessment of Rheumatoid Arthritis Disease Activity and Coronary Atherosclerosis. Arthritis Res Ther 2015, 17 (1). https://doi.org/10.1186/s13075-015-0646-x.

(23) Chung, S. T.; Matta, S.; Meyers, A.; Cravalho, C. K.; Villalobos-Perez, A.; Mabundo, L.; Courville, A. B.; Sampson, M. L.; Otvos, J. D.; Magge, S. N. 1243-P: NMR-Derived Biomarkers Identify Cardiometabolic Disease Risk in Youth. Diabetes 2020, 69 (Supplement 1). https://doi.org/10.2337/db20-1243-P.

(24) Tummala, R.; Rouse, T.; Berglind, A.; Santiago, L. Safety, Tolerability and Pharmacokinetics of Subcutaneous and Intravenous Anifrolumab in Healthy Volunteers.

*Lupus Sci Med* 2018, 5 (1), e000252. https://doi.org/10.1136/lupus-2017-000252.

(25) Furie, R.; Khamashta, M.; Merrill, J. T.; Werth, V. P.; Kalunian, K.; Brohawn, P.; Illei, G. G.; Drappa, J.; Wang, L.; Yoo, S.; Investigators, for the C. S. Anifrolumab, an Anti-Interferon-α Receptor Monoclonal Antibody, in Moderate-to-Severe Systemic Lupus Erythematosus. *Arthritis & Rheumatology (Hoboken, N.j.)* 2017, 69 (2), 376. https://doi.org/10.1002/art.39962.

(26) Furie, R. A.; Morand, E. F.; Bruce, I. N.; Manzi, S.; Kalunian, K. C.; Vital, E. M.; Ford, T. L.; Gupta, R.; Hiepe, F.; Santiago, M.; Brohawn, P. Z.; Berglind, A.; Tummala, R. Type I Interferon Inhibitor Anifrolumab in Active Systemic Lupus Erythematosus (TULIP-1): A Randomised, Controlled, Phase 3 Trial. *The Lancet Rheumatology* 2019, 1 (4), e208-e219. https://doi.org/10.1016/S2665-9913(19)30076-1.

(27) Morand, E. F.; Furie, R.; Tanaka, Y.; Bruce, I. N.; Askanase, A. D.; Richez, C.; Bae, S.-C.; Brohawn, P. Z.; Pineda, L.; Berglind, A.; Tummala, R. Trial of Anifrolumab in Active Systemic Lupus Erythematosus. *New England Journal of Medicine* 2020, 382 (3), 211-221. https://doi.org/10.1056/NEJMoa1912196.

(28) Tanaka, Y.; Tummala, R. Anifrolumab, a Monoclonal Antibody to the Type I Interferon Receptor Subunit 1, for the Treatment of Systemic Lupus Erythematosus: An Overview from Clinical Trials. *Modern Rheumatology* 2020, 0 (0), 1-12. https://doi.org/10.1080/14397595.2020.1812201.

(29) Furie, R. A.; Leon, G.; Thomas, M.; Petri, M. A.; Chu, A. D.; Hislop, C.; Martin, R. S.; Scheinberg, M. A.; PEARL-SC Study. A Phase 2, Randomised, Placebo-Controlled Clinical Trial of Blisibimod, an Inhibitor of B Cell Activating Factor, in Patients with Moderate-to-Severe Systemic Lupus Erythematosus, the PEARL-SC Study. *Ann Rheum Dis* 2015, 74 (9), 1667-1675. https://doi.org/10.1136/annrheumdis-2013-205144.

(30) Villanueva, E.; Yalavarthi, S.; Berthier, C. C.; Hodgin, J. B.; Khandpur, R.; Lin, A. M.; Rubin, C. J.; Zhao, W.; Olsen, S. H.; Klinker, M.; Shealy, D.; Denny, M. F.; Plumas, J.; Chaperot, L.; Kretzler, M.; Bruce, A. T.; Kaplan, M. J. Netting Neutrophils Induce Endothelial Damage, Infiltrate Tissues, and Expose Immunostimulatory Molecules in Systemic Lupus Erythematosus. *J Immunol* 2011, 187 (1), 538-552. https://doi.org/10.4049/jimmunol.1100450.

(31) Ritchie, S. C.; Wurtz, P.; Nath, A. P.; Abraham, G.; Havulinna, A. S.; Fearnley, L. G.; Sarin, A.-P.; Kangas, A. J.; Soininen, P.; Aalto, K.; Seppsls, I.; Raitoharju, E.; Salmi, M.; Maksimow, M.; Msnnisto, S.; Kshonen, M.; Juonala, M.; Ripatti, S.; Lehtimski, T.; Jalkanen, S.; Perola, M.; Raitakari, O.; Salomaa, V.; Ala-Korpela, M.; Kettunen, J.; Inouye, M. The Biomarker GlycA Is Associated with Chronic Inflammation and Predicts Long-Term Risk of Severe Infection. *Cell Syst* 2015, 1 (4), 293-301. https://doi.org/10.1016/j.cels.2015.09.007.

The invention claimed is:

1. A method of treating or reducing the risk for development of a cardiometabolic disease in a patient in need thereof, wherein the method comprises administering about 300 mg to about 1000 mg of an inhibitor of type I IFN signaling to the patient,
wherein the inhibitor is a human monoclonal antibody comprising
a) a heavy chain variable region complementarity determining region 1 (HCDR1) comprising the amino acid sequence of SEQ ID NO: 3;
b) a heavy chain variable region complementarity determining region 2 (HCDR2) comprising the amino acid sequence of SEQ ID NO: 4;
c) a heavy chain variable region complementarity determining region 3 (HCDR3) comprising the amino acid sequence of SEQ ID NO: 5;
d) a light chain variable region complementarity determining region 1 (LCDR1) comprising the amino acid sequence SEQ ID NO: 6;
e) a light chain variable region complementarity determining region 2 (LCDR2) comprising the amino acid sequence SEQ ID NO: 7; and
f) a light chain variable region complementarity determining region 3 (LCDR3) comprising the amino acid sequence SEQ ID NO: 8, and
wherein the patient has systemic lupus erythematosus (SLE), and wherein the cardiometabolic disease is selected from the group consisting of premature atherosclerosis, myocarditis, arrhythmia, valvular dysfunction, vasculitis, aortitis, atherosclerosis, and coronary vasculitis;
wherein the inhibitor is administered to the patient intravenously; and
wherein the patient has high levels of expression of GlycA, TNF-α, and IL-10 compared to a healthy subject.

2. The method of claim 1, wherein the antibody comprises: (a) a human heavy chain variable region comprising the amino acid sequence of SEQ ID NO: 1; (b) a human light chain variable region comprising the amino acid sequence of SEQ ID NO: 2.

3. The method of claim 1, wherein the antibody comprises: (a) a human heavy chain comprising the amino acid sequence of SEQ ID NO: 11; and (b) a human light chain comprising the amino acid sequence of SEQ ID NO: 12.

4. The method of claim 1, wherein administering the inhibitor reduces expression of GlycA; TNF-α or IL-10.

5. The method of claim 1, wherein the patient is identified as having a risk of development of a cardiometabolic disease.

6. The method of claim 1, wherein the patient has elevated serum protein levels of IFN-α compared to a healthy subject, and wherein administering the inhibitor decreases the serum protein levels of IFN-α in the patient.

7. The method of claim 1, comprising intravenously administering a dose of about 300 mg of inhibitor to the subject.

8. The method of claim 7, wherein the intravenous dose is administered every four weeks (Q4W).

9. The method of claim 1, wherein the cardiometabolic disease is premature atherosclerosis.

10. The method of claim 9, wherein the premature atherosclerosis is sub-clinical.

11. The method of claim 1, wherein the IFNAR1 inhibitor is a modified IgG1 class human monoclonal antibody.

* * * * *

SEQUENCE LISTING

```
Sequence total quantity: 12
SEQ ID NO: 1              moltype = AA  length = 117
FEATURE                   Location/Qualifiers
REGION                    1..117
                          note = VH
source                    1..117
                          mol_type = protein
                          organism = synthetic construct
SEQUENCE: 1
EVQLVQSGAE VKKPGESLKI SCKGSGYIFT NYWIAWVRQM PGKGLESMGL LYPGDSDIRY    60
SPSFQGQVTI SADKSITTAY LQWSSLKASD TAMYYCARHD IEGFDYWGRG TLVTVSS      117

SEQ ID NO: 2              moltype = AA  length = 108
FEATURE                   Location/Qualifiers
REGION                    1..108
                          note = VL
source                    1..108
                          mol_type = protein
                          organism = synthetic construct
SEQUENCE: 2
EIVLTQSPGT LSLSPGERAT LSCRASQSVS SSFFAWYQQK PGQAPRLLIY GASSRATGIP    60
DRLSGSGSGT DFTLTITRLE PEDFAVYYCQ QYDSSAITFG QGTRLEIK                108

SEQ ID NO: 3              moltype = AA  length = 5
FEATURE                   Location/Qualifiers
REGION                    1..5
                          note = HCDR1
source                    1..5
                          mol_type = protein
                          organism = synthetic construct
SEQUENCE: 3
NYWIA                                                                 5

SEQ ID NO: 4              moltype = AA  length = 17
FEATURE                   Location/Qualifiers
REGION                    1..17
                          note = HCDR2
source                    1..17
                          mol_type = protein
                          organism = synthetic construct
SEQUENCE: 4
IIYPGDSDIR YSPSFQG                                                   17
```

```
SEQ ID NO: 5           moltype = AA  length = 8
FEATURE                Location/Qualifiers
REGION                 1..8
                       note = HCDR3
source                 1..8
                       mol_type = protein
                       organism = synthetic construct
SEQUENCE: 5
HDIEGFDY                                                                    8

SEQ ID NO: 6           moltype = AA  length = 12
FEATURE                Location/Qualifiers
REGION                 1..12
                       note = LCDR1
source                 1..12
                       mol_type = protein
                       organism = synthetic construct
SEQUENCE: 6
RASQSVSSSF FA                                                              12

SEQ ID NO: 7           moltype = AA  length = 7
FEATURE                Location/Qualifiers
REGION                 1..7
                       note = LCDR2
source                 1..7
                       mol_type = protein
                       organism = synthetic construct
SEQUENCE: 7
GASSRAT                                                                     7

SEQ ID NO: 8           moltype = AA  length = 9
FEATURE                Location/Qualifiers
REGION                 1..9
                       note = LCDR3
source                 1..9
                       mol_type = protein
                       organism = synthetic construct
SEQUENCE: 8
QQYDSSAIT                                                                   9

SEQ ID NO: 9           moltype = AA  length = 107
FEATURE                Location/Qualifiers
REGION                 1..107
                       note = Light chain, constant
source                 1..107
                       mol_type = protein
                       organism = synthetic construct
SEQUENCE: 9
RTVAAPSVFI FPPSDEQLKS GTASVVCLLN NFYPREAKVQ WKVDNALQSG NSQESVTEQD           60
SKDSTYSLSS TLTLSKADYE KHKVYACEVT HQGLSSPVTK SFNRGEC                        107

SEQ ID NO: 10          moltype = AA  length = 330
FEATURE                Location/Qualifiers
REGION                 1..330
                       note = Constant light
source                 1..330
                       mol_type = protein
                       organism = synthetic construct
SEQUENCE: 10
ASTKGPSVFP LAPSSKSTSG GTAALGCLVK DYFPEPVTVS WNSGALTSGV HTFPAVLQSS           60
GLYSLSSVVT VPSSSLGTQT YICNVNHKPS NTKVDKRVEP KSCDKTHTCP PCPAPEFEGG          120
PSVFLFPPKP KDTLMISRTP EVTCVVVDVS HEDPEVKFNW YVDGVEVHNA KTKPREEQYN          180
STYRVVSVLT VLHQDWLNGK EYKCKVSNKA LPASIEKTIS KAKGQPREPQ VYTLPPSREE          240
MTKNQVSLTC LVKGFYPSDI AVEWESNGQP ENNYKTTPPV LDSDGSFFLY SKLTVDKSRW          300
QQGNVFSCSV MHEALHNHYT QKSLSLSPGK                                           330

SEQ ID NO: 11          moltype = AA  length = 447
FEATURE                Location/Qualifiers
REGION                 1..447
                       note = Heavy chain
source                 1..447
                       mol_type = protein
                       organism = synthetic construct
SEQUENCE: 11
EVQLVQSGAE VKKPGESLKI SCKGSGYIFT NYWIAWVRQM PGKGLESMGI IYPGDSDIRY           60
SPSFQGQVTI SADKSITTAY LQWSSLKASD TAMYYCARHD IEGFDYWGRG TLVTVSSAST          120
KGPSVFPLAP SSKSTSGGTA ALGCLVKDYF PEPVTVSWNS GALTSGVHTF PAVLQSSGLY          180
SLSSVVTVPS SSLGTQTYIC NVNHKPSNTK VDKRVEPKSC DKTHTCPPCP APEFEGGPSV          240
```

```
FLFPPKPKDT  LMISRTPEVT  CVVVDVSHED  PEVKFNWYVD  GVEVHNAKTK  PREEQYNSTY  300
RVVSVLTVLH  QDWLNGKEYK  CKVSNKALPA  SIEKTISKAK  GQPREPQVYT  LPPSREEMTK  360
NQVSLTCLVK  GFYPSDIAVE  WESNGQPENN  YKTTPPVLDS  DGSFFLYSKL  TVDKSRWQQG  420
NVFSCSVMHE  ALHNHYTQKS  LSLSPGK                                         447

SEQ ID NO: 12           moltype = AA   length = 215
FEATURE                 Location/Qualifiers
REGION                  1..215
                        note = Light chain
source                  1..215
                        mol_type = protein
                        organism = synthetic construct
SEQUENCE: 12
EIVLTQSPGT  LSLSPGERAT  LSCRASQSVS  SSFFAWYQQK  PGQAPRLLIY  GASSRATGIP   60
DRLSGSGSGT  DFTLTITRLE  PEDFAVYYCQ  QYDSSAITFG  QGTRLEIKRT  VAAPSVFIFP  120
PSDEQLKSGT  ASVVCLLNNF  YPREAKVQWK  VDNALQSGNS  QESVTEQDSK  DSTYSLSSTL  180
TLSKADYEKH  KVYACEVTHQ  GLSSPVTKSF  NRGEC                               215
```